US012091612B2

(12) United States Patent
Goto et al.

(10) Patent No.: US 12,091,612 B2
(45) Date of Patent: Sep. 17, 2024

(54) ELECTROCHROMIC ELEMENT

(71) Applicant: Ricoh Company, Ltd., Tokyo (JP)

(72) Inventors: Daisuke Goto, Kanagawa (JP); Fuminari Kaneko, Kanagawa (JP); Masato Shinoda, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 726 days.

(21) Appl. No.: 17/197,315

(22) Filed: Mar. 10, 2021

(65) Prior Publication Data

US 2021/0301197 A1 Sep. 30, 2021

(30) Foreign Application Priority Data

Mar. 30, 2020 (JP) .................................. 2020-061281
Mar. 3, 2021 (JP) .................................. 2021-033101

(51) Int. Cl.
*C09K 9/02* (2006.01)
*C08F 22/22* (2006.01)
(Continued)

(52) U.S. Cl.
CPC ................ *C09K 9/02* (2013.01); *C08F 22/22* (2013.01); *G02F 1/15165* (2019.01);
(Continued)

(58) Field of Classification Search
CPC .............. C09K 9/02; C09K 2211/1425; C09K 2211/1433; C08F 22/22; G02F 1/155; G02F 1/15165; G02F 2001/164
See application file for complete search history.

(56) References Cited

U.S. PATENT DOCUMENTS 9,688,706 B2 6/2017 Inoue et al.
9,829,762 B2 11/2017 Takahashi et al.
(Continued)

FOREIGN PATENT DOCUMENTS

CN 111116793 A 5/2020
EP 3 319 137 A1 5/2018
(Continued)

OTHER PUBLICATIONS

Extended European Search Report issued Aug. 30, 2021 in European Patent Application No. 21161876.4, 9 pages.
(Continued)

*Primary Examiner* — Bijan Ahvazi
(74) *Attorney, Agent, or Firm* — XSENSUS LLP

(57) ABSTRACT

An electrochromic element including a first electrode, second electrode facing the first electrode with gap, electrolyte layer between the first and second electrodes, and layer
(Continued)

including a compound represented by General Formula (1) where the layer is on or above the first electrode,

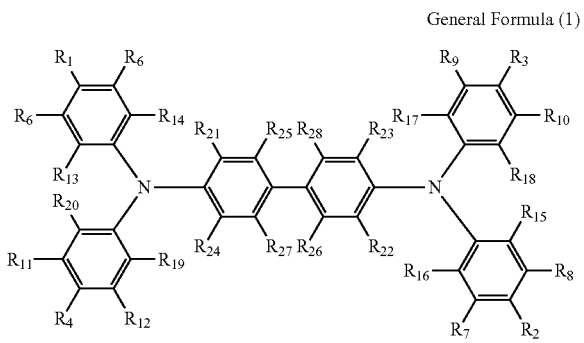

General Formula (1)

where $R_1$ to $R_4$ are each a monovalent organic group wherein no hydrogen atom is at a benzyl site where the monovalent group may include a polymerizable functional group; and $R_5$ to $R_{28}$ are each a hydrogen atom, alkyl or alkoxy group where $R_{25}$ and $R_{28}$, or $R_{26}$ and $R_{27}$ may be bonded to form a structure represented by General Formula (2),

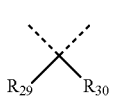

General Formula (2)

where $R_{29}$ and $R_{30}$ are each an alkyl, alkoxy or aryl group, and $R_{29}$ and $R_{30}$ may be bonded via a common bond to form a cyclic structure when $R_{29}$ and $R_{30}$ are aryl groups.

17 Claims, 2 Drawing Sheets

(51) Int. Cl.
  *G02F 1/1516* (2019.01)
  *G02F 1/155* (2006.01)
  *G02F 1/15* (2019.01)
(52) U.S. Cl.
  CPC ...... *G02F 1/155* (2013.01); *C09K 2211/1425* (2013.01); *C09K 2211/1433* (2013.01); *G02F 2001/164* (2019.01)

(56) References Cited

U.S. PATENT DOCUMENTS

| | | | |
|---|---|---|---|
| 9,891,497 B2 | 2/2018 | Yashiro et al. | |
| 9,932,522 B2 | 4/2018 | Goto et al. | |
| 10,054,834 B2 | 8/2018 | Shinoda et al. | |
| 10,495,937 B2 | 12/2019 | Yashiro et al. | |
| 10,527,905 B2 | 1/2020 | Kaneko et al. | |
| 10,534,236 B2 | 1/2020 | Yamamoto et al. | |
| 10,634,970 B2 | 4/2020 | Goto et al. | |
| 2012/0231363 A1 | 9/2012 | Knuckey et al. | |
| 2016/0005375 A1 | 1/2016 | Naijo et al. | |
| 2016/0209721 A1 | 7/2016 | Matsumoto et al. | |
| 2017/0235203 A1 | 8/2017 | Yamamoto et al. | |
| 2017/0329198 A1 | 11/2017 | Matsuoka et al. | |
| 2017/0329199 A1 | 11/2017 | Yashiro et al. | |
| 2017/0336691 A1 | 11/2017 | Yamamoto et al. | |
| 2018/0044581 A1 | 2/2018 | Sagisaka et al. | |
| 2018/0208834 A1 | 7/2018 | Goto et al. | |
| 2019/0285960 A1 | 9/2019 | Sasa et al. | |
| 2019/0294015 A1* | 9/2019 | Ura | C09K 9/02 |
| 2019/0310530 A1 | 10/2019 | Kaneko et al. | |
| 2019/0324338 A1 | 10/2019 | Takauji et al. | |

FOREIGN PATENT DOCUMENTS

| | | | | |
|---|---|---|---|---|
| JP | 5-25473 A | | 2/1993 | |
| JP | 10-95972 A | | 4/1998 | |
| JP | 2000012882 A | * | 1/2000 | ......... H01L 51/0059 |
| JP | 2005-44791 A | | 2/2005 | |
| JP | 2013-209300 | | 10/2013 | |
| JP | 2016-038572 | | 3/2016 | |
| JP | 2016038572 A | * | 3/2016 | ........... C07C 217/92 |
| WO | 2011/015875 A1 | | 2/2011 | |
| WO | 2017/010360 A1 | | 1/2017 | |

OTHER PUBLICATIONS

Jung-Tsu Wu, et al., "Synthesis, characterization and electrochromic properties of novel redox triarylamine-based aromatic polyethers with methoxy protecting groups", Polymer Chemistry, vol. 10, No. 3, Jan. 15, 2019, XP055832951, 6 pages.

Jiyeong Lee, et al., "Hollow nanotubular toroidal polymer microrings", Nature Chemistry, vol. 6, No. 2, Jan. 5, 2014, XP055832958, 7 pages.

Tsung-Yu Chiang et al: "Functional p-Type, Polymerized Organic Electrode Interlayer in CH 3 NH 3 Pbl 3 Perovskite/Fullerene Planar Heterojunction Hybrid Solar Cells", Applied Materials & Interfaces, vol. 7, No. 44, Oct. 29, 2015 (Oct. 29, 2015), pp. 24973-24981, XP055740140.

Tomas Leijtens et al: "Hole Transport Materials with Low Glass Transition Temperatures and High Solubility for Application in Solid-State Dye-Sensitized Solar Cells", ACS Nano, vol. 6, No. 2, Feb. 28, 2012 (Feb. 28, 2012), pp. 1455-1462, XP055136015.

Park T et al: "A Supramolecular Approach To Lithium Ion Solvation At Nanostructured Dye Sensitised Inorganic/Organic Heterojunctions", Chemical Communications, Royal Society of Chemistry, UK, No. 23, Jan. 1, 2003 (Jan. 1, 2003), p. 2878/2879, XP008041119.

Communication pursuant to Article 94(3) EPC issued Jun. 30, 2023, in corresponding European Patent Application 21161876.4, 7pp.

Indian Office Action issued Feb. 10, 2022, in corresponding Indian Application 202114011426.

* cited by examiner

ELECTROCHROMIC ELEMENT

CROSS-REFERENCE TO RELATED APPLICATIONS

The present application claims priority under 35 U.S.C. § 119 to Japanese Patent Application No. 2020-061281 filed Mar. 30, 2020, and Japanese Patent Application No. 2021-033101 filed Mar. 3, 2021. The contents of which are incorporated herein by reference in their entirety.

BACKGROUND OF THE INVENTION

Field of the Invention

The present disclosure relates to an electrochromic element.

Description of the Related Art

Electrochromic elements, which use coloring and/or decoloring (may be referred to as "coloring and decoloring") of an electrochromic material (electrochromic compound) causing electrochromism, have been researched and developed as a promising candidate for a display device, such as electronic paper, and a light-shielding unit.

Such an electrochromic element includes an electrolyte layer between a pair of electrodes, and an electrochromic layer including an electrochromic compound. When forward voltage or reverse voltage is applied to the electrochromic element, the electrochromic compound is colored or decolored.

In principle, the electrochromic element reversible changes between a colorless state and a colored state. Since the electrochromic element can color in various colors when multiple coloring layers, such as cyan (C), magenta (M), and yellow (Y), are disposed, the electrochromic element is expected as an element that can realize a multicolor display. In order to use the electrochromic element as a transparent display device or a device capable of multicolor display, therefore, the electrochromic compound is desirably a material in a colorless transparent state when it is decolored.

As an electrochromic material that is transparent in a neutral state and colors in an oxidized state, for example, an electrochromic element using a polymer obtained by polymerizing an electrochromic composition including triarylamine (see, for example, Japanese Unexamined Patent Application Publication No. 2016-038572).

Moreover, a polymerizable organic EL material, which is similar to a material used in the present disclosure, is proposed (see, for example, Japanese Unexamined Patent Application Publication No. 2013-209300).

SUMMARY OF THE INVENTION

According to an aspect of the present disclosure, an electrochromic element includes a first electrode, a second electrode to face the first electrode with a gap between the first electrode and the second electrode, an electrolyte layer disposed between the first electrode and the second electrode, and a layer including an electrochromic compound represented by General Formula (1). The layer is disposed on or above the first electrode.

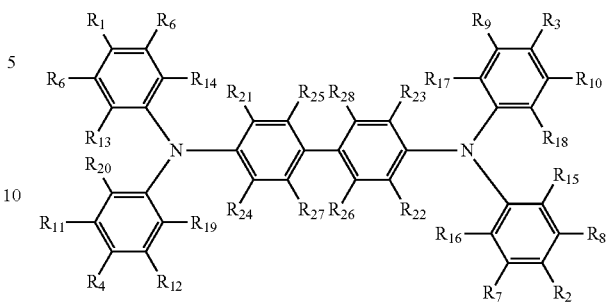

General Formula (1)

In General Formula (1), $R_1$ to $R_4$ are each a monovalent organic group in which no hydrogen atom is present at a benzyl site, where the monovalent organic group may include, as a partial structure, a polymerizable functional group; and $R_5$ to $R_{28}$ are each a hydrogen atom, an alkyl group, or an alkoxy group, where $R_{25}$ and $R_{28}$, or $R_{26}$ and $R_{27}$ may be bonded together to form a structure represented by General Formula (2).

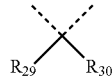

General Formula (2)

In General Formula (2), $R_{29}$ and $R_{30}$ are each an alkyl group, an alkoxy group, or an aryl group, where $R_{29}$ and $R_{30}$ may be bonded via a common bond to form a cyclic structure when $R_{29}$ and $R_{30}$ are both aryl groups.

Figure 1:
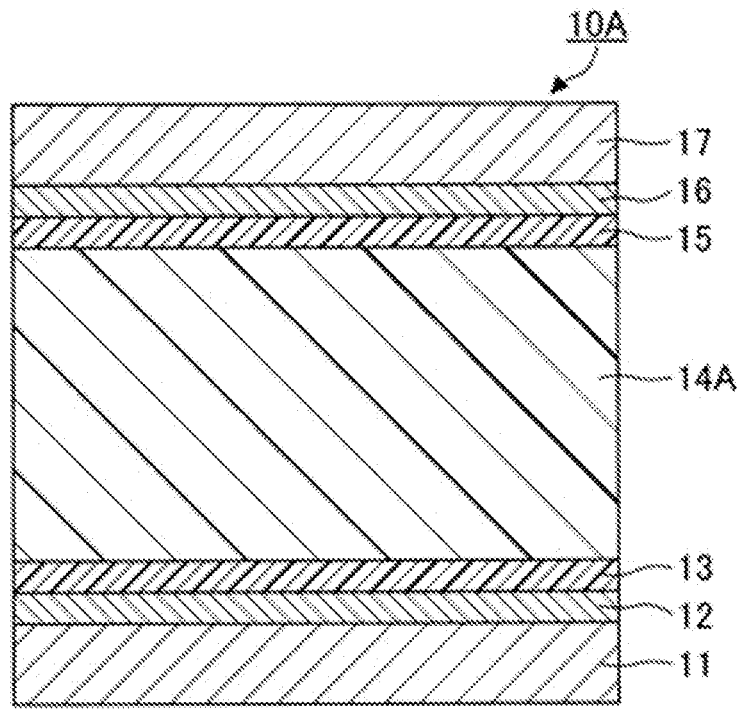
FIG. 1 is a schematic view illustrating one example of the layer structure of the electrochromic element of the first embodiment.

DETAILED DESCRIPTION OF THE INVENTION (Electrochromic Element)

The electrochromic element of the present disclosure includes a first electrode, a second electrode, and an electrolyte layer disposed between the first electrode and the second electrode. The electrochromic element may further include other members according to the necessity.

The electrochromic element may include (1) a layer including the electrochromic compound or electrochromic composition of the present disclosure on or above the first electrode, or (2) the electrolyte layer including the electrochromic compound or electrochromic composition of the present disclosure.

The present disclosure has an object to provide an electrochromic element having excellent durability for repetitive use and photodurability.

The present disclosure can provide an electrochromic element having excellent durability for repetitive use and photodurability.

Japanese Unexamined Patent Application Publication No. 2016-038572 discloses that operations can be performed more stably than the prior art, and photodurability is improved to prevent reduction in light transmittance. However, durability in severe conditions, such as outdoor use, has not been sufficient.

With regard to an electrochromic material having a benzidine skeleton that may include a polymerizable group, Japanese Unexamined Patent Application Publication No. 2013-209300 only discloses use thereof as an organic electroluminescent (EL) material, and does not disclose properties thereof when it is used as an electrochromic material. Moreover, the polymerizable group disclosed in Japanese Unexamined Patent Application Publication No. 2013-209300 is a group that induces ring-opening polymerization, such as an epoxy group and oxetane, and is significantly different from a polymerizable functional group used in the electrochromic compound of the present disclosure.

The present inventors have focused on a specific structure, i.e., a benzidine skeleton that may include a polymerizable group, and have diligently researched on an electrochromic material colors in orange owing to an electrochromic phenomenon. As a result, the present inventors have found that an electrochromic compound having a tetraarylbezidine skeleton where two triaryl amines are linked can solve the above-described problems.

The electrochromic compound of the present disclosure or the electrochromic composition of the present disclosure, which has excellent photodurability and durability against repetitive use, and can satisfy physical properties desirable for an electrochromic element, is used in the electrochromic element at the optimal constitutional position, under optimal constitutional conditions. Therefore, the electrochromic element of the present disclosure has more excellent effects than effects obtained by electrochromic elements of the prior art, especially excellent durability against repetitive use and photodurability.

First, the electrochromic compound of the present disclosure and the electrochromic composition of the present disclosure, both of which are used in the electrochromic element of the present disclosure, will be described.

(Electrochromic Compound)

The electrochromic compound of the present disclosure has a tetraarylbenzidine skeleton in which two triarylamines are linked together.

The electrochromic compound of the present disclosure is an electrochromic compound having a tetraphenylbenzidine skeleton where the nitrogen atoms constituting the tetraarylbenzidine skeleton are substituted with 4 phenyl groups.

The electrochromic compound of the present disclosure is represented by General Formula (1) below, and is preferably a radical polymerizable compound having a tetraarylbenzidine skeleton.

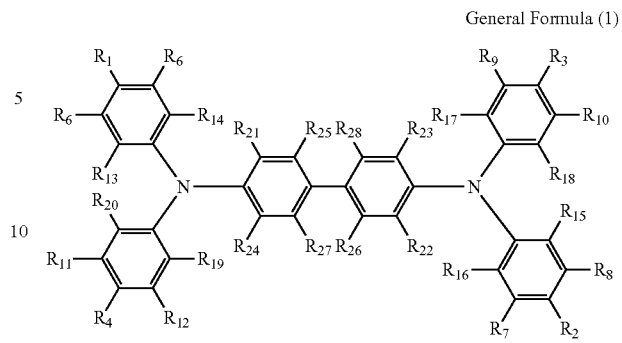

General Formula (1)

In General Formula (1), $R_1$ to $R_4$ are each a monovalent organic group in which no hydrogen atom is present at a benzyl site, where the monovalent organic group may include a polymerizable functional group as a partial structure thereof.

$R_5$ to $R_{28}$ are each a hydrogen atom, an alkyl group, or an alkoxy group, where $R_{25}$ and $R_{28}$, or $R_{26}$ and $R_{27}$ may be bonded together to form a structure represented by General Formula (2) below.

General Formula (2)

In General Formula (2), $R_{29}$ and $R_{30}$ are each an alkyl group, an alkoxy group, or an aryl group, where $R_{29}$ and $R_{30}$ may be bonded via a common bond to form a cyclic structure when $R_{29}$ and $R_{30}$ are both aryl groups.

In General Formula (1), $R_1$ to $R_4$ are each a monovalent organic group in which no hydrogen atom is present at a benzyl site (i.e., not a $CH_2$—X—, where X is an arbitrary monovalent organic group), where the monovalent organic group may include, as a partial structure, a polymerizable functional group.

$R_5$ to $R_{28}$ are each a hydrogen atom, an alkyl group, or an alkoxy group, where $R_{25}$ and $R_{28}$, or $R_{26}$ and $R_{27}$ may be bonded together to form a structure represented by General Formula (2).

One of $R_1$ to $R_{26}$ is a group including a polymerizable functional group.

Examples of the monovalent organic group include a hydroxy group, a nitro group, a cyano group, a carboxyl group, a carbonyl group, an amide group, an aminocarbonyl group, a sulfonic acid group, a sulfonyl group, a sulfone amide group, an aminosulfonyl group, an amino group, an alkyl group, an alkenyl group, an alkynyl group, an aryl group, an alkoxy group, an aryloxy group, an alkylthio group, an arylthio group, a heteroaryl group, and a silyl group. The above-listed groups may have substituents.

Examples of the monovalent organic group having a substituent include: a substituted carboxyl group, such as an alkoxycarbonyl group, an aryloxycarbonyl group, an alkylcarbonyl group, an arylcarbonyl group, a monoalkylaminocarbonyl group, a dialkylaminocarbonyl group, a monoarylaminocarbonyl group, and a diarylaminocarbonyl group; a substituted sulfonyl group, such as an alkoxysulfonyl group, an aryloxysulfonyl group, an alkylsulfonyl group, an arylsulfonyl group, a sulfone amide group, a monoalkylaminosulfonyl group, a dialkylaminosulfonyl group, a monoarylaminosulfonyl group, and a diarylaminosulfonyl group; and a substituted alkylamino group, such as a monoalkylamino group, and a dialkylamino group.

Examples of the substituent of the monovalent organic group include an alkyl group, an alkenyl group, an alkynyl group, an aryl group, an alkoxy group, an aryloxy group, an alkylthio group, an arylthio group, and a heteroaryl group.

Among the above-listed examples, preferable are an alkyl group having one or more carbon atoms, an alkenyl group having 2 or more carbon atoms, an alkynyl group having 2 or more carbon atoms, an aryl group having 6 or more carbon atoms, a heteroaryl group having 2 or more carbon atoms, an alkoxy group, an aryloxy group, and a heteroaryloxy group.

As the alkyl group having one or more carbon atoms, for example, a straight-chain, branched-chain, or cyclic alkyl group having from 1 through 30 carbon atoms is preferable in view of readily availability of raw materials. Among the cyclic alkyl group having from 1 through 30 carbon atoms, a cyclic alkyl group having from 1 through 18 carbon atoms is more preferable.

Examples of the alkyl group having one or more carbon atoms include a methyl group, an ethyl group, a propyl group, a butyl group, a tert-butyl group, an isopropyl group, an isobutyl group, a pentyl group, a hexyl group, a heptyl group, an ethylhexyl group, an octyl group, a decyl group, a dodecyl group, a 2-butyloctyl group, an octadecyl group, a cyclopropyl group, a cyclobutyl group, a cyclopentyl group, a cyclohexyl group, and an adamantyl group.

As the alkenyl group having 2 or more carbon atoms, for example, a straight-chain, branched-chain, or cyclic alkenyl group having from 2 through 30 carbon atoms. Among the cyclic alkenyl group having from 2 through 30 carbon atoms, a cyclic alkenyl group having from 2 through 18 carbon atoms is more preferable.

The alkenyl group having 2 or more carbon atoms is a substituent that is an alkyl group having one or more carbon atoms, from which arbitrary 2 hydrogen atoms are removed. Examples of the alkenyl group having 2 or more carbon atoms include a vinyl group (ethenyl group), a propenyl group, a butenyl group, a pentenyl group, a hexenyl group, a heptanyl group, an octenyl group, a decenyl group, a dodecenyl group, an octadecenyl group, a cyclobutenyl group, a cyclopentenyl group, and a cyclohexenyl group.

As the alkynyl group having 2 or more carbon atoms, for example, a straight-chain, branched-chain, or cyclic alkynyl group having from 2 through 30 carbon atoms is preferable. Among the cyclic alkynyl group having from 2 through 30 carbon atoms, a cyclic alkynyl group having from 2 through 18 carbon atoms is more preferable.

The alkynyl group having 2 or more carbon atoms is a substituent that is an alkyl group having one or more carbon atoms, from which is arbitrary 4 hydrogen atoms are removed. Examples of the alkynyl group having 2 or more carbon atoms include an ethynyl group, a propynyl group, a butynyl group, a pentynyl group, a hexynyl group, a heptynyl group, an octynyl group, a decynyl group, a dodecynyl group, and an octadecynyl group.

Examples of the aryl group having 6 or more carbon atoms include a phenyl group, an o-tolyl group, a m-tolyl group, a p-tolyl group, a p-chlorophenyl group, a p-fluorophenyl group, a p-trifluorophenyl group, a naphthyl group, a biphenyl group, an anthryl group, a phenanthryl group, a pyrenyl group, a fluorenyl group, a benzopyrenyl group, and a chrysenyl group.

As the heteroaryl group having 2 or more carbon atoms, for example, a heteroaryl group having from 2 through 12 carbon atoms is preferable.

Examples of a constitutional element of the heteroaryl group having 2 or more carbon atoms include a nitrogen atom, a sulfur atom, an oxygen atom, a silicon atom, and a selenium atom. It is preferred that the heteroaryl group having 2 or more carbon atoms include at least one selected from the group consisting of a nitrogen atom, a sulfur atom, and an oxygen atom, among the above-listed constitutional elements.

Examples of the heteroaryl group having 2 or more carbon atoms include a monocyclic heteroaryl group, and a polycyclic heteroaryl group.

Examples of the monocyclic heteroaryl group include a pyridine ring, a pyrimidine ring, a pyridazine ring, a pyrazine ring, tetrazine, a thiophene ring, a furan ring, pyrrole, imidazole, pyrazole, a thiazole ring, an oxazole ring, isoxazole, an oxadiazole ring, a triazine ring, a tetrazole ring, and a triazole ring.

Examples of the polycyclic heteroaryl group include a quinolone group, an isoquinoline group, a quinazoline group, a phthalazine group, an indole group, a benzothiophene group, a benzofuran group, a benzoimidazole group, a benzothiodiazole group, an acridine group, a phenoxazine group, a phenothiazine group, a carbazole group, a benzodithiophene group, a benzodifuran group, a dibenzofuran group, and a dibenzothiophene group.

The polycyclic heteroaryl group may be a group where an aryl group and a heteroaryl group are bonded with a covalent bond, or a group where an aryl group and a heteroaryl group are condensed to form a ring together. Examples of the group where an aryl group and a heteroaryl group are bonded with a covalent bond, or the group where an aryl group and a heteroaryl group are condensed to form a ring together include a biphenyl group, a terphenyl group, a 1-phenylnaphthalene group, and a 2-phenylnaphthalene group.

In General Formula (1) above, the polymerizable functional group is not limited as long as the polymerizable functional group is a group that has a carbon double (C═C) bond and is polymerizable. Examples of the polymerizable functional group include a 1-substituted ethylene functional group, 1,1-substituted ethylene functional group presented below.

Examples of the (1) 1-substituted ethylene functional group include a functional group represented by General Formula (i) below.

            General Formula (i)

In General Formula (i), X1 is an arylene group, an alkenylene group, —CO—, —COO—, —CON($R_{100}$)— ($R_{100}$ is a hydrogen atom, an alkyl group, an aralkyl group, or an aryl group), or —S—, where the arylene group or alkenylene group may have a substituent.

Examples of the arylene group include a phenylene group, and a naphthylene group. The phenylene group may have a substituent.

Examples of the alkenylene group include an ethenylene group, a propenylen group, and a butenylene group.

Examples of the alkyl group include a methyl group, and an ethyl group.

Examples of the aralkyl group include a benzyl group, a naphthylmethyl group, and a phenethyl group.

Examples of the aryl group include a phenyl group, and a naphthyl group.

Specific examples of the functional group represented by General Formula (i) include a vinyl group, a styryl group, a 2-methyl-1,3-butadienyl group, a vinylcarbonyl group, an acryloyloxy group, an acryloylamide group, and a vinyl thioether group.

Examples of the (2) 1,1-substituted ethylene functional group include a functional group represented by General Formula (ii) below.

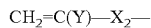  General Formula (ii)

In General Formula (ii), Y is an alkyl group, an aralkyl group, an aryl group, a halogen atom, a cyano group, a nitro group, an alkoxy group, or —$COOR_{101}$ ($R_{101}$ is a hydrogen atom, an alkyl group, an aralkyl group, an aryl group, or $CONR_{102}R_{103}$ [$R_{102}$ and $R_{103}$ are each a hydrogen atom, an alkyl group, an aralkyl group, or an aryl group, where $R_{102}$ and Rios may be identical or different]). The above-listed groups may have a substituent.

Moreover, $X_2$ is a substituent that is same as any of the groups listed as $X_1$ of General Formula (i), or an alkylene group, where at least one of Y and $X_2$ is an oxycarbonyl group, a cyano group, an alkenylene group, or an aromatic ring.

Examples of the alkyl group include a methyl group, and an ethyl group. Examples of the aralkyl group include a benzyl group, a naphthylmethyl group, and a phenethyl group. Examples of the aryl group include a phenyl group, and a naphthyl group. Examples of the alkoxy group include a methoxy group, an ethoxy group, and a group with which an ethylene glycol unit or propylene glycol unit is condensed, such as diethylene glycol, dipropylene glycol, triethylene glycol, tripropyleneglycol, tetraethylene glycol, tetrapropyleneglycol, polyethylene glycol, and polypropylene glycol.

Examples of the halogen atom include a fluorine atom, a chlorine atom, a bromine atom, and an iodine atom.

Specific examples of the polymerizable functional group represented by General Formula (ii) include an α-chloro acryloyloxy group, a methacryloyloxy group, an α-cyano-ethylene group, an α-cyanoacryloyloxy group, an α-cyano-phenylene group, and a methacryloylamino group.

Examples of a substituent further substituting the substituents of $X_1$, $X_2$, and Y include: a halogen atom; a nitro group; a cyano group; an alkyl group, such as a methyl group, and an ethyl group; an alkoxy group, such as a methoxy group, and an ethoxy group; an aryl group, such as a phenyl group, and a naphthyl group; and an aralkyl group, such as a benzyl group, and a phenethyl group.

Among the functional groups represented by General Formula (i) and General Formula (ii) above, a (meth) acryloyl group and a (meth)acryloxy group are particularly preferable, and an acryloyl group or an acryloyloxy group is more preferable, because the above-listed groups beneficially affect properties of a resultant electrochromic element. Specifically, polymerization speed increases due to the presence of the above-listed groups and therefore an electrochromic layer can be completely cured including the inner area of the layer with a short irradiation duration and low irradiation energy, and polymerization-induced phase separation does not tend to occur.

In General Formula (1), the polymerizable functional group is preferably introduced, by substitution, at a terminal of, for example, an alkyl group or alkoxy group having one or more carbon atoms, an aryl group or phenoxy group having 6 or more carbon atoms, or an aryl group having 7 or more carbon atoms substituted with an alkyl group or alkoxy group, in view of resistance to a redox reaction. The polymerizable functional group is more preferably introduced, by substitution, at a terminal of an alkyl group or alkoxy group, particularly preferably an alkoxy group where no hydrogen atom is present at a benzyl site.

The number of carbon atoms of the alkyl group or alkoxy group is preferably 3 or greater.

The polymerizable functional group is preferably bonded to the main skeleton of the electrochromic compound of the present disclosure via at least an alkyl group having 2 or more carbon atoms.

$R_1$ to $R_4$ are each a monovalent organic group in which no hydrogen atom is present at a benzyl site (i.e., not a $CH_2$—X—, where X is an arbitrary monovalent organic group), where the monovalent organic group may include, as a partial structure, a polymerizable functional group.

$R_1$ to $R_4$ are preferably selected from the group consisting of a halogen atom, a monovalent organic group, and a polymerizable functional group. Since a para-site of a nitrogen atom of the triphenylamine skeleton has a high electron density and is reactive, the para-site is preferably substituted with a halogen atom, a monovalent organic group, or a polymerizable functional group, other than a hydrogen atom.

In Japanese Unexamined Patent Application Publication No. 2016-038572 etc., it is disclosed that, when hydrogen atoms are present in para-sites of benzene rings introduced to a nitrogen atom of triphenylamine or benzidine, multimerization of the triphenylamine or benzidine occurs during oxidation and/or reduction to thereby change optical properties of the triphenylamine or benzidine, and therefore the better electrical and optical stability can be obtained by substituting the para-sites with an alkyl group or alkoxy group.

As a result of the researches conducted by the present inventors, it has been found that a compound having a structure substituted with a methyl group as presented below, or a compound having a polymerizable group via an alkyl group has high reactivity of a benzyl-site, and therefore such a compound easily reacts with oxygen. When a supporting electrolyte, a compound to be colored in an oxidized state, and a trace amount of oxygen are present together in a solvent and the solution is irradiated with light (150,000 lux, 15 hours), followed by analyzing the solution by HPLC-MS/MS (available from Thermo scientific), an oxidation reaction of the benzyl site is confirmed even through the compound includes a terminal methyl group or a polymerizable functional group via an alkyl group. The oxidation reaction of the benzyl site occurs probably because the oxidized molecule (i.e. a radical cation state) and a neutral molecule are reacted. Since the result is significant under light irradiation, it is assumed that the molecule that is turned to the radical cation functions as a visible light redox catalyst to accelerate an oxidation reaction.

<Photodegradation (Yellowing)>

It has been confirmed that an absorption wavelength range of a compound obtained as a result of partial oxidation of the benzidine compound is extended up to about 450 nm. Specifically, photodegradation (yellowing) as a result of light irradiation is caused in the following mechanism. Therefore, a research has been carried out to prevent such the mechanism.

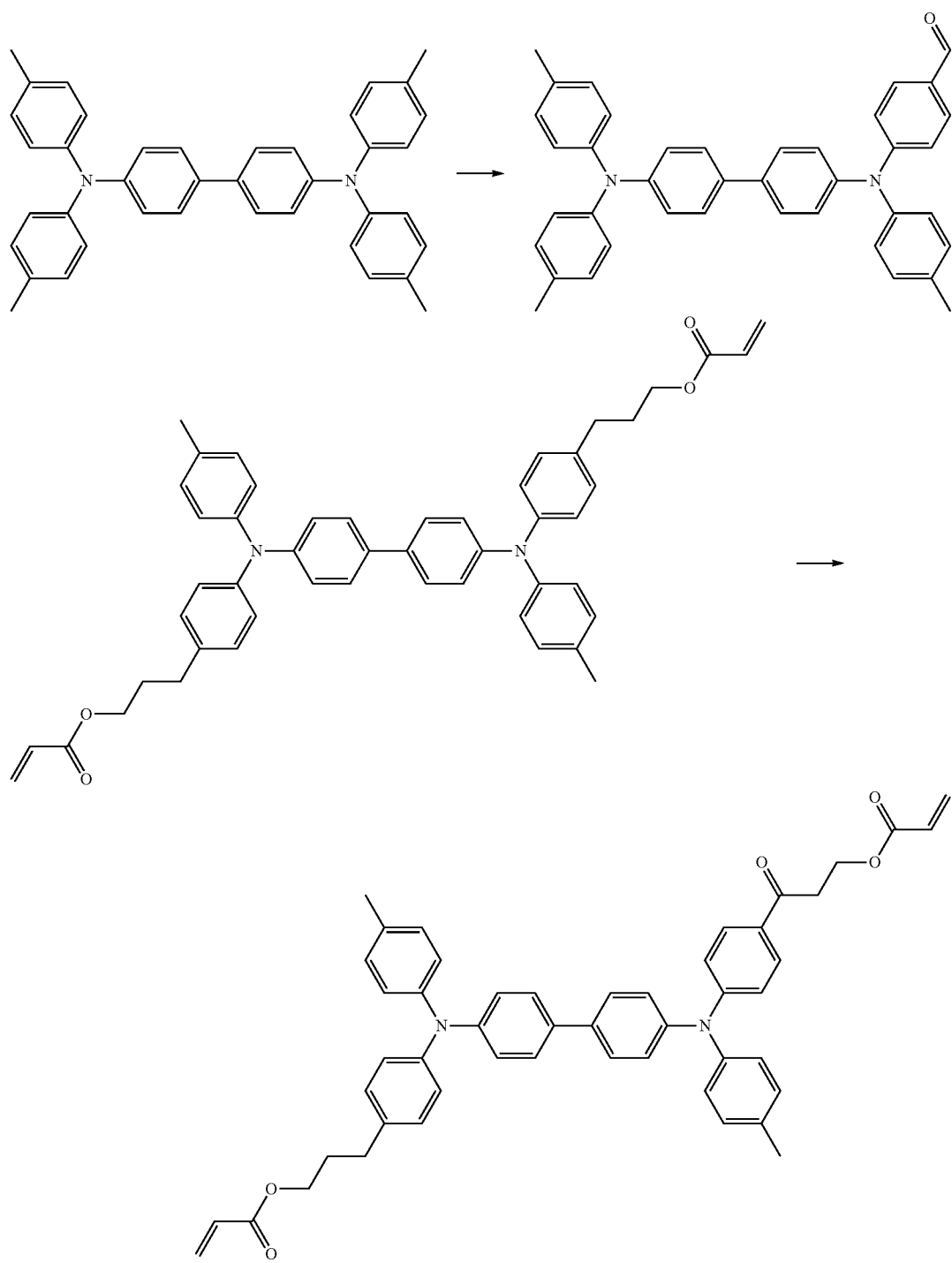

The monovalent organic group in which no hydrogen atom is present at a benzyl site (i.e., not a CH$_2$—X—, where X is an arbitrary monovalent organic group) is a group that is not easily involved with an oxide reaction when bonded at the para-site of the benzidine. Such a group may be obtained by simply inserting an atom other than —CH$_2$—. A group that can be easily oxidized with an appropriate oxidizing agent (e.g., hydrogen peroxide), such as a sulfur atom and a phosphorus atom, is not preferable as the monovalent organic group.

The monovalent organic group is preferably a group that does not have a carbon atom itself, i.e., —Y—X— (where Y is an atom other than a carbon atom), or a group, that is —CZ$_2$—X— (where Z is a monovalent organic group that is other than a hydrogen atom). Y and Z$_2$ are each preferably a group that does not give any electronic influence to the main skeleton of the benzidine, and a strong electron-withdrawing group, such as a halogen atom, a cyano group, and a nitro group, is not preferable as Y or Z$_2$.

The group in which no hydrogen atom is present at a benzyl site is preferably at least one selected from the group consisting of a tert-butyl group, a trialkylsilyl group, a triarylsilyl group, a diallyl monoalkylsilyl group, an alkoxy group, and a phenoxy group.

Among the above-listed substituents, an alkoxy group has the highest electron-donating properties owing to oxygen, and has an effect of significantly decreasing oxidation potential of a benzidine compound. As in the case of the present disclosure, the alkoxy group can prevent yellowing of the benzidine compound itself under light irradiation, and has a preferable effect of reducing driving voltage. However, introduction of the excessive number of the alkoxy groups reduces the oxidation potential excessively, which make the electrochromic compound unstable to oxygen. Therefore, the number of alkoxy groups to be introduced in $R^1$ to $R^4$ is preferably 2 or less. Since the phenoxy group and the alkyl group have substantially the same electron-donating properties to each other, the number of the phenoxy groups or alkyl groups to be introduced is not limited.

In the case where the monovalent organic group in which no hydrogen atom is present at a benzyl site is at least one selected from the group consisting of a tert-butyl group, a trialkylsilyl group, a triarylsilyl group, a diallyl monoalkylsilyl group, an alkoxy group, and a phenoxy group in each of $R^1$ to $R^4$, the number of the alkoxy groups to be introduced in $R^1$ to $R^4$ is preferably from 0 through 2.

It is preferred that at least one of $R_1$ to $R_{28}$ be a polymerizable functional group. In the case where the electrochromic compound of the present disclosure is used as a polymerized film, the polymerizable functional group can impart polymerizability to the electrochromic compound, and a substituent can be easily introduced into the electrochromic compound.

In the case where the polymerizable group is present, any one or both of $R_{29}$, and $R_{30}$, which are generated by bonding $R_1$ to $R_4$, or bonding $R_{25}$ to $R_{28}$, are preferably polymerizable functional groups. The polymerizable functional group is easily introduced without conformational distortion.

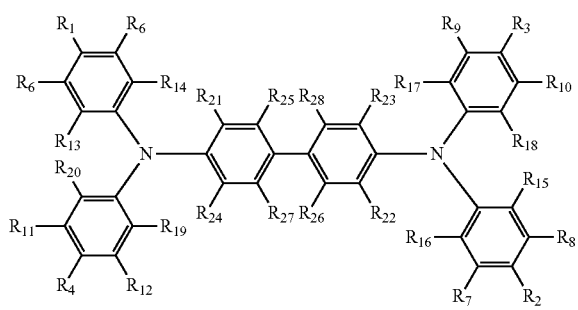

Moreover, $R_5$ to $R_{12}$ are each preferably an alkyl group, an alkoxy group, an aryl group, an aryloxy group, a halogen atom, and a polymerizable functional group in order to prevent a color tone change and prevent a side reaction generated between molecules during coloring.

When $R_1$ to $R_{12}$ are each a monovalent organic group, the monovalent organic group is preferably an alkyl group having one or more carbon atoms, an alkenyl group having 2 or more carbon atoms, an alkynyl group having 2 or more carbon atoms, an aryl group having 6 or more carbon atoms, a heteroaryl group having 2 or more carbon atoms, an alkoxy group having one or more carbon atoms, an aryloxy group, or a heteroaryloxy group.

$R_1$ to $R_{12}$ may be each a group where one or more aryl groups or heteroaryl group groups are bonded together with a covalent bond, or a group where one or more aryl groups or heteroaryl group groups are condensed to form a ring together. The group where one or more aryl groups or heteroaryl group groups are bonded together with a covalent bond, or the group where one or more aryl groups or heteroaryl group groups are condensed to form a ring together may be a group that has from 1 through 100 carbon atoms in total, and may include a hetero atom. The upper limit of the total number of carbon atoms is preferably 50, and more preferably 36. Examples of the hetero atom include an oxygen atom, a sulfur atom, and a nitrogen atom.

In view of transparency when the electrochromic compound is decolored, an absorption edge of the group itself is preferably 400 nm or less, and more preferably 380 nm or less. The group is the group where one or more aryl groups or heteroaryl group groups are bonded together with a covalent bond, or the group where one or more aryl groups or heteroaryl group groups are condensed to form a ring together.

The number of groups each obtained by bonding an aryl group and a heteroaryl group with a covalent bond, or groups each obtained by bonding an aryl group and a heteroaryl group to form a condensed ring, is preferably selected from the range of 1 to 6. The number thereof is preferably from 1 through 3, and more preferably from 1 through 2. An increase in the number of groups each obtained by bonding an aryl group and a heteroaryl group with a covalent bond, or groups each obtained by bonding an aryl group and a heteroaryl group to form a condensed ring, which do not contribute to coloring, in the triphenylamine belong to a chromophore is not preferable in view of coloring efficiency and cost of materials.

$R_{13}$ to $R_{28}$ are each preferably at least one selected from the group consisting of a hydrogen atom, a halogen atom, a monovalent organic group, and a polymerizable functional group, as $R_{13}$ to $R_{28}$ are each preferably substituted with a halogen atom, a monovalent organic group, or a polymerizable functional group. $R_{10}$ to $R_{15}$ are each more preferably an alkyl group, an alkoxy group, an aryl group, a heteroaryl group, a halogen atom, or a polymerizable functional group, and particularly preferably an alkyl group, an alkoxy group, an aryl group, or a polymerizable functional group. The polymerizable functional group is preferably present in a part of, particularly preferably a terminal of, an alkyl group or an aryl group.

Second Preferable Embodiment $R_{13}$ to $R_{24}$ are preferably all hydrogen atoms. This is because conformational distortion of the phenyl groups bonded to the nitrogen atoms of the benzidine does not occur because a substituent is not present as $R_{13}$ to $R_{24}$. Moreover, a halogen atom, which has a small atom size, does not cause conformational distortion, but the halogen atom is not preferable because the halogen atom has high electron-withdrawing properties to increase oxidation potential of the benzidine compound.

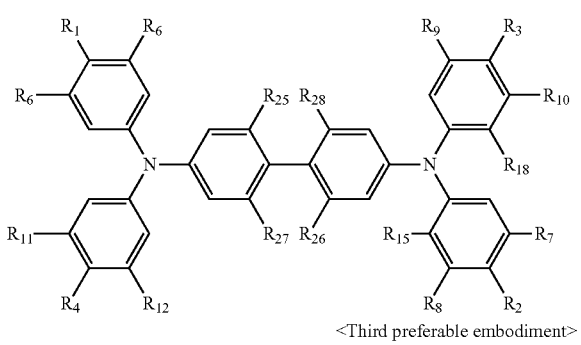

<Third preferable embodiment>

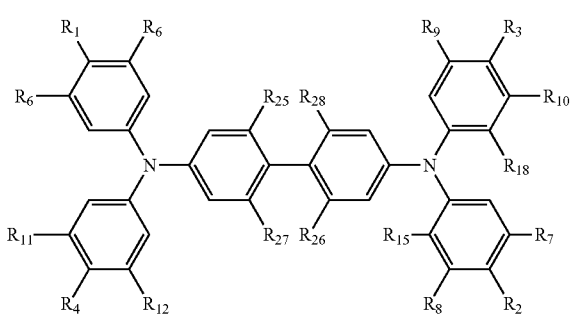

In the general formula above, $R_{25}$ to $R_{28}$ are preferably each a halogen atom or a hydrogen atom, or are preferably bonded together to form a structure represented by General Formula (2), a cyclic ether structure (e.g., dibenzofuran) via an oxygen atom, or a structure (e.g., dibenzothiophene) via a sulfur atom, and $R_{25}$ to $R_{28}$ are more preferably each a hydrogen atom or form a structure represented by General Formula (2).

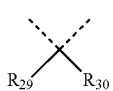

General Formula (2)

In General Formula (2), $R_{29}$ and $R_{30}$ are each an alkyl group, an alkoxy group, or an aryl group, where $R_{29}$ and $R_{30}$ may be bonded via a common bond to form a cyclic structure when $R_{29}$ and $R_{30}$ are both aryl groups.

Examples of the electrochromic compound represented by General Formula (1) include Exemplary Compounds below. The electrochromic compound of the present disclosure is not limited to Exemplary Compounds below. In Exemplary Compounds below, MeO— represents a methoxy group.

<Exemplary Compound 1>

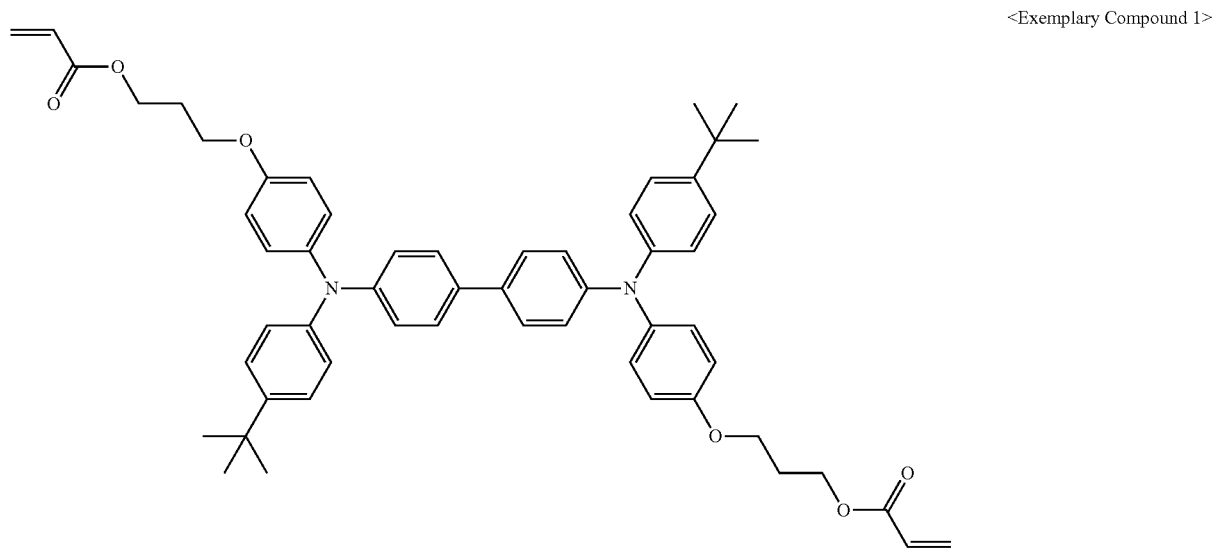

<Exemplary Compound 2>
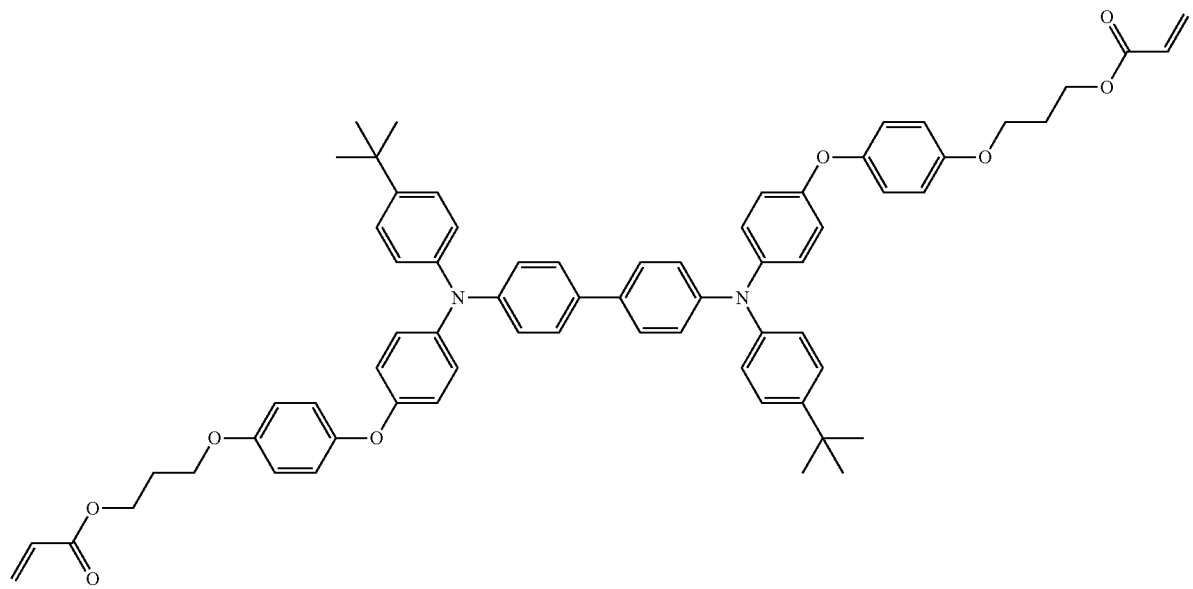
<Exemplary Compound 3>
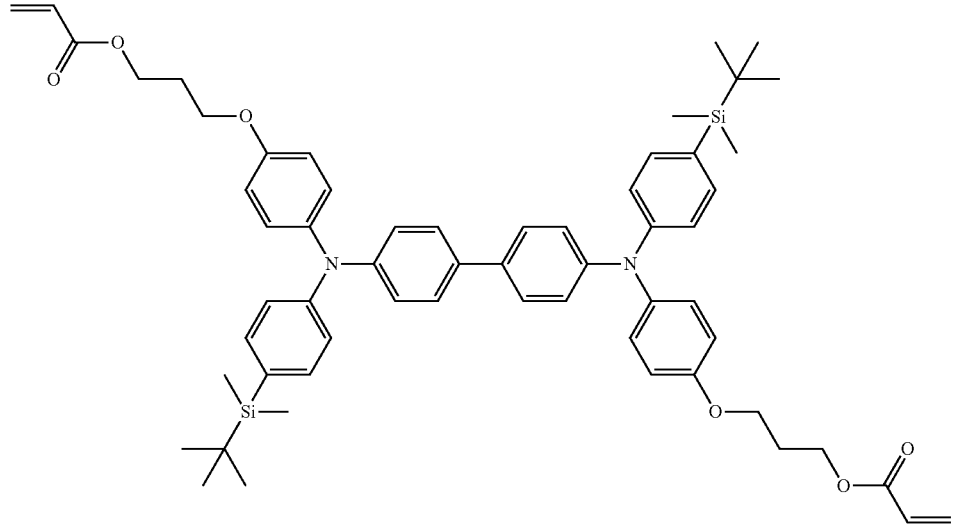

-continued
<Exemplary Compound 4>
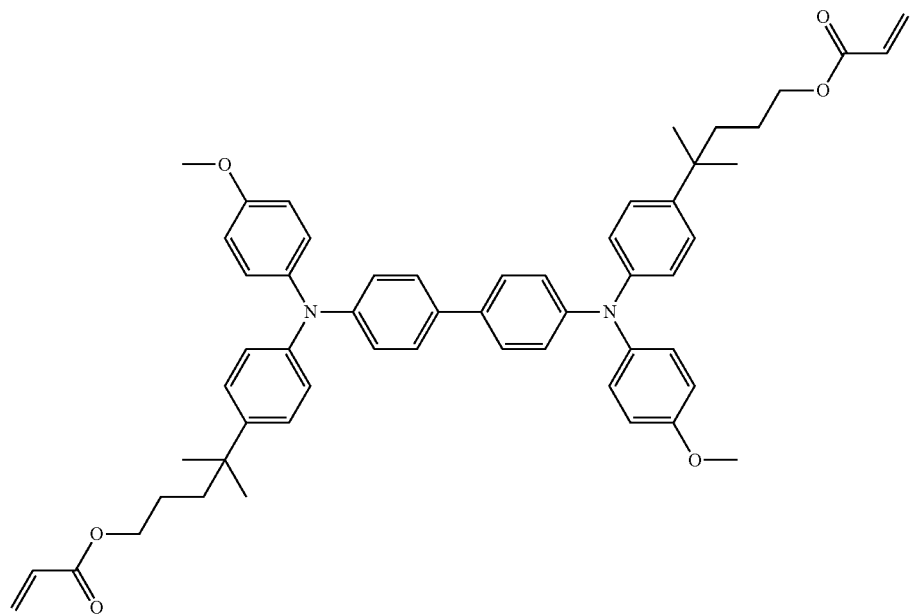
<Exemplary Compound 5>
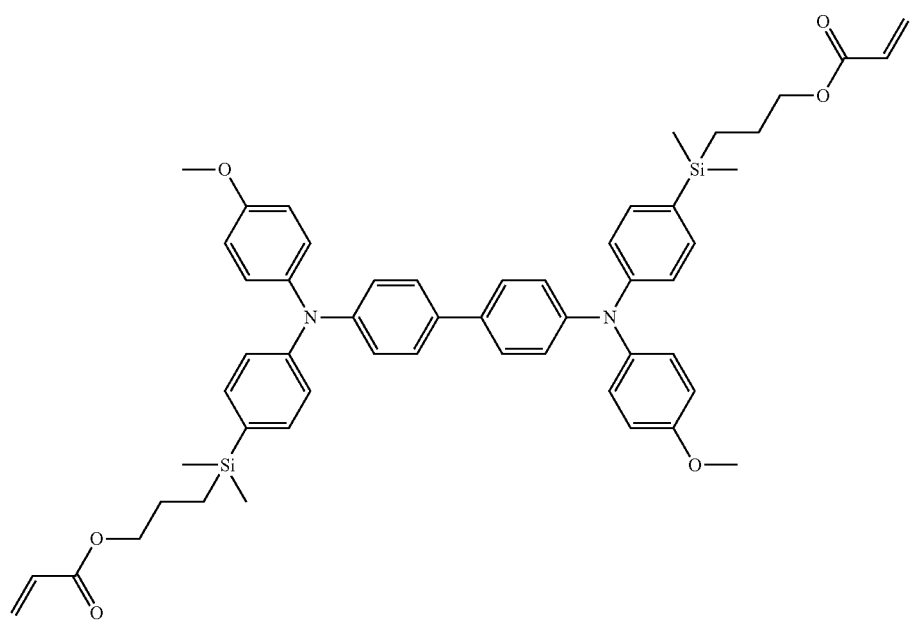

<Exemplary Compound 6>
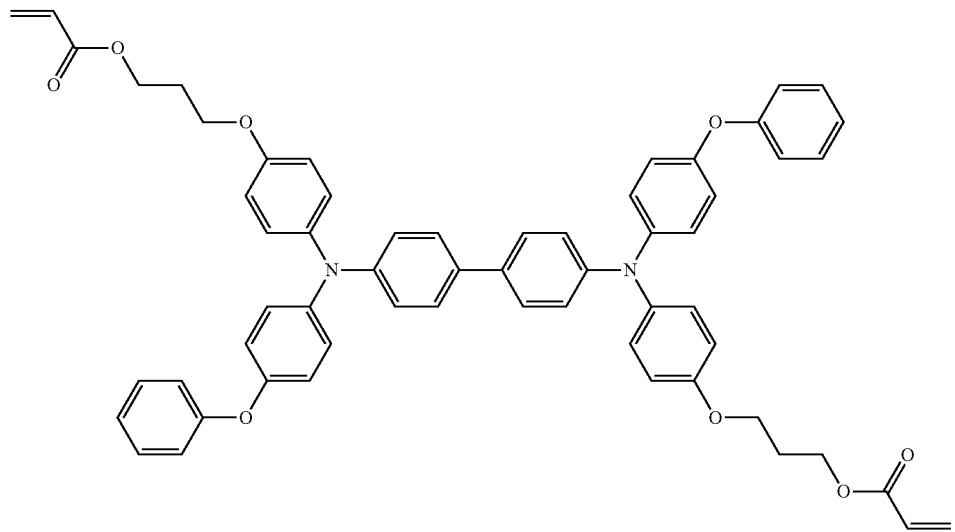
<Exemplary Compound 7>
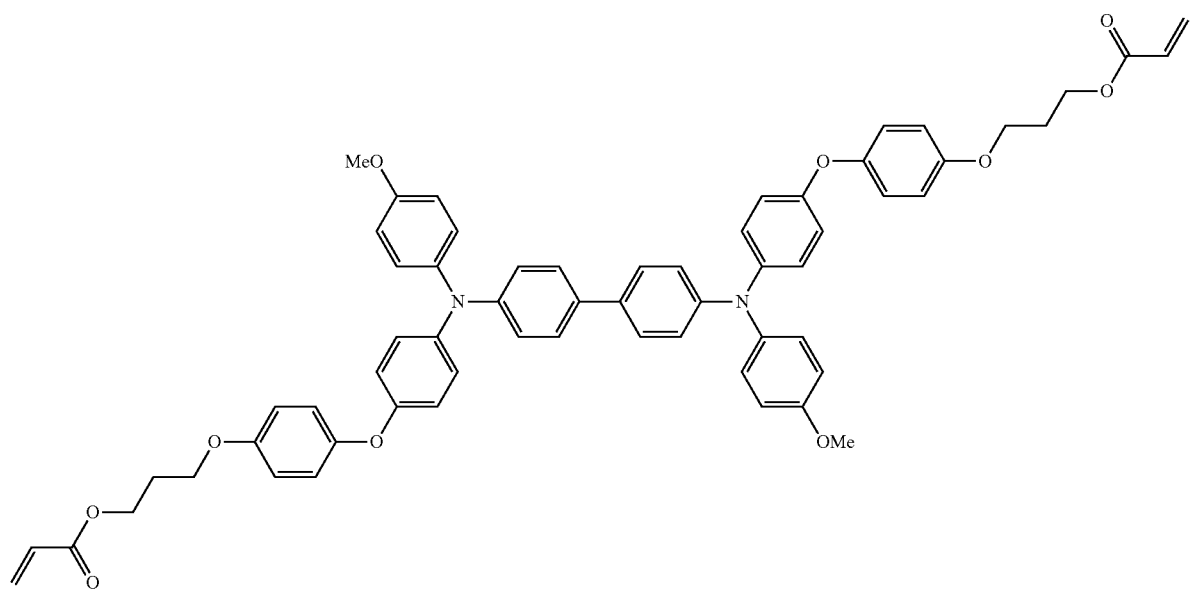
<Exemplary Compound 8>
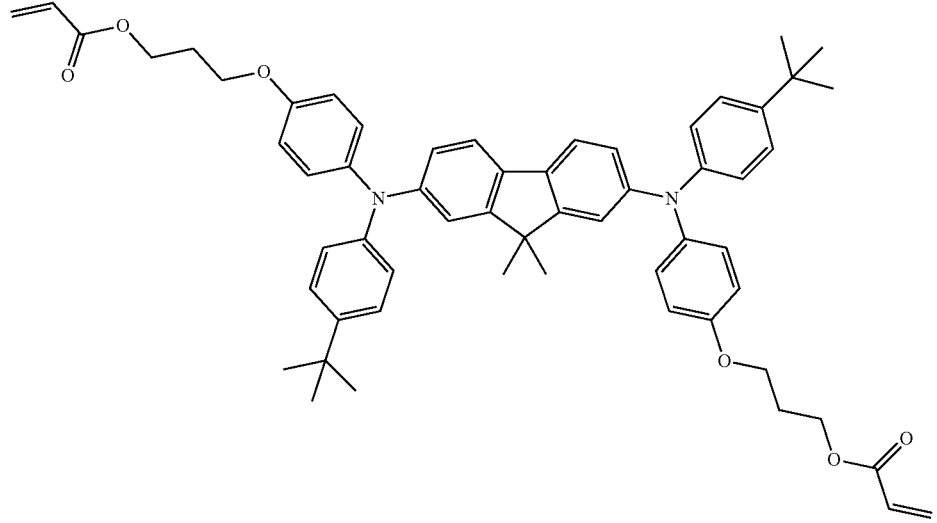

<Exemplary Compound 9>
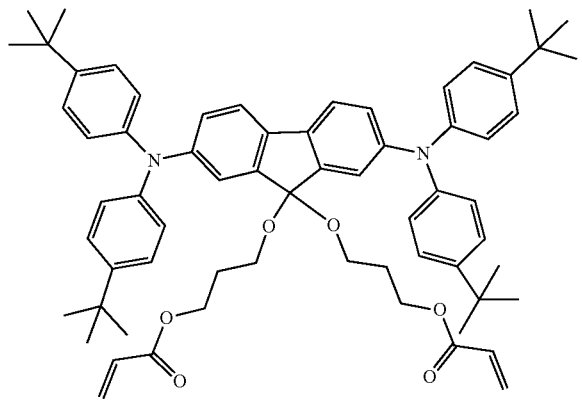
<Exemplary Compound 10>
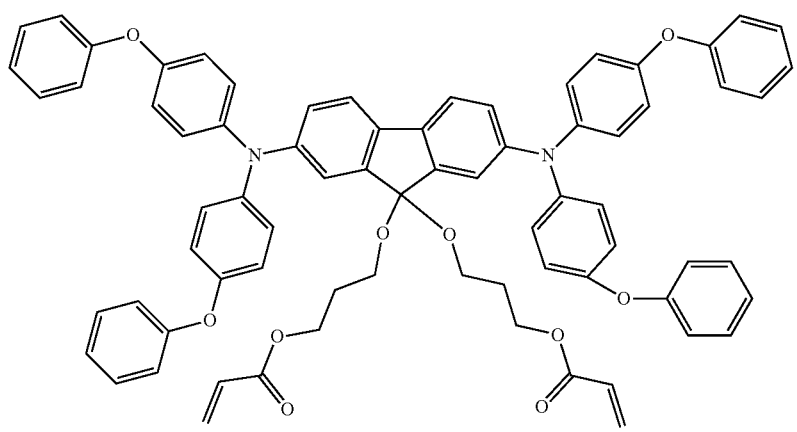
<Exemplary Compound M1>
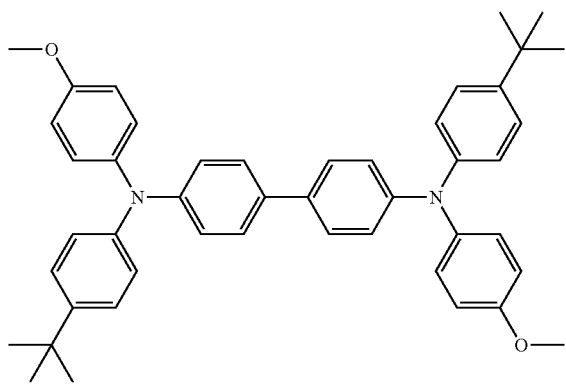
<Exemplary Compound M2>
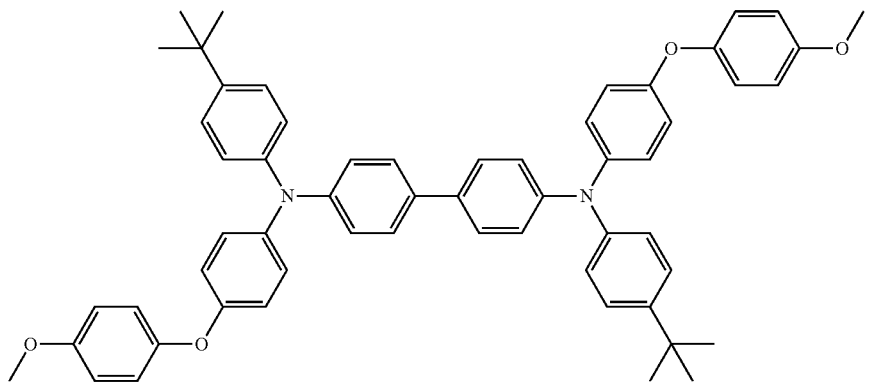

<Exemplary Compound M3>

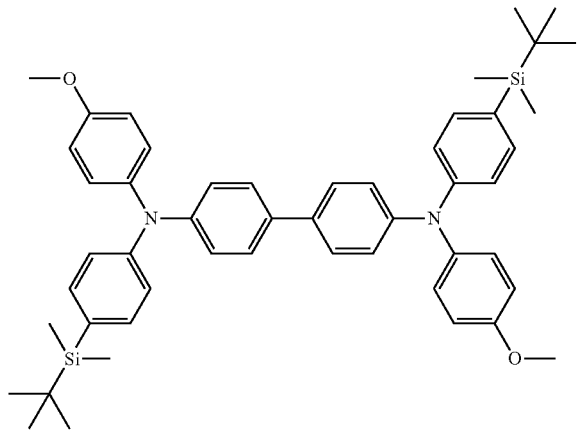

<Exemplary Compound M4>

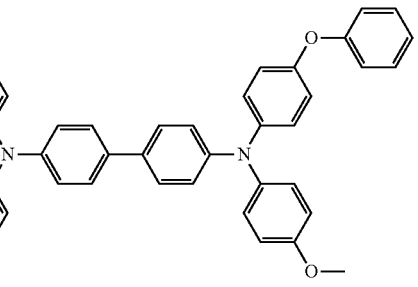

<Exemplary Compound M5>

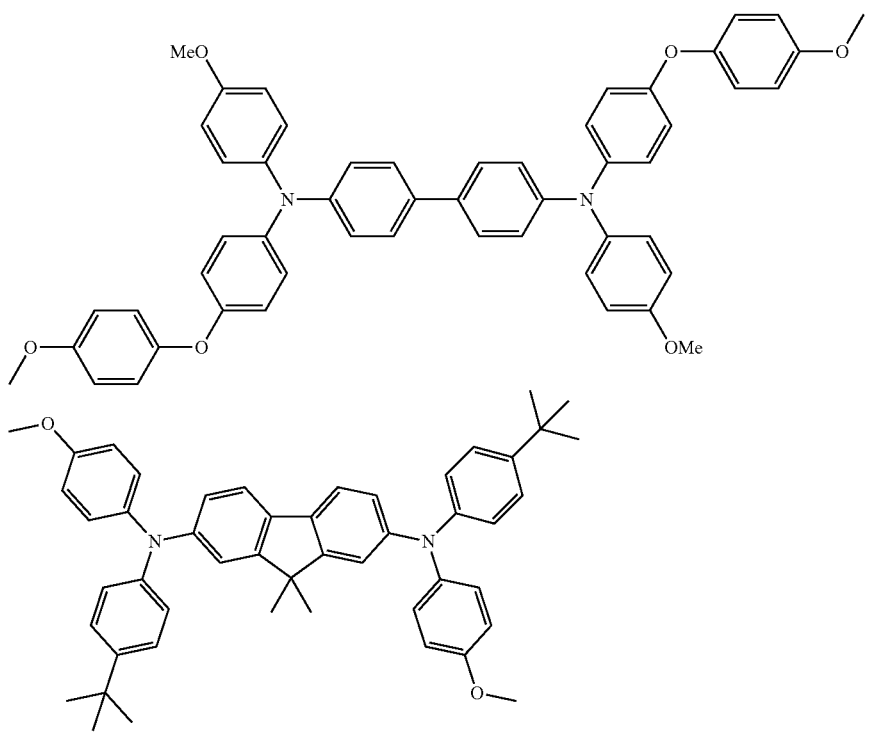

(Electrochromic Composition)

The electrochromic composition of the present disclosure includes the electrochromic compound of the present disclosure. The electrochromic composition preferably further include another radical polymerizable compound.

The electrochromic compound of the present disclosure is a radical polymerizable compound having a tetraarylbenzidine skeleton. Therefore, the electrochromic compound of the present disclosure plays important role for imparting an electrochromic function having a redox reaction at a surface of the first electrode of the electrochromic element.

The electrochromic composition of the present disclosure preferably further includes one or more radical polymerizable compounds that are different from the electrochromic compound of the present disclosure.

<Triphenylamine Compound>

The electrochromic composition of the present disclosure may further include a triphenylamine compound as the above-mentioned another radical polymerizable compound. Since the electrochromic composition of the present disclosure includes a triphenylamine compound, the electrochromic composition is transparent in a neutral state, and can exhibit stable optical properties (typically a color obtained by mixing orange and blue) in the one-electron-oxidized state.

The para-sites of the 3 phenyl groups bonded to the nitrogen atom of the triphenylamine compound are preferably substituted with a substituent other than a hydrogen atom, such as an alkyl group, an alkoxy group, and a radical polymerizable substituent. The triphenylamine compound having hydrogen atoms at the terminals may be reacted and multimerized in the one-electron-oxidized state. It has been known that, when the triphenylamine compound is multimerized, the triphenylamine compound becomes a benzidine compound, and the color thereof is changed from blue to orange. When the para-sites of the 3 phenyl groups bonded to the nitrogen atom of the triphenylbenzidine compound are substituted with substituents other than hydrogen atoms, electrochemical stability is improved. Since multimerization of the triphenylamine compound in the one-electron-oxidized state can be prevented, stable optical properties, such as prevention of color change during coloring, can be exhibited.

Moreover, the ortho site of the benzene constituting the triphenylamine is preferably bonded via a spacer, where the nitrogen atom bonded to the benzene is determined as an ipso site of the benzene. Examples of the spacer include a carbon atom, and a silicon atom, which may be substituted with an alkyl group or an aryl group. Such crosslinkable triphenylamine is expected to improve electrochemical durability further because the reactive ortho site, which is reactive to the para-site, is blocked.

The triphenylamine compound may be used as it is, or may be copolymerized for use. Therefore, the triphenylamine compound may include a radical polymerizable substituent. The radical polymerizable substituent may be appropriately selected in the same manner as the selection of the radical polymerizal substituent of the electrochromic compound of the present disclosure. The radical polymerizable substituent may be present as a part of the tetraphenylbenzidine, such as a terminal of an alkyl group or alkoxy group present in the para-site. The radical polymerizable substituent is more preferably an acryloyloxy group, or a methacryloyloxy group, and more preferably an acryloyloxy group.

The triphenylamine compound in the neutral state is preferably transparent in the visible range, i.e., the absorption edge of the ultraviolet visible absorption spectrum thereof is 420 nm or shorter, more preferably 410 nm or shorter, and even more particularly 400 nm or shorter. In addition, the triphenylamine compound in the one-electron oxidized state colors blue or cyan, that is, the peak wavelength thereof in the visible region (i.e., from 380 nm through 780 nm) is preferably in the approximate region of from 550 nm to 700 nm, and the absorption edge of the short wavelength side thereof is preferably from 450 nm through 500 nm. The absorption edge of the long wavelength side thereof is preferably from 650 nm through 800 nm. When the triphenylamine compound is combined with the electrochromic compound of the present disclosure that colors in orange, coloring of black is realized as the absorption of the triphenylamine compound and the absorption of the electrochromic compound complementarily cover the entire visible range.

Specific exemplary compounds of the triphenylamine compound that can satisfy the above-described optical properties include Exemplary Compound below. However. The triphenylamine compound is not limited to Exemplary Compound below. In Exemplary Compounds below, MeO— represents a methoxy group.

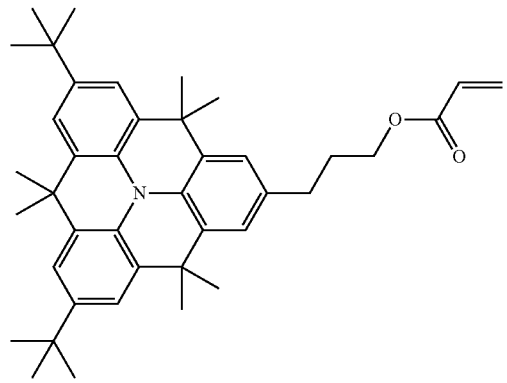

<Exemplary Compound TPA1>

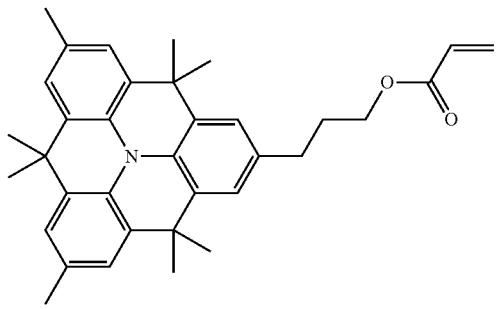

<Exemplary Compound TPA2>

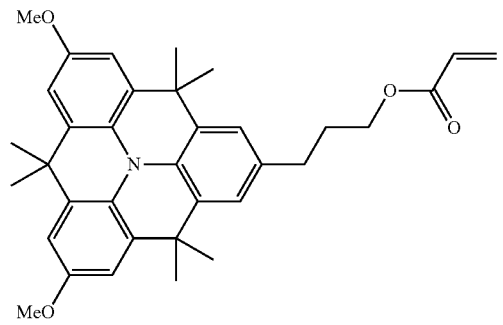

<Exemplary Compound TPA3>

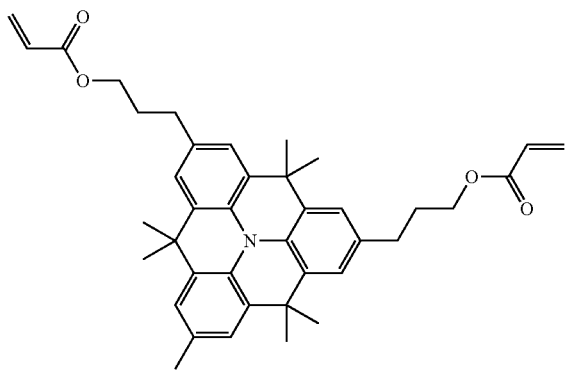

<Exemplary Compound TPA4>

-continued
<Exemplary Compound TPA5>
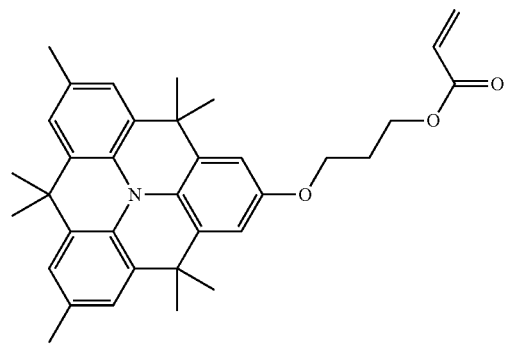
<Exemplary Compound TPA6>
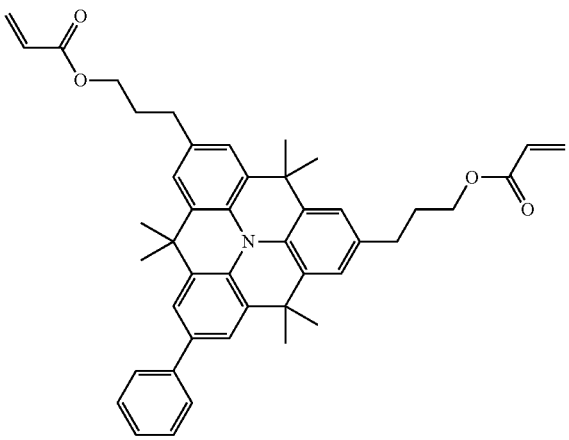
<Exemplary Compound TPA7>
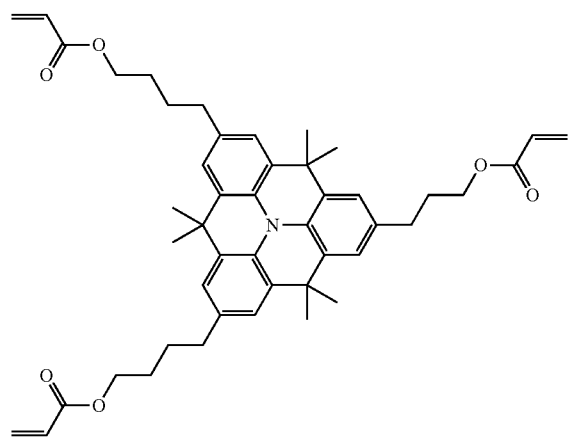
<Exemplary Compound TPA8>
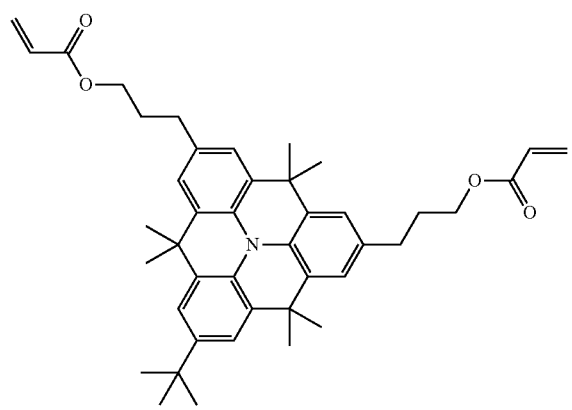
<Exemplary Compound TPA9>
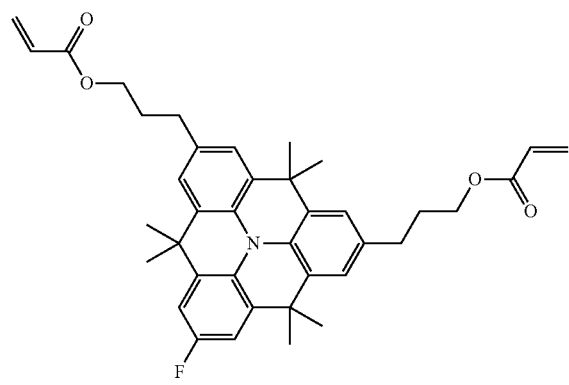
<Exemplary Compound TPA10>
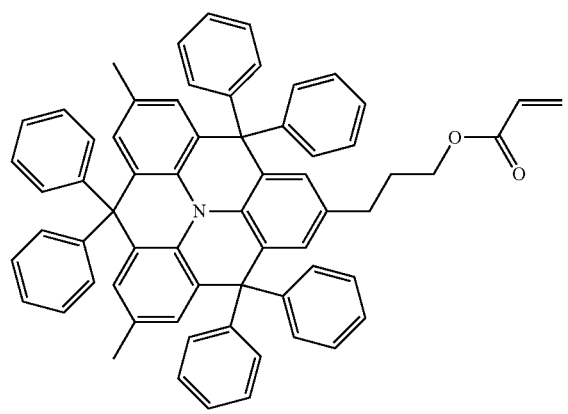

-continued
<Exemplary Compound TPA11>
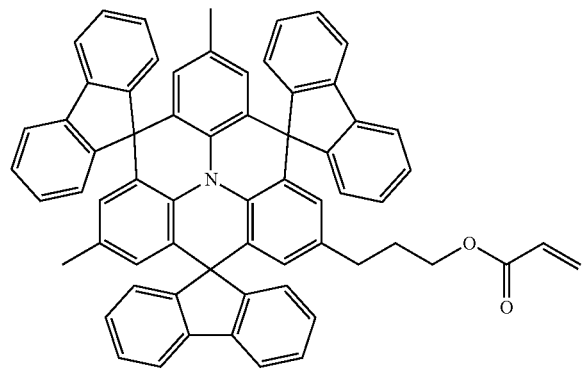
<Exemplary Compound TPA12>
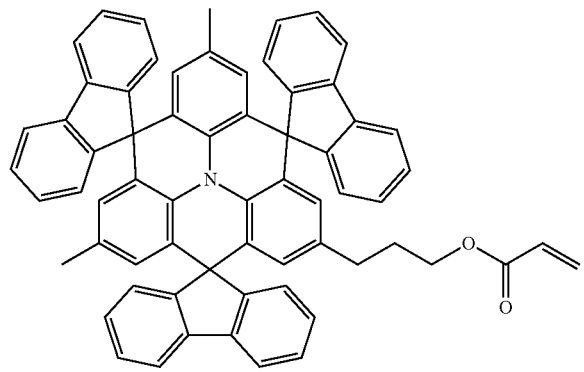
<Exemplary Compound TPA13>
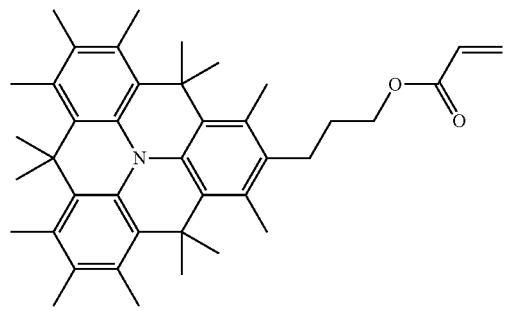
<Exemplary Compound TPA14>
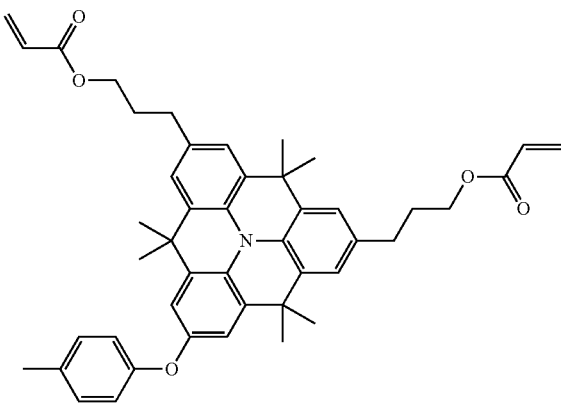
<Exemplary Compound TPA15>
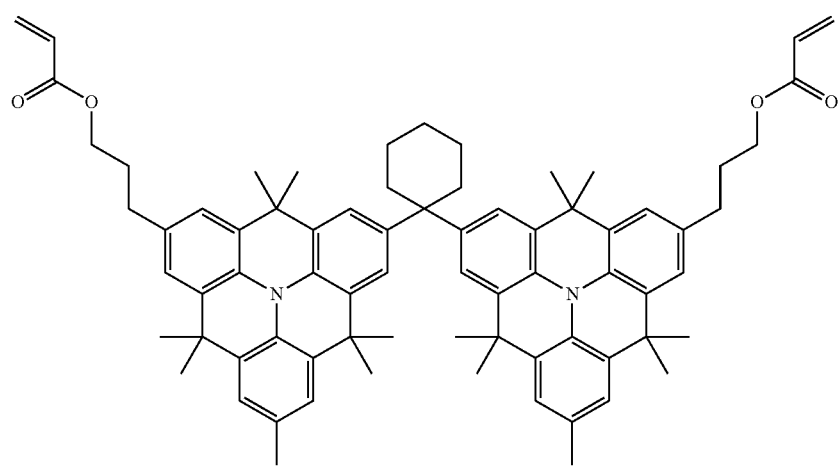

-continued
<Exemplary Compound TPA16>
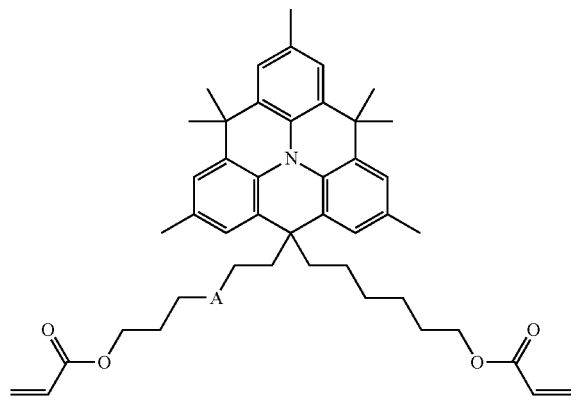
<Exemplary Compound TPA17>
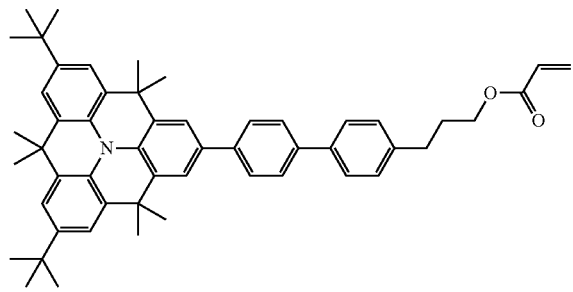
<Exemplary Compound TPA18>
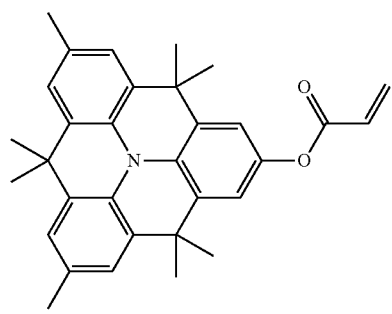
<Exemplary Compound TPA19>
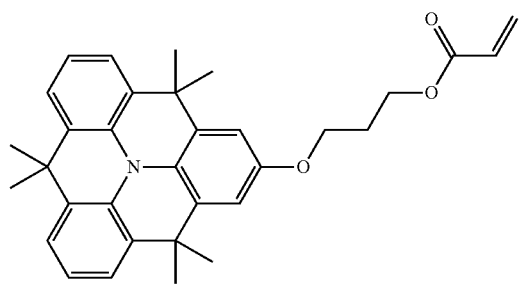
<Exemplary Compound TPA20>
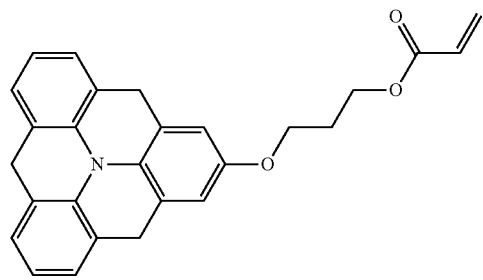
<Exemplary Compound TPA21>
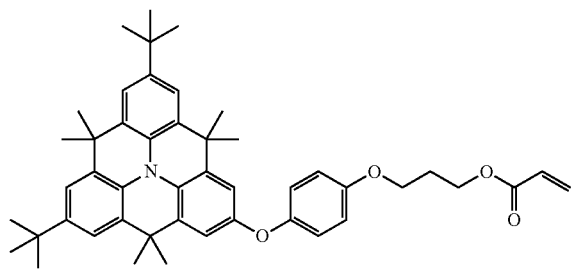
<Exemplary Compound TPA22>
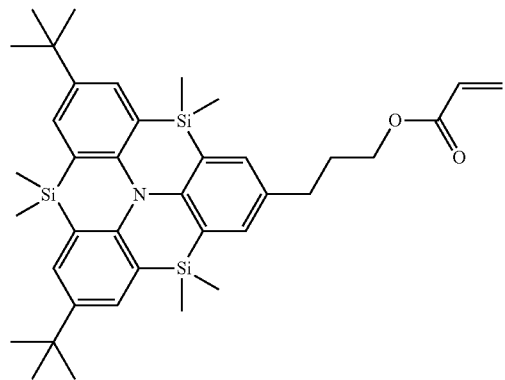
<Exemplary Compound TPA23>
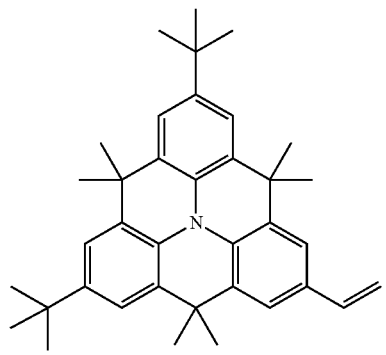

<Exemplary Compound TPAM1>
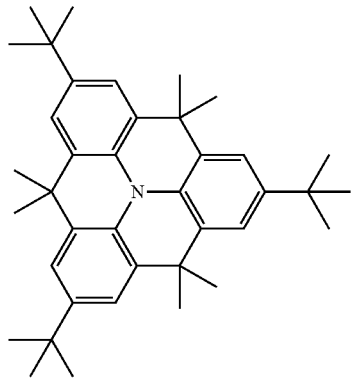
<Exemplary Compound TPAM2>
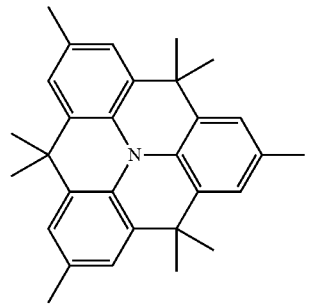
<Exemplary Compound TPAM3>
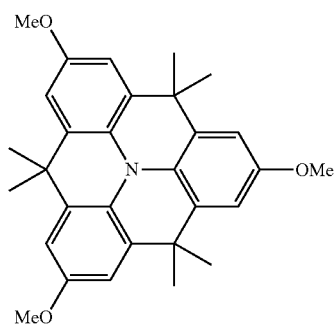
<Exemplary Compound TPAM4>
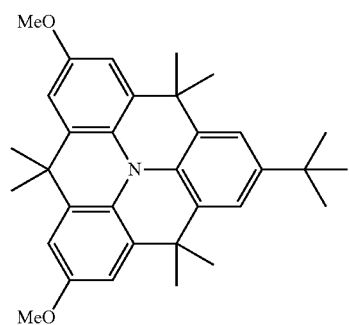
<Exemplary Compound TPAM5>
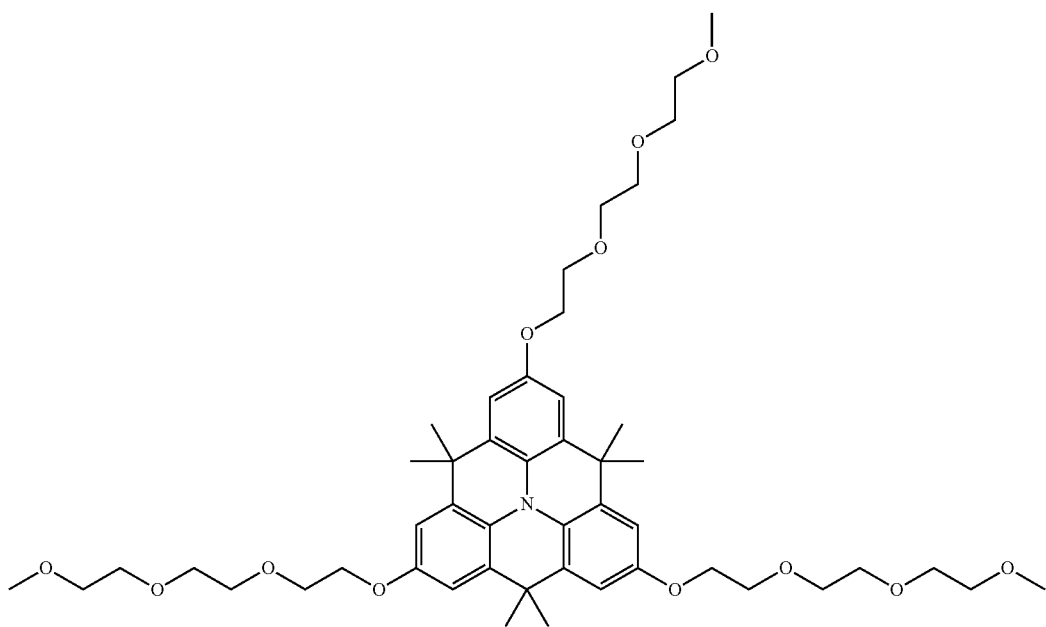

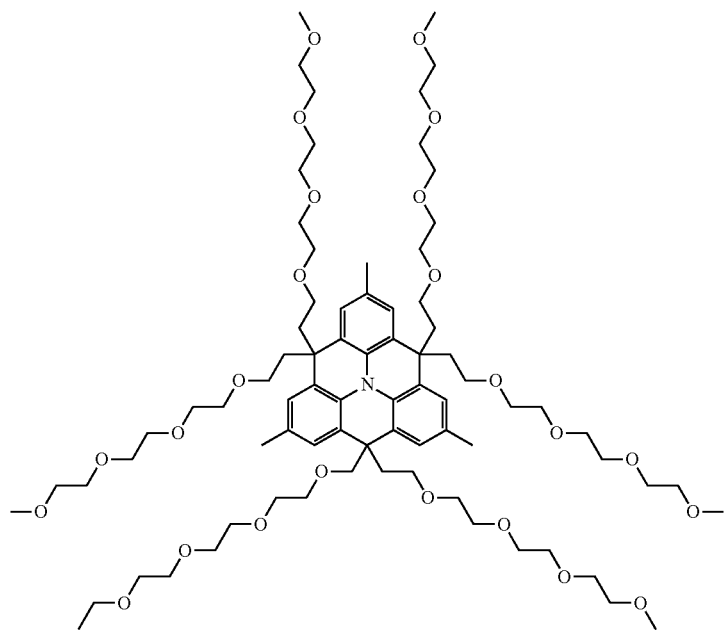
<Exemplary Compound TPAM6>
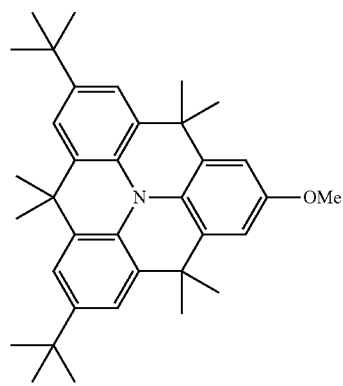
<Exemplary Compound TPAM7>
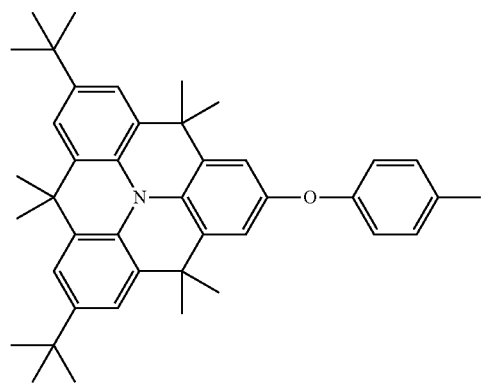
<Exemplary Compound TPAM8>
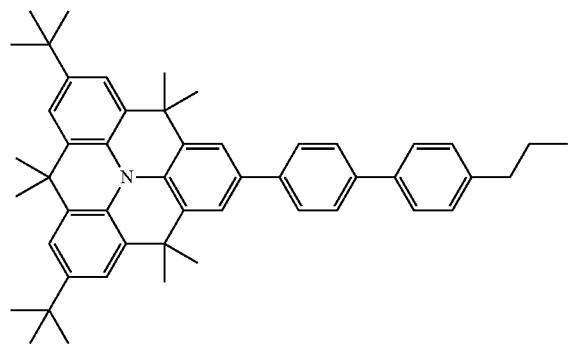
<Exemplary Compound TPAM9>
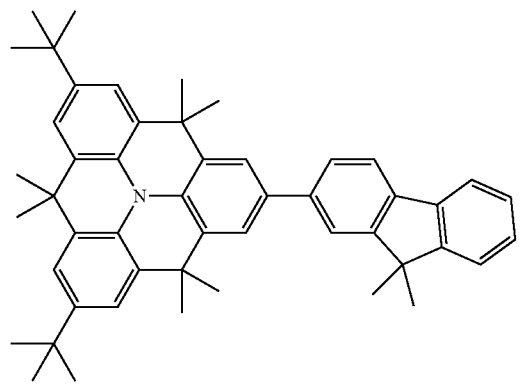
<Exemplary Compound TPAM10>

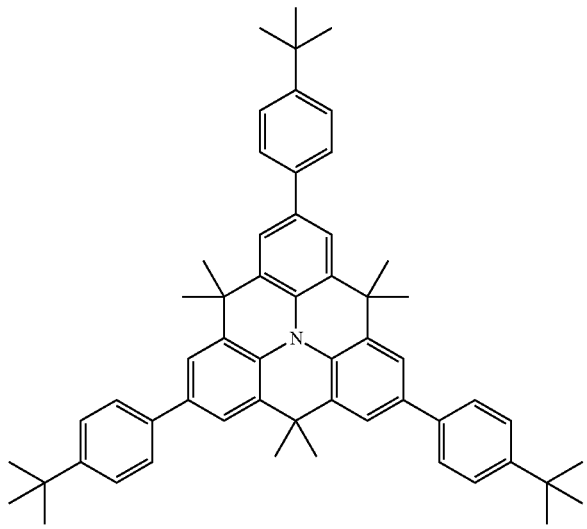

<Exemplary Compound TPAM11>

Examples of the above-mentioned other radical polymerizable compounds excluding the electrochromic compound of the present disclosure and the triphenylamine compound include a monofunctional radical polymerizable compound, a bifunctional radical polymerizable compound, a trifunctional or higher radical polymerizable compound, a functional monomer, and a radical polymerizable oligomer. Among the above-listed examples, a bifunctional or higher radical polymerizable compound is particularly preferable. Examples of the radical polymerizable functional group in any of the above-listed other radical polymerizable compounds are identical to any of the examples listed as the radical polymerizable functional group of the electrochromic compound of the present embodiment. Among the above-listed examples, an acryloyloxy group and a methacryloyloxy group are particularly preferable, and an acryloyloxy group is more preferable.

Examples of the monofunctional radical polymerizable compound include 2-(2-ethoxyethoxy)ethylacrylate, methoxy polyethylene glycol monoacrylate, methoxy polyethylene glycol monomethacrylate, phenoxy polyethylene glycol acrylate, 2-acryloyloxyethylsuccinate, 2-ethylhexylacrylate, 2-hydroxyethylacrylate, 2-hydroxypropylacrylate, tetrahydrofurfuryl acrylate, 2-ethylhexylcarbitol acrylate, 3-methoxybutyl acrylate, benzyl acrylate, cyclohexyl acrylate, isoamyl acrylate, isobutyl acrylate, methoxy triethylene glycol acrylate, phenoxy tetraethylene glycol acrylate, cetyl acrylate, isostearyl acrylate, stearyl acrylate, and a styrene monomer. The above-listed examples may be used alone or in combination.

Examples of the bifunctional radical polymerizable compound include 1,3-butanediol diacrylate, 1,4-butanediol diacrylate, 1,4-butanediol dimethacrylate, 1,6-hexanediol diacrylate, 1,6-hexanediol dimethacrylate, diethylene glycol diacrylate, polyethylene glycol diacrylate, neopentyl glycol diacrylate, EO-modified bisphenol A diacrylate, EO-modified bisphenol F diacrylate, and neopentyl glycol diacrylate. The above-listed examples may be used alone or in combination.

Examples of the trifunctional or higher radical polymerizable compound include trimethylolpropane triacrylate (TMPTA), trimethylolpropane trimethacrylate, EO-modified trimethylolpropane triacrylate, PO-modified trimethylolpropane triacrylate, caprolactone-modified trimethylolpropane triacrylate, HPA-modified trimethylolpropane trimethacrylate, pentaerythritol triacrylate, pentaerythritol tetraacrylate (PETTA), glycerol triacrylate, ECH-modified glycerol triacrylate, EO-modified glycerol triacrylate, PO-modified glycerol triacrylate, tris(acryloxyethyl) isocyanurate, dipentaerythritol hexaacrylate (DPHA), caprolactone-modified dipentaerythritol hexaacrylate, dipentaerythritol hydroxypentaacrylate, alkyl-modified dipentaerythritol pentaacrylate, alkyl-modified dipentaerythritol tetraacrylate, alkyl-modified dipentaerythritol triacrylate, dimethylolpropane tetraacrylate (DTMPTA), pentaerythritol ethoxytetraacrylate, EO-modified phosphoric acid triacrylate, and 2,2,5,5-tetrahydroxymethylcyclopentanone tetraacrylate. The above-listed examples may be used alone or in combination. In the present specification, the term "EO-modified" means ethyleneoxy-modified, and the term "PO-modified" means propyleneoxy-modified.

Examples of the functional monomer include: a monomer substituted with a fluorine atom, such as octafluoropentyl acrylate, 2-perfluorooctylethylacrylate, 2-perfluorooctylethylmethacrylate, and 2-perfluoroisononylethylacrylate; vinyl monomers including a polysiloxane group having from 20 through 70 repeating units of siloxane, such as acryloyl polydimethylsiloxane ethyl, methacryloyl polydimethylsiloxane ethyl, acryloyl polydimethylsiloxane propyl, acryloyl polydimethylsiloxane butyl, and diacryloyl polydimethylsiloxane diethyl, disclosed in Japanese Examined Application Publication Nos. 05-60503 and 06-45770; acrylate; and methacrylate. The above-listed examples may be used alone or in combination.

Examples of the radical polymerizable oligomer include an epoxy acrylate-based oligomer, a urethane acrylate-based oligomer, and a polyester acrylate-based oligomer.

The electrochromic compound of the present disclosure and another radical polymerizable compound may be copolymerized through a polymerization reaction. The electrochromic compound or the radical polymerizable compound, or both preferably have 2 or more radical polymerizable functional groups in view of formation of a polymerized product or crosslinked product. The polymerized product or crosslinked product is preferable because, in addition to mechanical strength thereof, the polymerized product or crosslinked product is not dissolved with various organic solvents or electrolytes, and does not cause interlayer migration when a multi-layer structure is formed.

An amount of the electrochromic compound of the present disclosure is preferably 10% by mass or greater but 100% by mass or less, and more preferably 30% by mass or greater but 90% by mass or less, relative to a total amount of the electrochromic composition. When the amount thereof is 10% by mass or greater, an electrochromic function of the first electrochromic layer of the electrochromic element is sufficiently exhibited, excellent durability against repetitive use upon application of voltage is achieved, and excellent coloring sensitivity is obtained. When the amount thereof is 100% by mass or less, an electrochromic function of the first electrochromic layer is exhibited, and sufficiently high coloring sensitivity relative to a thickness thereof can be obtained. When the amount thereof is 100% by mass, compatibility between the electrochromic compound and an ionic liquid used for charge transfer may be low, and therefore deteriorations in electric properties, such as reduction in durability as a result of repetitive use upon application of voltage may be caused. Notably, electric properties required vary depending on a process in which the electrochromic compound is used. In view of a balance between coloring sensitivity and durability against repetitive use, the amount of the electrochromic compound is preferably 30% by mass or greater but 90% by mass or less.

The electrochromic composition of the present disclosure includes filler and a polymerization initiator.

<Filler>

The filler is not particularly limited and may be appropriately selected depending on the intended purpose. Examples thereof include inorganic filler and organic filler.

Examples of the inorganic filler include: metal powder, such as copper, tin, aluminium, and indium; metal oxide, such as silicon oxide (silica), tin oxide, zinc oxide, titanium oxide, aluminium oxide (alumina), zirconium oxide, indium oxide, antimony oxide, bismuth oxide, calcium oxide, antimony-doped tin oxide (ATO), and tin-doped indium oxide; and metal fluoride, such as tin fluoride, calcium fluoride, and aluminium fluoride. The above-listed examples may be used alone or in combination. Among the above-listed examples, the metal oxide is preferable, and silica, alumina, and antimony-doped tin oxide (ATO) are particularly preferable, considering transparency, stability, and easiness of a surface treatment.

Examples of the organic filler include: resins, such as polyester, polyether, polysulfide, polyolefin, silicone, and polytetrafluoroethylene; low molecular compound, such as fatty acid; and pigments, such as phthalocyanine. The above-listed examples may be used alone or in combination. Among the above-listed examples, the resins are preferable considering transparency and insolubility thereof. The average primary particle diameter of the filler is preferably 1 μm or less, and more preferably 10 nm or greater but 1 μm or less. When the average primary particle diameter of the filler is 1 μm or less, coarse particles are not formed, a resultant film has an excellent surface configuration, and excellent surface smoothness.

An amount of the filler based on the solid content is preferably 0.3 parts by mass or greater but 1.5 parts by mass or less, and more preferably 0.6 parts by mass or greater but 0.9 parts by mass or less, relative to 100 parts by mass of a total amount of the radical polymerizable compounds. When the amount of the filler is 0.3 parts by mass or greater, an effect obtainable by adding the filler can be sufficiently exhibited, and excellent film formability can be obtained. When the amount of the filler is 1.5 parts by mass or less, an appropriate ratio of the triarylamine compound is maintained, and excellent electrochemical properties of the resulting electrochromic element are obtained.

<Polymerization Initiator>

The electrochromic composition of the present disclosure preferably optionally includes a polymerization initiator in order to facilitate an efficient cross-liking reaction between the electrochromic compound of the present disclosure and other radical polymerizable compounds. Examples of the polymerization initiator include a thermal polymerization initiator and a photopolymerization initiator. In view of polymerization efficiency, the polymerization initiator is preferably a photopolymerization initiator.

The thermal polymerization initiator is not particularly limited and may be appropriately selected depending on the intended purpose. Examples of the thermal polymerization initiator include: a peroxide-based initiator, such as 2,5-dimethylhexane-2,5-dihydroperoxide, dicumyl peroxide, benzoyl peroxide, t-butylcumyl peroxide, 2,5-dimethyl-2,5-di(peroxybenzoyl)hexyne-3, di-t-butylperoxide, t-butylhydroperoxide, cumene hydroperoxide, and lauroyl peroxide; and an azo-based initiator, such as azobisisobutyl nitrile, azobiscyclohexane carbonitrile, methyl azobisisobutyrate, azobisisobutylamidine hydrochloride, and 4,4'-azobis-4-cyanovaleric acid. The above-listed examples may be used alone or in combination. 1o The photopolymerization initiator is not particularly limited and may be appropriately selected depending on the intended purpose.

Examples of the photopolymerization initiator include: an acetophenone-based or ketal-based photopolymerization initiator, such as diethoxyacetophenone, 2,2-dimethoxy-1,2-diphenylethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1, 2-hydroxy-2-methyl-1-phenylpropan-1-one, 2-methyl-2-morpholino(4-methylthiophenyl)propan-1-one, and 1-phenyl-1,2-propanedione-2-(o-ethoxycarbonyl)oxime; benzoin ether-based photopolymerization initiators, such as benzoin, benzoin methyl ether, benzoin ethyl ether, benzoin isobutyl ether, and benzoin isopropyl ether; a benzophenone-based photopolymerization initiator, such as benzophenone, 4-hydroxybenzophenone, methyl o-benzoyl benzoate, 2-benzoylnaphthalene, 4-benzoylbiphenyl, 4-benzoyl phenyl ether, acrylated benzophenone, and 1,4-benzoylbenzene; and a thioxanthone-based photopolymerization initiator, such as 2-isopropylthioxanthone, 2-chlorothioxanthone, 2,4-dimethylthioxanthone, 2,4-diethylthioxanthone, and 2,4-dichlorothioxanthone.

Examples of other photopolymerization initiators include ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxybenzoyl)-2,4,4-trimethylpentylphosphine oxide, methylphenylglyoxylic acid ester, 9,10-phenanthrene, acridine-based compounds, triazine-based compounds, and imidazole-based compounds. The above-listed examples may be used alone or in combination.

Note that, a compound having an effect of accelerating photopolymerization may be used alone or in combination with the photopolymerizaiton initiator. Examples of such a compound include triethanolamine, methyl diethanol amine, ethyl 4-dimethylaminobenzoate, isoamyl 4-dimethylaminobenzoate, (2-dimethylamino)ethyl benzoate, and 4,4'-dimethylaminobenzophenone.

An amount of the polymerization initiator is preferably 0.5 parts by mass or greater but 40 parts by mass or less, and more preferably 1 part by mass or greater but 20 parts by mass or less, relative to 100 parts by mass of a total amount of the radical polymerizable compounds.

<Other Components>

The electrochromic composition of the present disclosure may further include other components according to the necessity. The above-mentioned other components are not particularly limited and may be appropriately selected depending on the intended purpose. Examples thereof include a solvent, a plasticizer, a leveling agent, a sensitizer, a dispersant, a surfactant, and an antioxidant.

The electrochromic composition of the present disclosure may include a crosslinking agent, and may be a copolymerized product (e.g., linear copolymer having a linear structure) obtained by polymerizing the electrochromic compound of the present disclosure.

Moreover, the electrochromic composition of the present disclosure may be a crosslinked product having a branched structure or a three-dimensional network structure obtained by crosslinking the electrochromic compound of the present disclosure. The crosslinking agent is not particularly limited and may be appropriately selected depending on the intended purpose. Examples thereof include isocyanurates, an amino resin, a phenol resin, amines, an epoxy compound, monofunctional (meth)acrylate, polyfunctional (meth)acrylate having 2 or more ethylenically unsaturated bonds per molecule, acrylic acid ester, and methacrylic acid ester. Among the above-listed examples, isocyanurates are preferable, and polyisocyanate having two or more isocyanate groups is particularly preferable.

Since the electrochromic composition of the present disclosure includes the electrochromic compound of the present disclosure, desirable properties of the electrochromic element can be achieved. As described above, examples of the desired properties of the electrochromic element include that the electrochromic composition is transparent in a neutralized state, that the electrochromic composition is soluble, and that an electrochromic layer can be laminated.

(Electrochromic Element)

As described above, the electrochromic element of the present disclosure includes (1) a layer including the electrochromic compound of the present disclosure or the electrochromic composition of the present disclosure, or (2) an electrolyte layer including the electrochromic compound of the present disclosure or the electrochromic composition of the present disclosure.

An embodiment where an electrochromic element includes a layer including the electrochromic compound of the present disclosure or the electrochromic composition of the present disclosure (i.e., an electrochromic layer) on a first electrode is referred to as an electrochromic element of the first embodiment.

An embodiment where an electrochromic element includes an electrolyte layer including the electrochromic compound of the present disclosure or the electrochromic composition of the present embodiment is determined as an electrochromic element of the second embodiment. Hereinafter, the electrochromic elements of the first and second embodiments will be described hereinafter.

[Electrochromic Element of First Embodiment]

The electrochromic element of the first embodiment will be described. In order to facilitate clear understanding, a scale of each member in drawings may be different from the actual scale between members. For the matter of convenience in describing the layer structure etc., moreover, the embodiment below is described with a drawing in which the first support is arranged at the bottom. However, the production or use of the first embodiment is not necessarily performed with such an arrangement. In the descriptions below, one side of the first support with respect to the thickness direction is referred to above, up, or top, and the other side of the support may be referred to as below, under, or bottom.

FIG. 1 is a view illustrating one example of a structure of the electrochromic element of the first embodiment. As illustrated in FIG. 1, the electrochromic element 10A of the first embodiment includes a first support 11, a display electrode (first electrode) 12, a first electrochromic layer 13, an electrolyte layer 14A, a second electrochromic layer 15, a counter electrode (second electrode) 16, and a second support 17, which are sequentially disposed in this order from the side of the first support 11.

The display electrode 12 is disposed on the top surface of the first support 11, and the first electrochromic layer 13 is disposed on the display electrode 12. Meanwhile, the counter electrode 16 is disposed on the bottom surface of the second support 17, and the second electrochromic layer 15 is disposed on the bottom surface of the counter electrode 16. The display electrode 12 and the counter electrode 16 are arranged to face each other with a predetermined gap between the display electrode 12 and the counter electrode 16, and the electrolyte layer 14A is disposed between the both electrodes (i.e., the display electrode 12 and the counter electrode 16).

In the electrochromic element 10A of the first embodiment, the first electrochromic layer 13 colors and decolors at the surface of the display electrode 12 due to redox reactions, and the second electrochromic layer 15 colors and decolors at the surface of the counter electrode 16 due to redox reactions.

Each member constituting the electrochromic element 10A of the first embodiment will be described hereinafter.

[First Electrochromic Layer]

The first electrochromic layer includes the electrochromic compound of the present disclosure, or the electrochromic composition of the present disclosure. In the first embodiment, the electrochromic compound of the present disclosure, and the electrochromic composition of the present disclosure are referred to as a first electrochromic compound, and a first electrochromic composition, respectively, in order to distinguish from a second electrochromic compound, and a second electrochromic composition, which will be described later.

In the first embodiment, as described above, the first electrochromic composition preferably includes the electrochromic compound of the present disclosure and another radical polymerizable compound in view of solubility of a polymer of the first electrochromic composition and durability.

One layer of the first electrochromic layer is disposed on the first electrode in the first embodiment, but the layer structure of the first electrochromic layer is not limited to such example. Two or more layers of the first electrochromic layer may be disposed on the first electrode.

The first electrochromic layer is disposed on an entire surface of the first electrode. The arrangement of the first electrochromic layer is not limited to such embodiment. The first electrochromic layer may be disposed on part of the first electrode.

The first electrochromic layer may be formed according to the method for producing the electrochromic element. The average thickness of the first electrochromic layer is preferably 0.1 µm or greater but 30 µm or less, and more preferably 0.4 µm or greater but 10 µm or less.

[First Electrode and Second Electrode]

A material of the first electrode and a material of the second electrode are not particularly limited as long as the materials thereof are each a transparent conductive material. The material of the first electrode and the material of the second electrode may be appropriately selected depending on the intended purpose. Examples of the material of the first electrode and the material of the second electrode include inorganic materials, such as tin-doped indium oxide (may be referred to as "ITO" hereinafter), fluorine-doped tin oxide (may be referred to as "FTO" hereinafter), antimony-doped tin oxide (may be referred to as "ATO" hereinafter), and zinc oxide. Among the above-listed examples, InSnO, GaZnO, SnO, $In_2O_3$, and ZnO are preferable.

Moreover, it is also possible to use an electrode which is prepared by forming transparent carbon nanotubes, or a highly-conductive non-transparent material, such as Au, Ag, Pt, and Cu, into a fine network, to improve conductivity with maintaining transparency.

A thickness of the first electrode and a thickness of the second electrode are both adjusted to attain an electric resistance value sufficient to cause a redox reaction of the first electrochromic layer and a redox reaction of the second electrochromic layer. When ITO is used as the material of the first electrode and the material of the second electrode, for example, the thickness of the first electrode and the thickness of the second electrode are each preferably 50 nm or greater but 500 nm or less.

As a production method of the first electrode and a production method of the second electrode, for example, vacuum vapor deposition, sputtering, may be ion plating used. The production methods thereof are not particularly limited as long as the method can apply the materials of the first electrode or the materials of the second electrode through coating. Any of various coating or printing methods may be used. Examples thereof include spin coating, casting, microgravure coating, gravure coating, bar coating, roll coating, wire bar coating, dip coating, slit coating, capillary coating, spray coating, nozzle coating, gravure printing, screen printing, flexo printing, offset printing, reverse printing, and inkjet printing.

[Electrolyte Layer]

The electrolyte layer is formed of an electrolyte filled between the first electrode and the second electrode. The electrolyte is introduced by injecting the electrolyte from injection holes formed in a sealing material disposed between the first electrode and the second electrode to fill between the first electrode and the second electrode.

As the electrolyte, for example, inorganic ionic salts (e.g., alkali metal salts and alkaline earth metal salts), quaternary ammonium salts, and acid or alkaline supporting electrolytes. Specific examples thereof include $LiClO_4$, $LiBF_4$, $LiAsF_6$, $LiPF_6$, $LiCF_3SO_3$, $LiCF_3COO$, $KCl$, $NaClO_3$, $NaCl$, $NaBF_4$, $NaSCN$, $KBF_4$, $Mg(ClO_4)$, and $Mg(BF_4)_2$.

As a material of the electrolyte, an ionic liquid may be used.

Among ionic liquids, an organic ionic liquid is preferable because an organic ionic liquid is in a liquid state in a wide temperature range including room temperature. Examples of a cationic component of a molecular structure of the organic ionic liquid include: imidazole derivatives, such as N,N-dimethylimidazole salts, N,N-methylethylimidazole salts, and N,N-methylpropylimidazole salts; pyridinium derivatives, such as N,N-dimethylpyridinium salts, and N,N-methylpropylpyridinium salts; and aliphatic quaternary ammonium salts, such as trimethylpropyl ammonium salts, trimethylhexyl ammonium salts, and triethylhexyl ammonium salts. In view of stability in the atmosphere, moreover, a fluorine-containing compound is preferably used as an anionic component. Examples thereof include $BF_4^-$, $CF_3SO_3^-$, $PF_4^-$, $(CF_3SO_2)_2N^-$, and tetracyanoboron anion $(B(CN)_4^-)$.

As a material of the electrolyte, an ionic liquid including an arbitrary combination of a cationic component and an anionic component is preferably used. The ionic liquid may be directly dissolved in a photopolymerizable monomer, an oligomer, or a liquid crystal material. When the solubility of the electrolyte is poor, the electrolyte may be dissolved in a small amount of a solvent, and the resultant solution may be mixed with the photopolymerizable monomer, oligomer, or liquid crystal material. Examples of the solvent include propylene carbonate, acetonitrile, γ-butyrolactone, ethylene carbonate, sulfolane, dioxolane, tetrahydrofuran, 2-methyltetrahydrofuran, dimethyl sulfoxide, 1,2-dimethoxyethane, 1,2-ethoxymethoxyethane, polyethylene glycol, alcohols, and mixed solvents thereof.

The electrolyte is not necessarily a low-viscous liquid, and may be in any of various states, such as a gel, a cross-linked polymer, and a liquid crystal dispersion. It is advantageous to form the electrolyte into a gel or solid state in view of an improvement in strength of a resultant element, and an improvement in reliability of the element. A solidification method is preferably to retain the electrolyte and the solvent in a polymer because high ion conductivity and a solid strength can be obtained. The polymer is preferably a photocurable resin because an electrochromic element can be produced at a low temperature and within a short period compared to a method where a thin film is formed through thermal polymerization or by evaporating a solvent. The average thickness of the electrolyte layer formed of the electrolyte is not particularly limited and may be appropriately selected depending on the intended purpose. The average thickness thereof is preferably 100 nm or greater but 10 μm or less.

[Second Electrochromic Layer]

The second electrochromic layer composed of a single layer is disposed on the bottom surface of the second electrode, but the arrangement of the second electrochromic layer is not limited to the above-described arrangement. Two or more layers of the second electrochromic layer may be disposed. Moreover, the second electrochromic layer may be disposed on the entire bottom surface of the second electrode, but the arrangement of the second electrochromic layer is not limited to the above-described arrangement. The second electrochromic layer may be disposed on part of the bottom surface of the second electrode.

The second electrochromic layer may include a second electrochromic compound that is a compound (viologen compound) represented by General Formula (I) below. The second electrochromic layer include an electrochromic composite where the viologen compound represented by General Formula (I) is adsorbed on conductor nanostructures or semiconductor nanostructures (i.e., conductor or semiconductor nanostructures). The viologen compound represented by General Formula (I) can be bonded to or adsorbed on the conductor or semiconductor nanostructures. When the electrochromic composite is used in an electrochromic element, the electrochromic element colors mainly in blue, and excellent image memory, i.e., colored image retention, can be obtained.

General Formula (I)

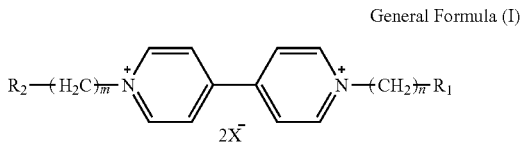

Other than the viologen compound represented by General Formula (I), the second electrochromic layer may include a phosphonic acid compound or straight-chain alkyl phosphonate disclosed in Japanese Unexamined Patent Application Publication No. 2017-111434. Alternatively, the phosphonic acid compound or straight-chain alkyl phosphonate may be adsorbed together with the viologen compound in the second electrochromic layer.

General Formula (II)

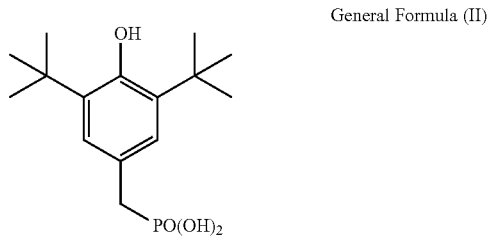

—Viologen Compound—

The viologen compound represented by General Formula (I) above will be described.

In General Formula (I), $R_1$ and $R_2$ are each a hydrogen atom, an aryl group having 14 or less carbon atoms, a heteroaryl group, a branched alkyl group having 10 or less carbon atoms, an alkenyl group, a cycloalkyl group, and a functional group that can be bonded to a hydroxyl group; n and m are each 0 or an integer of from 1 through 10; and X— is an ion neutralize the charge.

In a more preferable embodiment, $R_1$ or $R_2$ is a functional group that can be bonded to a hydroxyl group. As a result, adsorption and fixation of the viologen compound onto the transparent electrode (e.g., ITO) is realized. In the case where bearing particles formed of metal oxide are disposed on a transparent electrode, similarly, adsorption and fixation of the second electrochromic layer to the transparent electrode is realized. Therefore, it is advantageous that $R_1$ or $R_2$ is a functional group that can be bonded to a hydroxyl group. In a particularly preferable embodiment, $R_1$ and $R_2$ are both a functional group that can be bonded to a hydroxyl group.

Examples of the functional group that can be bonded to a hydroxyl group include a phosphonic acid group, a phosphoric acid group, a carboxylic acid group, a sulfonyl group, a silyl group, and a silanol group. Among the above-listed examples, a phosphoric acid group, a phosphoric acid group, and a carboxyl group are preferable, and a phosphoric acid group is more preferable, considering simplicity of synthesis, adsorption to bearing particles when the bearing particles of metal oxide are disposed on a transparent electrode, and stability of the compound.

Examples of the phosphonic acid group include a methphosphonic acid group, an ethylphosphonic acid group, a propylphosphonic acid group, a hexylphosphonic acid group, an octylphosphonic acid group, a decylphosphonic acid group, a dodecylphosphonic acid group, an octadecylphosphonic acid group, a benzylphosphonic acid group, a phenylethylphosphonic acid group, a phenylpropylphosphonic acid group, and a biphenylphosphonic acid group.

Examples of the phosphoric acid group include a methylphosphoric acid group, an ethylphosphoric acid group, a propylphosphoric acid group, a hexylphosphoric acid group, an octylphosphoric acid group, a decylphosphoric acid group, a dodecylphosphoric acid group, an octadecylphosphoric acid group, a benzylphosphoric acid group, a phenylethylphosphoric acid group, a phenylpropylphosphoric acid group, and a biphenylphosphoric acid group.

Examples of the carboxyl group include a methylcarboxylic acid group, an ethylcarboxylic acid group, a propylcarboxylic acid group, a hexylcarboxylic acid group, an octylcarboxylic acid group, a decylcarboxylic acid group, a dodecylcarboxylic acid group, an octadecylcarboxylic acid group, a benzylcarboxylic acid group, a phenylethylcarboxylic acid group, a phenylpropylcarboxylic acid group, a biphenylcarboxylic acid group, a 4-propylphenylcarboxylic acid group, and a 4-propylbiphenylcarboxylic acid group.

Examples of the sulfonyl group include a methylsulfonyl group, an ethylsulfonyl group, a propylsulfonyl group, a hexylsulfonyl group, an octylsulfonyl group, a decylsulfonyl group, a dodecylsulfonyl group, an octadecylsulfonyl group, a benzylsulfonyl group, a phenylethylsulfonyl group, a phenylpropylsulfonyl group, and a biphenylsulfonyl group.

Examples of the silyl group include a methylsilyl group, an ethylsilyl group, a propylsilyl group, a hexylsilyl group, an octylsilyl group, a decylsilyl group, a dodecylsilyl group, an octadecylsilyl group, a benzylsilyl group, a phenylethylsilyl group, a phenylpropylsilyl group, and a biphenylsilyl group.

Examples of the silanol group include a methylsilanol group, an ethylsilanol group, a propylsilanol group, a hexylsilanol group, an octylsilanol group, a decylsilanol group, a dodecylsilanol group, an octadecylsilanol group, a benzylsilanol group, a phenylethylsilanol group, a phenylpropylsilanol group, and a biphenylsilanol group.

In General Formula (I), the ion $X^-$ neutralizing the charge is a monovalent anion, and is not particularly limited as long as the ion can stable form a pair with a cation site. As the ion $X^-$ neutralizing the charge, for example, Br ion ($Br^-$), Cl ion ($Cl^-$), I ion ($I^-$), OTf (triflate) ion ($OTf^-$), $ClO_4$ ion ($ClO_4^-$), PF ion ($PF_6^-$), and $BF_4$ ion ($BF_4^-$) are preferable.

The viologen compound is preferably a symmetric viologen compound having an alkyl chain of a certain length. In this case, in General Formula (I), m and n are each preferably from 4 through 10, and m and n are more preferably the same integer.

Specific exemplary compounds of the viologen compound are listed are listed below, but the viologen compound is not limited to the following compounds.

<Exemplary Compound A>

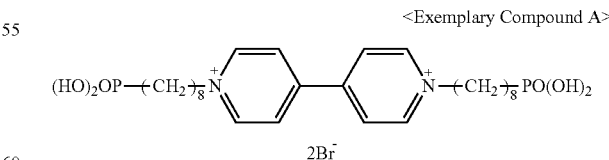

<Exemplary Compound B>

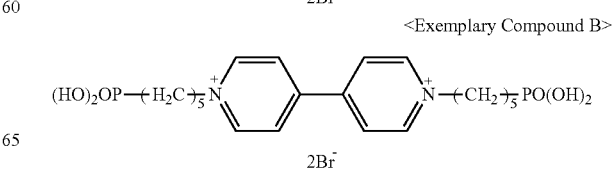

-continued

<Exemplary Compound C>

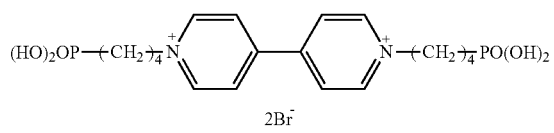

<Exemplary Compound D>

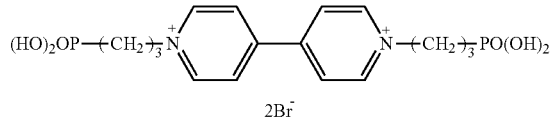

<Exemplary Compound E>

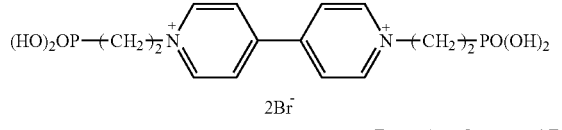

<Exemplary Compound F>

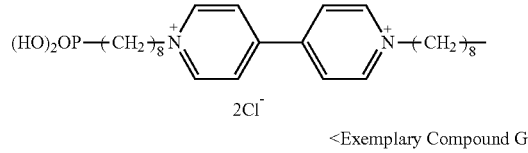

<Exemplary Compound G>

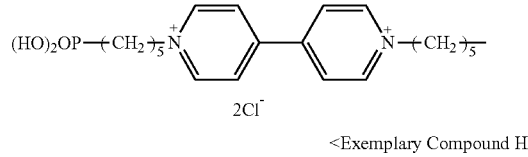

<Exemplary Compound H>

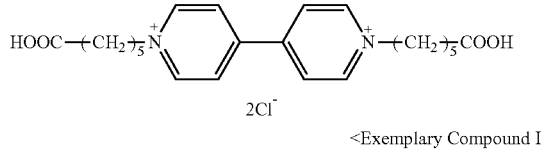

<Exemplary Compound I>

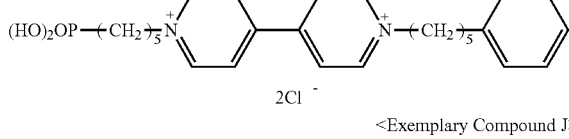

<Exemplary Compound J>

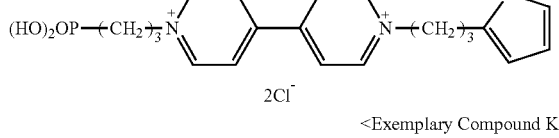

<Exemplary Compound K>

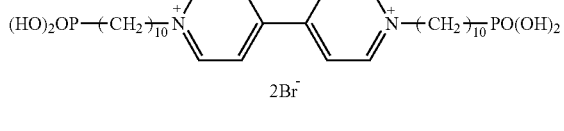

—Conductor or Semiconductor Nanostructures—

The conductor or semiconductor nanostructures will be described.

The conductor or semiconductor nanostructures are preferably transparent.

In General Formula (I), at least one of $R_1$ to $R_2$ is a functional group that can be bonded to a hydroxyl group. For the bonding or adsorption structure of the viologen compound onto the conductor or semiconductor nanostructures, a phosphonic acid group, a sulfonic acid group, a phosphoric acid group, or a carboxyl group is used. In this case, the second electrochromic compound easily forms a complex with the nanostructures to become an electrochromic composite having excellent color image retention.

Two or more phosphonic acid groups, sulfonic acid groups, phosphoric acid groups, and/or carboxyl groups may be included in the viologen compound. When the viologen compound includes a silyl group or a silanol group, the viologen compound is bonded to each nanostructure via a siloxane bond to make a strong bond, and therefore a stable electrochromic composite can be obtained. The siloxane bond refers to a chemical bond via a silicon atom and an oxygen atom.

Moreover, the electrochromic composite is not particularly limited as long as the electrochromic composite has a structure where the viologen compound and the nanostructures are bonded via a siloxane bond. A bonding method and embodiment thereof are not particularly limited.

The conductor or semiconductor nanostructures are structures having nano-scale irregularities, such as nanoparticles, and porous nanostructures. A material constituting the conductor or semiconductor nanostructures is preferably metal oxide in view of transparency and conductivity.

Examples of metal oxide include metal oxides each including, as a main component, titanium oxide, zinc oxide, tin oxide, zirconium oxide, cerium oxide, yttrium oxide, boron oxide, magnesium oxide, strontium titanate, potassium titanate, barium titanate, calcium titanate, calcium oxide, ferrite, hafnium oxide, tungsten oxide, iron oxide, copper oxide, nickel oxide, cobalt oxide, barium oxide, strontium oxide, vanadium oxide, indium oxide, aluminosilicate, calcium phosphate, or aluminosilicate. The above-listed examples may be used alone or in combination. Among the above-listed examples, titanium oxide, zinc oxide, tin oxide, zirconium oxide, iron oxide, magnesium oxide, indium oxide, and tungsten oxide are preferable, and titanium oxide is more preferable in view of electrical properties, such as electrical conductivity, and physical properties, such as optical characteristics. Use of the metal oxide or a mixture of the metal oxides above achieves excellent response speed of coloring and decoloring.

A shape of the metal oxide is preferably metal oxide particles having the average primary particle diameter of 30 nm or less. As the average primary particle diameter thereof is smaller, light transmittance of the metal oxide increases, and the surface area (may be referred to as a "specific surface area" hereinafter) of the electrochromic composite per unit volume increases. Since the electrochromic composite has a large specific surface area, the second electrochromic compound is more efficiently carried on the conductor or semiconductor nanostructures, and multicolor display of an excellent display contrast ratio of coloring and decoloring can be realized. The specific surface area of the electrochromic composite is not particularly limited and may be appropriately selected depending on the intended purpose. For example, the specific surface area thereof is preferably 100 $m^2/g$ or greater.

The average primary particle diameter of the metal oxide particles can be determined by observing randomly selected 100 metal oxide particles under a transmission electron microscope (TEM), determining a projected area of each particle, calculating a circle equivalent diameter of the obtained area to determine each particle diameter, and calculating an average value of the measured values to determine an average primary particle diameter of the metal oxide particles.

Examples of a formation method of the second electrochromic layer include vacuum vapor deposition, sputtering, and ion plating. When the materials of the second electrochromic layer can be applied to form a film by coating, various coating or printing methods can be used. Examples thereof include spin coating, casting, microgravure coating, gravure coating, bar coating, roll coating, wire bar coating, dip coating, slit coating, capillary coating, spray coating, nozzle coating, gravure printing, screen printing, flexographic printing, offset printing, reverse printing, and inkjet printing.

The average thickness of the second electrochromic layer is not particularly limited and may be appropriately selected depending on the intended purpose. The average thickness thereof include 0.2 µm or greater but 5.0 µm or less. When the average thickness is 0.2 µm or greater, desirable coloring density can be obtained. When the average thickness is 5.0 µm or less, increase in production cost can be suppressed and impaired visibility due to unintentional coloring can be prevented. The second electrochromic layer can be formed by vacuum film formation, but the second electrochromic layer is preferably formed by applying a particle dispersion paste by coating in view of productivity.

[First Support and Second Support]

The first support and the second support (i.e., the support) have a function of supporting the first electrode, the first electrochromic layer, the second electrode, the second electrochromic layer, etc. Any of organic materials and inorganic materials known in the art may be used as the support as long as the material is a transparent material that can support the above-mentioned layers.

As the support, for example, a glass substrate, such as non-alkali glass, borosilicate glass, float glass, and soda-line glass, may be used. As the support, moreover, a resin substrate may be used. Examples of the resin substrate include a polycarbonate-based resin, an acryl-based resin, a polyethylene-based resin, a polyvinyl chloride-based resin, a polyester-based resin, an epoxy-based resin, a melamine-based resin, a phenol resin, a polyurethane-based resin, and a polyimide-based resin. Moreover, a surface of the support may be coated with a transparent insulation layer, a UV-cut layer, or an antireflection layer in order to enhance water-vapor barrier properties, gas barrier properties, UV resistance, or visibility.

A planar shape of the support is not particularly limited and may be appropriately selected depending on the intended purpose. For example, the shape thereof may be a rectangle or a circle. Two or more of the supports may be laminated. For example, the support having a structure where the electrochromic display element is sandwiched between two glass substrates can enhance water-vapor barrier properties and gas barrier properties.

[Other Members]

Other members are not particularly limited and may be appropriately selected depending on the intended purpose. Examples thereof include a porous insulation layer, an antideterioration layer, and a protective layer.

—Porous Insulation Layer—

The porous insulation layer has a function of retaining the electrolyte, as well as separating the first electrode and the second electrode from each other to attain electrical insulation between the first electrode and the second electrode. A material of the porous insulation layer is not particularly limited, as long as the material is porous. The material is preferably an organic material, an inorganic material, or a composite of the organic material and the inorganic material, all of which have high insulating properties and durability and excellent film formability.

Examples of a formation method of the porous insulation layer include a sintering method (a method where polymer particles or inorganic particles are added to a binder to partially fuse the particles to utilize pores generated between the particles), an extraction method (a method where, after forming a constituting layer with an organic or inorganic material soluble in a solvent and a binder insoluble in the solvent, the organic or inorganic material is dissolved with the solvent to obtain pores), a foaming method where a coating liquid is foamed, a phase transformation method where a mixture of high-molecular-weight compounds are phase-separated by appropriately using a good solvent and a poor solvent, and a radiation method where pores are formed by applying various radial rays.

—Antideterioration Layer—

The antideterioration layer has a role of performing a reverse chemical reaction to a reaction of the first electrochromic layer or second electrochromic layer to take a balance of charges. In this manner, it is possible to prevent corrosions or deteriorations caused by an irreversible redox reaction of the first electrode or second electrode. Note that, the reverse chemical reaction means functioning as a capacitor as well as a case where the antideterioration layer is oxidized or reduced.

A material of the antideterioration layer is not particularly limited and may be appropriately selected depending on the intended purpose, as long as the material is a material that prevents corrosions caused by an irreversible redox reaction of the first electrode or the second electrode. As the material of the antideterioration layer, for example, antimony tin oxide, nickel oxide, titanium oxide, zinc oxide, tin oxide, or conductive or semiconductive metal oxide containing two or more of the above-listed materials can be used. The antideterioration layer can be composed of a porous film that has a degree of porosity not to interfere an injection of the electrolyte. For example, a preferable porous film that permeates the electrolyte and functions as an antideterioration layer can be obtained by fixing conductive or semiconductive metal oxide particles (e.g., antimony tin oxide, nickel oxide, titanium oxide, zinc oxide, and tin oxide) on the second electrode with a binder (e.g., an acryl-based binder, an alkyd-based binder, an isocyanate-based binder, an urethane-based binder, an epoxy-based binder, and a phenol-based binder).

—Protective Layer—

The protective layer is used for protecting the electrochromic element from external stress or chemicals used for washing processes, preventing leakage of the electrolyte, and preventing migration of substances (e.g., moisture and oxygen in the air) that are unnecessary for stable operations of the electrochromic element.

As a material of the protective layer, for example, a UV-curable resin or a thermoset resin may be used. Specific examples thereof include an acryl-based resin, a urethane-based resin, and an epoxy-based resin.

The average thickness of the protective layer is not particularly limited and may be appropriately selected depending on the intended purpose. The average thickness thereof is preferably from 1 µm through 200 µm.

[Production Method of Electrochromic Element of First Embodiment]

One example of the production method of the electrochromic element of the first embodiment will be described.

First, a display electrode 12 is formed on a first support 11. Then, a coating liquid (electrolytic liquid) that includes a first electrochromic composition including the electrochromic compound of the present disclosure and other radical polymerizable compounds is applied onto the display electrode 12. In this manner, a first laminate, in which the display electrode 12 and the first electrochromic layer 13 are sequentially formed on the first support 11, is produced.

The electrochromic compound of the present disclosure and another radical polymerizable compound for use are the same as ones described in the electrochromic element of the first embodiment.

The coating liquid may be optionally diluted with solvent to be used for coating. The solvent is not particularly limited and may be appropriately selected depending on the intended purpose. Examples thereof include: an alcohol-based solvent, such as methanol, ethanol, propanol, and butanol; a ketone-based solvent, such as acetone, methyl ethyl ketone, methyl isobutyl ketone, and cyclohexanone; an ester-based solvent, such as ethyl acetate, and butyl acetate; an ether-based solvent, such as tetrahydrofuran, dioxane, and propyl ether; a halogen-based solvent, such as dichloromethane, dichloroethane, trichloroethane, and chlorobenzene; an aromatic solvent, such as benzene, toluene, and xylene; and a cellosolve-based solvent, such as methyl cellosolve, ethyl cellosolve, and cellosolve acetate. The above-listed examples may be used alone or in combination.

The dilution rate with the solvent varies depending on solubility of the first electrochromic composition, a coating method for use, or a thickness of the first electrochromic layer, and is appropriately selected.

Examples of the coating method include dip coating, spray coating, beads coating, and ring coating.

Moreover, the production method of the electrochromic element of the first embodiment may further include a step (polymerization or crosslinking step) including externally applying energy to the coated first electrochromic composition to polymerize or crosslink the first electrochromic composition.

In the polymerization or crosslinking step, after applying the first electrochromic composition onto the first electrode, energy is externally applied to the first electrochromic composition to cure the first electrochromic composition to thereby form a first electrochromic layer. Examples of the external energy include heat, light, and radial rays. A method for applying the heat energy is performed by heating the first electrochromic layer from the side of the coated surface or the side of the support using gas (e.g., air and nitrogen), vapor, various heat media, infrared rays, or electromagnetic waves.

The heating temperature is not particularly limited and may be appropriately selected depending on the intended purpose. The heating temperature is preferably from 60° C. through 170° C. As the light energy, UV irradiation light sources mainly having emission wavelength in ultraviolet rays (UV), such as high-pressure mercury lamps, and metal halide lamps can be used. However, it is possible to use a visible light source matched to an absorption wavelength of a radical polymerizable group-containing compound or a photopolymerization initiator. The irradiation dose of UV is not particularly limited and may be appropriately selected depending on the intended purpose. The irradiation dose thereof is preferably from 5 mW/cm$^2$ through 15,000 mW/cm$^2$.

Next, a counter electrode 16 is formed on the second support 17. Thereafter, a coating liquid including an electrochromic composite, which includes the second electrochromic composition and conductor or semiconductor nanostructures, is applied onto the counter electrode 16. In this manner, a second laminate where the counter electrode 16 and the second electrochromic layer 15 are sequentially disposed on the second support 17 is produced.

As the second electrochromic composition and conductor or semiconductor nanostructures included in the electrochromic composite, any of the examples of the electrochromic composition and conductor or semiconductor nanostructures described in the first embodiment can be used.

Next, the electrolyte solution was applied between the first laminate and the second laminate to dispose an electrolyte layer 14A between the first laminate and the second laminate. In this manner, the electrochromic element 10A of the first embodiment is produced. In the case where the electrolyte constituting the electrolyte layer 14A is curable by light or heat, curing is performed after bonding the first laminate and the second laminate via the electrolyte.

The production method of an electrochromic element of the first embodiment may further include other steps according to the necessity.

As other steps, for example, a step including forming a porous insulation layer on the first electrochromic layer 13 may be included when the electrochromic element 10A of the first embodiment includes the porous insulation layer. Moreover, the porous insulation layer may be formed on the bottom surface of the second electrochromic layer 15, or may be mixed with the electrolyte constituting the electrolyte layer 14A.

Moreover, the production method of the first embodiment may include a step including forming an antideterioration layer or a protective layer in the electrochromic element 10A of the first embodiment, in the case where the electrochromic element 10A of the first embodiment includes the antideterioration layer or the protective layer.

[Electrochromic Element of Second Embodiment]

The electrochromic element of the second embodiment will be described. The electrochromic element 10B of the second embodiment is an embodiment identical to the electrochromic element 10A of the first embodiment in FIG. 1, except that the first electrochromic layer 13 and the second electrochromic layer 15 are not disposed. The electrochromic element 10B of the second embodiment uses an electrolyte layer including the electrochromic compound or the present disclosure or the electrochromic composition of the present disclosure in addition to the electrolyte layer 14A of the electrochromic element 10A of the first embodiment.

Figure 2:
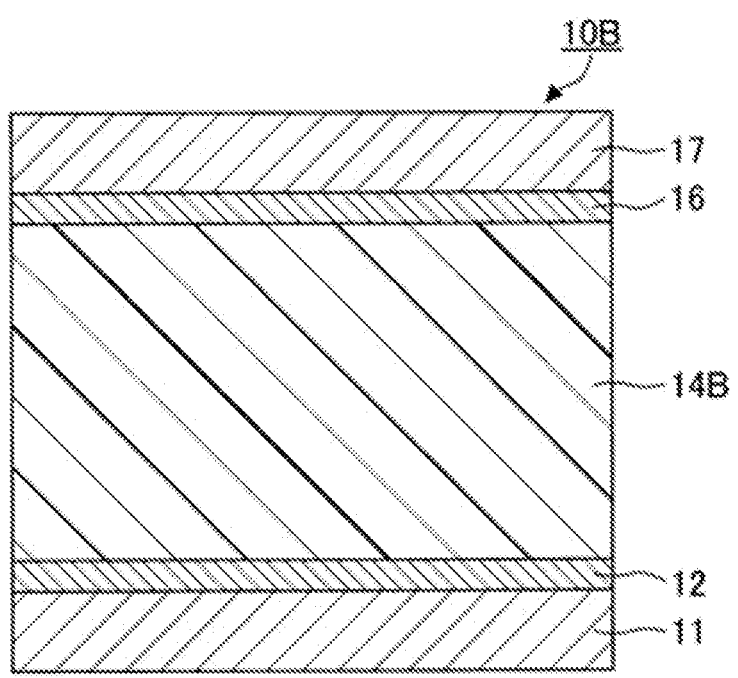
FIG. 2 is a schematic view illustrating one example of the layer structure of the electrochromic element of the second embodiment.

FIG. 2 is a view illustrating one example of a structure of the electrochromic element of the second embodiment. The electrochromic element 10B of the second embodiment illustrated in FIG. 2 includes a first support 11, a display electrode 12, an electrolyte layer 14B, a counter electrode 16, and a second support 17, disposed in this order from the side of the first support 11. The electrolyte layer 14B includes the electrochromic compound of the present disclosure or the electrochromic composition of the present disclosure, and an electrolyte. Since members constituting the electrochromic element 10B of the second embodiments are identical to the members constituting the electrochromic element 10A of the first embodiment, detailed descriptions thereof are omitted.

[Production Method of Electrochromic Element of Second Embodiment]

One example of the production method of the electrochromic element of the second embodiment will be described. The production method of the electrochromic element 10B of the second embodiment does not include the steps for forming the first electrochromic layer 13 and the second electrochromic layer 15 of the electrochromic element 10A of the first embodiment illustrated in FIG. 1. The production method of the electrochromic element 10B of the second embodiment includes a step including forming an electrolyte layer 14B including the electrochromic compound of the present disclosure or the electrochromic composition of the present disclosure, instead of the electrolyte layer 14A.

Specifically, a display electrode 12 is formed on the first support 11. A counter electrode 16 is formed on the second support 17.

Next, an electrolyte solution including the electrochromic compound of the present disclosure or the electrochromic composition of the present disclosure, and an electrolyte is prepared. Thereafter, the electrolyte solution is applied between a display electrode 12 and a counter electrode 16 to dispose an electrolyte layer 14B between the display electrode 12 and the counter electrode 16. In this manner, the electrochromic element 10B of the second embodiment is produced.

The electrochromic element of the first embodiment and the electrochromic element of the second element have excellent photodurability and durability against repetitive use. Therefore, the electrochromic elements of the first and second embodiments can be suitably used for electrochromic displays, large display panels (e.g., stock and share price displays), anti-glare mirrors, and light-controlling elements (e.g., light-controlling glass). Moreover, the electrochromic elements of the first and second embodiments can be suitably used for low-voltage-driven elements (e.g., touch-panel key switches), photoswitches, photomemories, electronic paper, and electronic albums.

The embodiments are as described above. These embodiments are described as examples, and should not be construed as to limit the scope of the present disclosure. The embodiments can be carried out in any other variations, and can be combined, omitted, substituted, or altered within the spirit of the present disclosure. These embodiments and modifications thereof are included within the scope and subject matter of the present disclosure, as well as being included within a scope equivalent to the scope defined by the claims of the present disclosure.

EXAMPLES

The present disclosure will be described below by way of Examples. The present disclosure should not be construed as being limited to these Examples.

Example 1

<Synthesis of Electrochromic Compound 1>

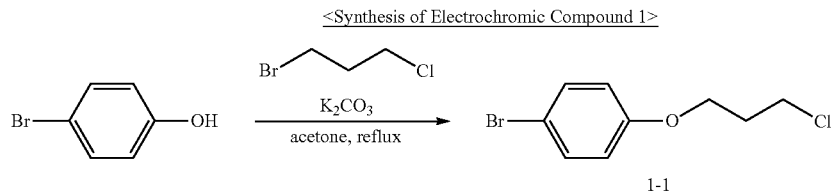

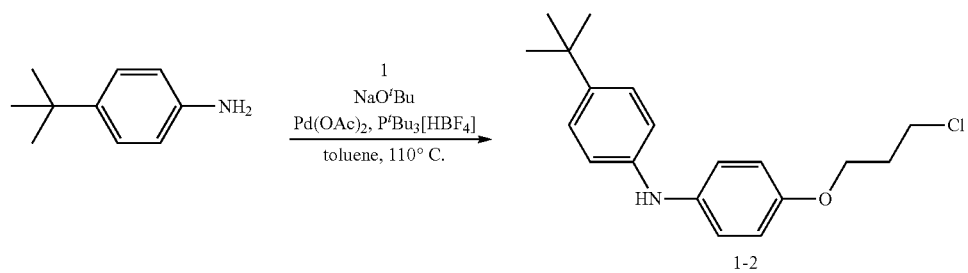

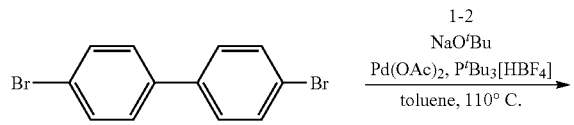

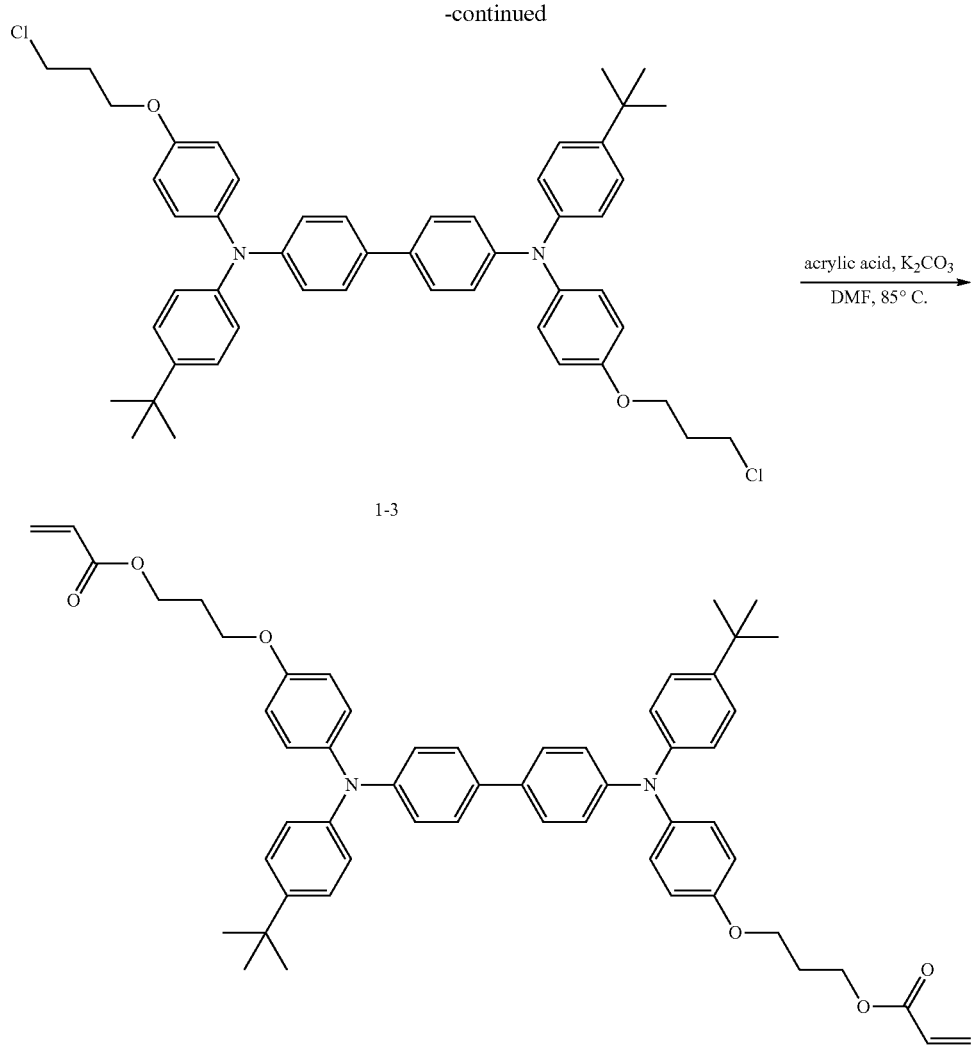

1-3

<Synthesis of Compound 1-1>

A recovery flask was charged with p-bromophenol (available from TOKYO CHEMICAL INDUSTRY CO., LTD., 18.4 g, 106 mmol), acetone (300 mL), potassium carbonate (available from KANTO CHEMICAL CO., LTD., powder, 2.4 eq to phenol, 35.2 g, 255 mmol), and 1-bromo-3-chloropropane (available from TOKYO CHEMICAL INDUSTRY CO., LTD., 2 eq to phenol, 33.4 g, 212 mmol), and the resultant mixture was heated and stirred at an internal temperature of 40° C. for 15 hours. The obtained organic layer was concentrated, and the residue was purified by silica gel column chromatography (hexane/ethyl acetate), to thereby obtain Compound 1-1 (yielded amount: 24.4 g, yield: 92%) as colorless solids.

$^1$H NMR (500 MHz, CDCl$_3$) δ7.40-7.37 (m, 2H), 6.98-6.94 (m, 2H), 6.91-6.88 (m, 2H), 6.83-6.80 (m, 2H), 4.10 (t, J=6.0 Hz, 2H), 3.76 (t, J=6.5 Hz, 2H), 2.26-2.22 (quint, J=6.5 Hz, 2H)

MS(ASAP): 247.955 (measured value), 247.960 (calculated value)

<Synthesis of Compound 1-2>

A 4-necked flask was charged with 4-tertbutylaniline (1.56 g, 10.5 mmol), palladium acetate (available from TOKYO CHEMICAL INDUSTRY CO., LTD., 88 mg, 0.4 mmol), tri-tert-butylphosphonium tetrafluoroborate (available from TOKYO CHEMICAL INDUSTRY CO., LTD., 348 mg, 1.2 mmol), Compound 1-1 (10 mmol, 2.5 g), sodium tert-butoxide (available from TOKYO CHEMICAL INDUSTRY CO., LTD., 1.82 g, 18.0 mmol), and purged with argon gas, followed by adding dehydrated toluene (available from KANTO CHEMICAL CO., LTD., 30 mL), which had been deaerated with argon gas. Thereafter, the resultant solution was heated at 110° C. for 4 hours under a flow of argon gas. The resultant solution was then cooled down to room temperature, followed by filtering the solution by CELITE filtration. The CELITE was washed with toluene, and the obtained filtrates were combined and concentrated by vacuum concentration. The obtained residues were purified by silica gel column chromatography (hexane/toluene), followed by vacuum drying, to thereby obtain Compound 1-2 (yielded amount: 2.36 g, yield: 74%) as a brown liquid.

MS(ASAP): 317.148 (measured value), 317.155 (calculated value)

<Synthesis of Compound 1-3>

A 4-necked flask was charged with 4,4'-dibromobiphenyl (available from TOKYO CHEMICAL INDUSTRY CO., LTD., 1.13 g, 3.6 mmol), Compound 1-2 (2.36 g, 7.42 mmol), palladium acetate (available from TOKYO CHEMICAL INDUSTRY CO., LTD., 18.0 mg, 0.08 mmol), and tri-tert-butylphosphonium tetrafluoroborate (available from TOKYO CHEMICAL INDUSTRY CO., LTD., 69.6 mg, 0.24 mmol), and purged with argon gas. Thereafter, xylene (30 mL) was added and the resultant mixture was bubbled with argon gas for 10 minutes. The resultant solution was heated at 70° C., followed by adding sodium tert-butoxide (available from TOKYO CHEMICAL INDUSTRY CO., LTD., 1.15 g, 12.0 mmol). The resultant solution was heated at 110° C. for 3 hours. The resultant solution was filtered by CELITE filtration. The CELITE was washed with toluene, and the obtained filtrates were combined and concentrated to thereby obtain brown solids. Methanol was added to the obtained solids, and the resultant mixture was dispersed by means of an ultrasonic cleaner. The solids were collected from the dispersion liquid by filtration, to thereby obtain Compound 1-3 (yielded amount: 2.77 g, yield: 98%), as colorless solids.

$^1$H NMR (500 MHz, acetone-$d_6$) δ7.47-7.51 (m, 4H), 7.32-7.35 (m, 4H), 7.06-7.09 (m, 4H), 6.96-7.01 (m, 12H), 4.15 (t, J=6.0 Hz, 4H), 3.82 (t, J=6.5 Hz, 4H), 2.23-2.27 (m, 4H), 1.31 (s, 18H)

MS(ASAP): 784.350 (measured value), 784.356 (calculated value)

<Synthesis of Electrochromic Compound 1>

A 4-necked flask was charged with Compound 1-3 (2.75 g, 3.5 mmol), acrylic acid (available from TOKYO CHEMICAL INDUSTRY CO., LTD., 1.51 g, 21 mmol), potassium carbonate (available from KANTO CHEMICAL CO., LTD., powder, 3.7 g, 25.2 mmol), dehydrated dimethylformamide (60 mL), and 2,6-ditert-butylcresol (two crystals), and the resultant mixture was heated at 85° C. for 8.5 hours. The resultant solution was cooled down to room temperature. To the solution, water and ethyl acetate were added, followed by separating an organic phase. An aqueous phase was extracted 4 times with ethyl acetate. The combined organic phase was washed 3 times with water, and subsequently washed with saturated saline solution, followed by drying with anhydrous sodium sulfate. The drying agent was separated by filtration, the filtrate was concentrated by vacuum concentration, and the obtained residues were purified by silica gel column chromatography (toluene/ethyl acetate). To the eluate, 2,6-ditert-butylcresol (1.55 mg) was added, and the resultant was concentrated by vacuum concentration, to thereby obtain Electrochromic Compound 1 (yielded amount: 2.29 g, yield: 76%, added amount of BHT: 677 ppm), as pale yellow amorphous solids.

$^1$H NMR (500 MHz, CDCl$_3$) δ:7.44 (d, J=9.0 Hz, 4H), 7.30 (d, J=8.5 Hz, 4H), 7.02 (d, J=9.0 Hz, 4H), 6.93 (dd, J=0.3 Hz, 9.0 Hz, 8H), 6.89 (d, J=9.0 Hz, 4H), 6.34 (dd, J1=1.5 Hz, J2=17.0 Hz, 2H), 6.22-6.16 (m, 2H), 5.95 (dd, J1=1.5 Hz, J2=10.0 Hz, 2H), 4.27 (t, J=6.5 Hz, 4H), 4.04 (t, J=6.0 Hz, 4H), 2.08 (quint, J=6.5 Hz, 4H), 1.26 (s, 18H)

MS(ASAP): 856.440 (measured value), 856.445 (calculated value)

Example 2

<Synthesis of Electrochromic Compound 2>

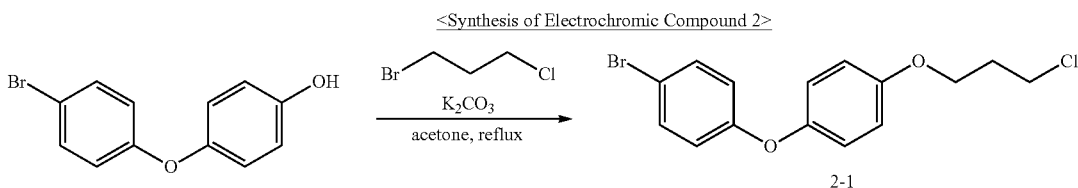

2-1

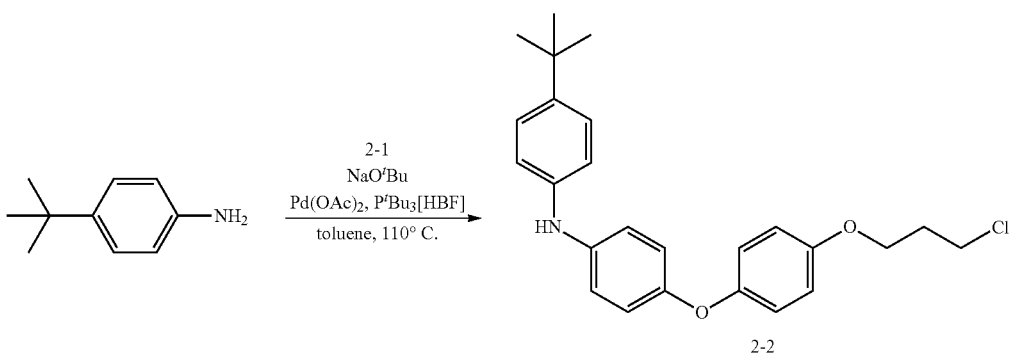

2-2

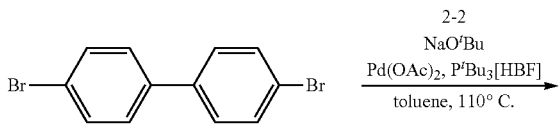

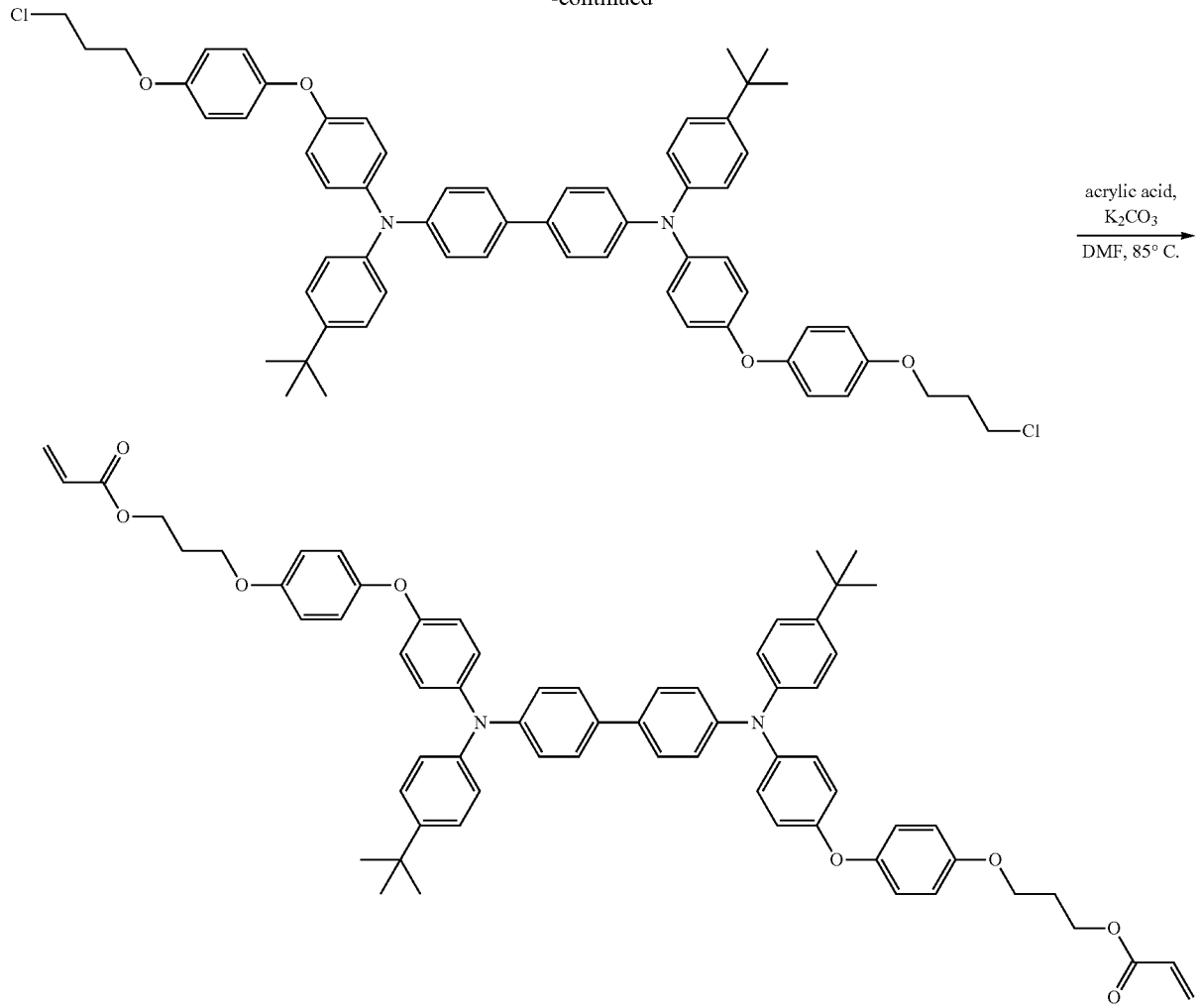

<Synthesis of Compound 2-1>

A recovery flask was charged with 4-bromo-4'-hydroxydiphenyl ether (available from Aldrich, 10.3 g, 38.7 mmol), acetone (100 mL), potassium carbonate (available from KANTO CHEMICAL CO., LTD., powder, 3 eq to phenol, 16.0 g, 116 mmol), and 1-bromo-3-chloropropane (available from TOKYO CHEMICAL INDUSTRY CO., LTD., 2.5 eq to phenol, 15.2 g, 96.8 mmol), and the resultant mixture was heated and stirred for 6 hours under reflux. The resultant solution was cooled down to room temperature, the precipitates were separated by filtration, and the collected precipitates were washed with ethyl acetate. The combined organic phase was concentrated, and the residues (20 g) were purified by silica gel column chromatography (hexane/ethyl acetate), to thereby obtain Compound 2-1 (yielded amount: 12.6 g, yield: 95%) as pale yellow solids.

$^1$H NMR (500 MHz, CDCl$_3$) δ7.40-7.37 (m, 2H), 6.98-6.94 (m, 2H), 6.91-6.88 (m, 2H), 6.83-6.80 (m, 2H), 4.10 (t, J=6.0 Hz, 2H), 3.76 (t, J=6.5 Hz, 2H), 2.26-2.22 (quint, J=6.5 Hz, 2H).

MS(ASAP): 339.981 (measured value), 339.987 (calculated value)

<Synthesis of Compound 2-2>

Under a flow of argon gas, a 4-necked flask was charged with palladium acetate (available from TOKYO CHEMICAL INDUSTRY CO., LTD., 121 mg, 0.55 mmol), tri-tert-butylphosphonium tetrafluoroborate (available from TOKYO CHEMICAL INDUSTRY CO., LTD., 480 mg, 1.66 mmol), Compound 2-1 (18.4 mmol, 6.29 g), dehydrated toluene (available from KANTO CHEMICAL CO., LTD., 65 mL), which had been deaerated with argon gas, and sodium tert-butoxide (available from TOKYO CHEMICAL INDUSTRY CO., LTD., 2.57 g, 27.6 mmol), and the resultant mixture was heated at 80° C. for 10 minutes. Thereafter, 4-tertbutylaniline (3.55 g, 23.9 mmol) was added. The resultant solution was heated at 115° C. (bath temperature) for 2.5 hours. The solution was cooled down to room temperature, followed by filtering the solution by CELITE filtration. The CELITE was washed with toluene, and the obtained filtrates were combined and concentrated by vacuum concentration. The obtained residues (10 g) were purified by silica gel column chromatography (hexane/toluene=7/3→3/7 (v/v), gradient), followed by vacuum drying, to thereby obtain Compound 2-2 (yielded amount: 5.9 g, yield: 78%) as a brown liquid.

MS(ASAP): 409.172 (measured value), 409.181 (calculated value)

<Synthesis of Compound 2-3>

A 4-necked flask was charged with 4,4'-dibromobiphenyl (available from TOKYO CHEMICAL INDUSTRY CO., LTD., 2.15 g, 6.9 mmol), Compound 2-2 (5.8 g, 14.15 mmol), palladium acetate (available from TOKYO CHEMICAL INDUSTRY CO., LTD., 31 mg, 0.138 mmol), tri-tert-butylphosphonium tetrafluoroborate (available from TOKYO CHEMICAL INDUSTRY CO., LTD., 120 mg, 0.414 mmol), and toluene (50 mL), which had been deaerated with argon gas. The resultant mixture was bubbled with argon gas for 10 minutes. The resultant solution was then heated to 80° C., and sodium tert-butoxide (available from TOKYO CHEMICAL INDUSTRY CO., LTD., 1.99 g, 20.7 mmol) was added to the solution. The resultant solution was heated at 115° C. for 7 hours. The solution was then cooled down to a temperature around 70° C., followed by filtering the solution by hot CELITE filtration. The CELITE was washed with toluene, and the obtained filtrates were combined and concentrated. The obtained solids were purified by silica gel column chromatography (hexane/toluene), followed by vacuum drying, to thereby obtain Compound 2-3 (yielded amount: 5.73 g, yield: 86%) as colorless amorphous solids.

$^1$H NMR (500 MHz, $C_6D_6$) δ7.43-7.40 (m, 4H), 7.23-7.16 (m, 12H), 7.10-7.07 (m, 4H), 6.99-6.90 (m, 8H), 3.55 (t, J=6.0 Hz, 4H), 1.69 (quint, J=6.0 Hz, 4H), 1.24 (s, 18H).

MS (ASAP): 968.400 (measured value), 968.409 (calculated value)

<Synthesis of Electrochromic Compound 2>

A 4-necked flask was charged with Compound 2-3 (5.64 g, 5.8 mmol), acrylic acid (available from TOKYO CHEMICAL INDUSTRY CO., LTD., 2.51 g, 34.9 mmol), potassium carbonate (available from KANTO CHEMICAL CO., LTD., powder, 6.2 g, 41.9 mmol), dehydrated dimethylformamide (130 mL), and 2,6-di-tert-butylcresol (3 crystals), and the resultant mixture was heated at 85° C. for 12.5 hours. The resultant solution was cooled down to room temperature. To the solution, water and ethyl acetate were added, and the organic phase was separated. The aqueous phase was extracted 4 times with ethyl acetate. The combined organic phase was washed 4 times with water, and subsequently washed with saturated saline solution, followed by drying with anhydrous sodium sulfate. The drying agent was separated by filtration, the filtrate was concentrated by vacuum concentration, and the obtained residues (8.2 g) were purified by silica gel column chromatography (toluene/ethyl acetate (10/0)). To the eluate, 2,6-ditert-butylcresol (3.2 mg) was added, and the resultant was concentrated by vacuum concentration, to thereby obtain Electrochromic Compound 2 (yielded amount: 5.37 g, yield: 88.7%, added amount of BHT: 600 ppm) as colorless amorphous solids.

$^1$H NMR (500 MHz, $C_6D_6$) δ:7.43 (dd, J1=7.0 Hz, J2=2.0 Hz, 4H), 7.23-7.17 (m, 12H), 7.08 (d, J1=7.0 Hz, J2=2.0 Hz, 4H), 6.97 (dd, J1=6.5 Hz, J2=2.0 Hz, 4H), 6.92 (dd, J1=6.5 Hz, J2=2.0 Hz, 4H), 6.66 (d, J1=6.8 Hz, J2=2.0 Hz, 4H), 6.28 (d, J1=17.3 Hz, J2=1.43 Hz, 2H), 5.95 (d, J1=17.5 Hz, J2=10.3 Hz, 2H), 5.23 (d, J1=10.3 Hz, J2=1.43 Hz, 2H), 4.16 (t, J=6.3 Hz, 4H), 3.53 (t, J=6.3 Hz, 4H), 1.74 (quint, J=6.3 Hz, 4H), 1.24 (s, 18H).

MS(ASAP): 1040.486 (measured value), 1040.498 (calculated value).

Example 1-1

<Production of First Electrochromic Element>

A production example of an electrochromic element of Example 1-1 will be described hereinafter.

—Formation of First Electrochromic Layer on First Electrode—

In order to form a first electrochromic layer on a first electrode, a first electrochromic composition having the following composition was prepared.

[Composition]

First Electrochromic Compound (Exemplary Compound 1): 50 parts by mass

IRGACURE184 (available from BASF Japan): 5 parts by mass

Polyethylene glycol including a diacryloxy group ("PEG400DA," available from Nippon Kayaku Co., Ltd.): 50 parts by mass Methyl ethyl ketone: 900 parts by mass Next, the obtained first electrochromic composition was applied onto an ITO glass substrate (40 mm×40 mm, thickness: 0.7 mm, ITO film thickness: about 100 nm) serving as a first electrode by spin coating. The obtained coating film was irradiated with UV by a UV irradiation device (SPOT CURE, available from USHIO INC.) at 10 mW for 60 seconds, followed by annealing at 60° C. for 10 minutes, to thereby form the crosslinked first electrochromic layer having the average thickness of 400 μm.

—Formation of Antideterioration Layer on Second Electrode—

Next, a titanium oxide nanoparticle dispersion liquid (product name: SP210, available from SHOWA DENLO K.K., average particle diameter: about 20 nm) was applied as an antideterioration layer onto an ITO glass substrate (40 mm×40 mm, thickness: 0.7 mm, ITO film thickness: about 100 nm) serving as a second electrode by spin coating. Then, the coated film was annealed at 120° C. for 15 minutes, to thereby form a nanostructure semiconductor material formed of a titanium oxide particle film having a thickness of 1.0 μm.

—Formation of Second Electrochromic Layer on Second Electrode—

In order to form a second electrochromic layer on a second electrode, a second electrochromic composition having the following composition was prepared.

[Composition]

Second Electrochromic Compound (Exemplary Compound A): 20 parts by mass

Tetrafluoropropanol: 980 parts by mass

The obtained second electrochromic composition was applied onto the nanostructure semiconductor material formed of the titanium oxide particle film on the second electrode by spin coating to allow the electrochromic compound in the second electrochromic composition to be adsorbed on the titanium oxide particles. Then, any excess part of the electrochromic compound, which was not adsorbed on the titanium oxide particles, was washed off with methanol, to thereby form a second electrochromic layer.

—Filling with Electrolyte Solution—

An electrolyte solution having the following composition was prepared.

[Composition]
IRGACURE184 (available from BASF Japan): 5 parts by mass
PEG400DA (available from Nippon Kayaku Co., Ltd.): 100 parts by mass 1-Ethyl-3-methylimidazolium tetracyanoborate (available from Merck KGaA): 50 parts by mass The obtained electrolyte solution was collected by 30 mg with a micropipette, and the collected electrolyte solution was dripped onto the ITO glass substrate, serving as the second electrode, having the antideterioration layer and the second electrochromic layer. Onto the ITO glass substrate, the ITO glass substrate, serving as the first electrode, having the crosslinked first electrochromic layer, was bonded in a manner that drawing parts for the electrodes are secured, to thereby produce a bonded element. The bonded element was irradiated with UV (wavelength: 250 nm) by a UV irradiation device (SPOT CURE, available from USHIO INC.) at 10 mW for 60 seconds, to thereby produce an electrochromic element of Example 1-1.

<Coloring and Decoloring Operation>

Coloring and decoloring of the produced electrochromic element of Example 1-1 were confirmed. Voltage of −2 V was applied between the drawing part of the first electrode and the drawing part of the second electrode for 5 seconds. As a result, coloring owing to First Electrochromic Compound of the first electrochromic layer was confirmed in the area where the first electrode and the second electrode were overlapped. In addition, coloring owing to Second Electrochromic Compound of the second electrochromic layer was also confirmed. Subsequently, voltage of +2 V was applied between the drawing part of the first electrode and the drawing part of the second electrode for 5 seconds. As a result, it was confirmed that the area where the first electrode and the second electrode were overlapped was decolored and turned transparent.

Figure 3:
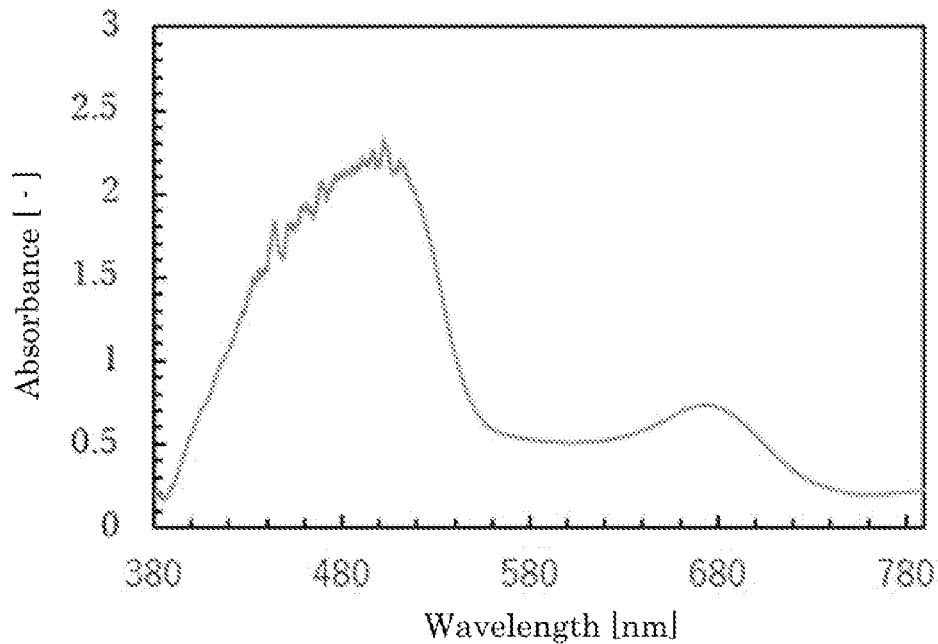
FIG. 3 is a graph depicting a UV-visible absorption spectrum of the colored electrochromic element of Example 1-1.

An ultraviolet visible absorption spectrum of the colored electrochromic element of Example 1-1 is depicted in FIG. 3. The absorption spectrum of FIG. 3 is a spectrum obtained by subtracting the ultraviolet visible absorption spectrum of colored Second Electrochromic compound of the electrochromic element of Example 1-1 and the ultraviolet visible absorption spectra of decolored First Electrochromic Compound and Second Electrochromic Compound of the electrochromic element of Example 1-1 from the ultraviolet visible absorption spectrum of colored First Electrochromic Compound. Specifically, the absorption spectrum of FIG. 3 represents an ultraviolet visible spectrum of only colored First Electrochromic Compound (Exemplary Compound 1). In FIG. 3, the absorption spectrum in the wavelength range of 380 nm to 780 nm is depicted. It was confirmed that, as depicted in FIG. 3, both First Electrochromic Compound and Second Electrochromic Compound colored in orange to brawn as observed with naked eyes.

Examples 1-2 to 1-10

Figure 4:
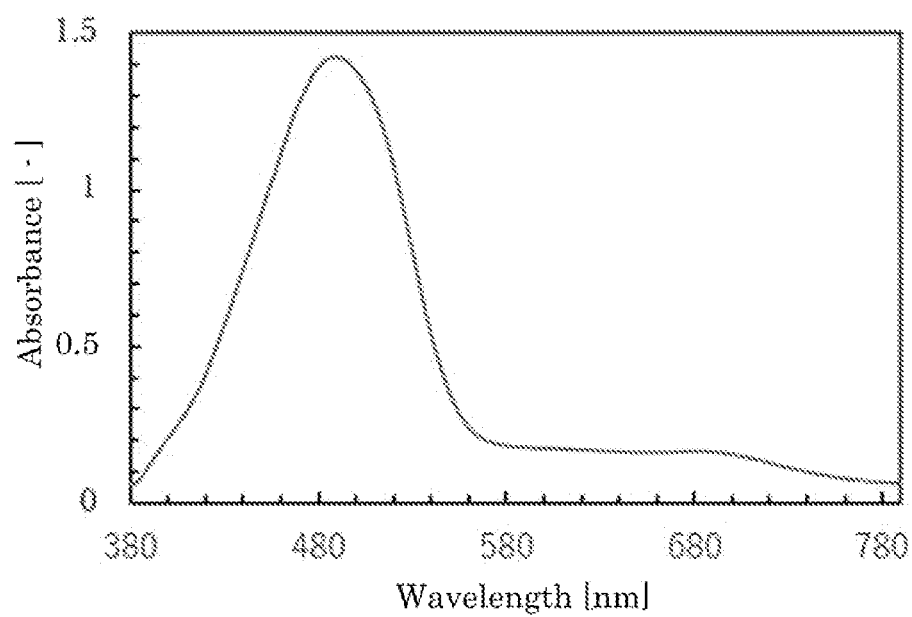
FIG. 4 is a graph depicting a UV-visible absorption spectrum of the colored electrochromic element of Example 1-2.

Electrochromic elements of Examples 1-2 to 1-10 were produced in the same manner as in Example 1-1, except that Exemplary Compound 1 used as First Electrochromic Compound was replaced with Exemplary Compounds 2 to 10, respectively. It was confirmed that each of the electrochromic elements of Examples 1-2 to 1-10 also had an ultraviolet visible absorption spectrum similar to that of the electrochromic element of Example 1-1. An ultraviolet visible absorption spectrum of Second Electrochromic Compound in Example 1-2 for coloring is depicted in FIG. 4. Second Electrochromic Compound colored in orange similarly to Exemplary Compound 1.

Comparative Examples 1-1 to 1-6

Electrochromic elements of Comparative Examples 1-1 to 1-6 were produced in the same manner as in Example 1-1, except that Exemplary Compound 1 used as First Electrochromic Compound was replaced with Comparative Compounds 1 to 6, respectively. It was confirmed that each of the electrochromic elements of Comparative Examples 1-1 to 1-6 also had an ultraviolet visible absorption spectrum similar to that of the electrochromic element of Example 1-1.

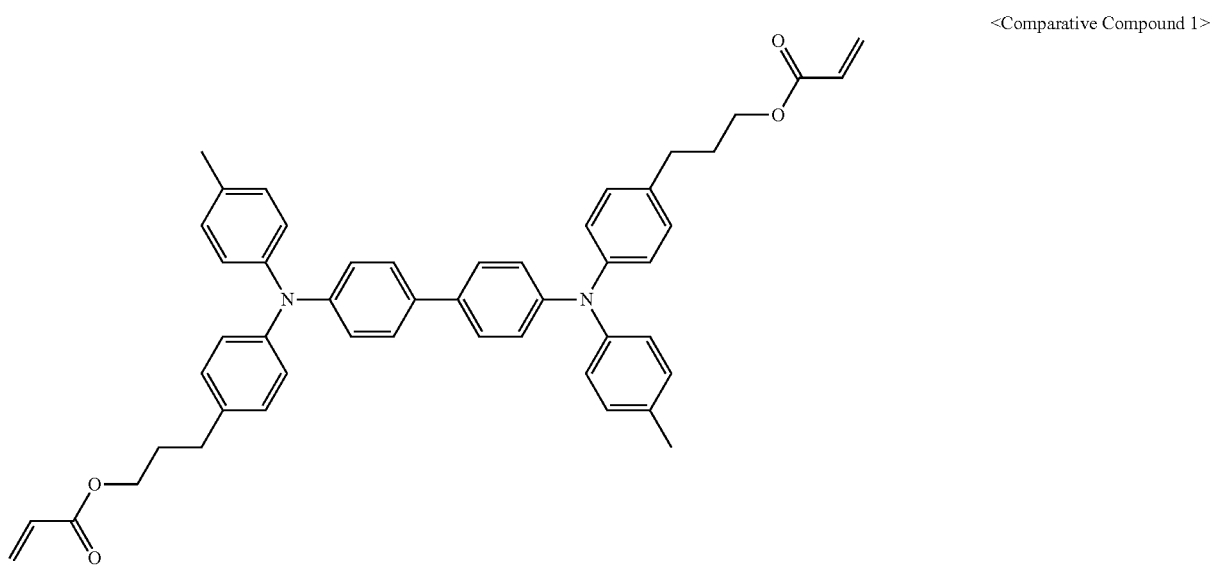

<Comparative Compound 1>

-continued
<Comparative Compound 2>
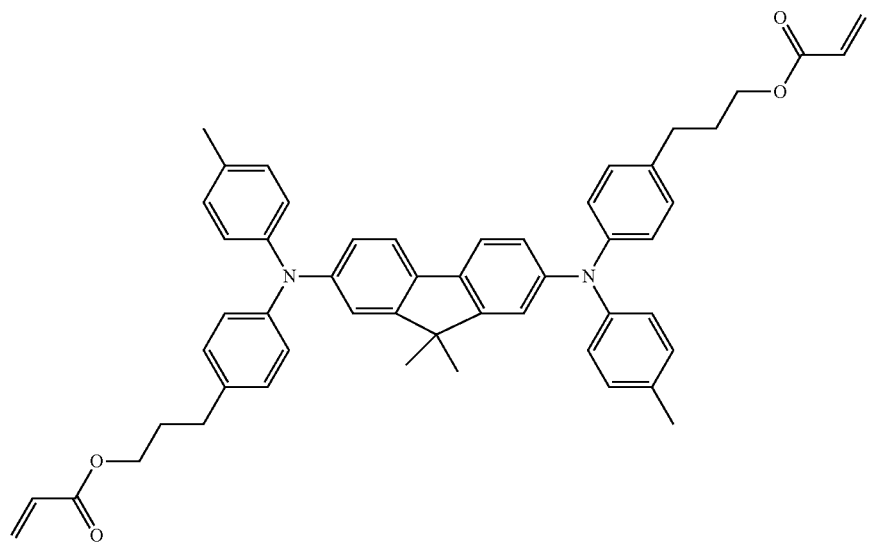
<Comparative Compound 3>
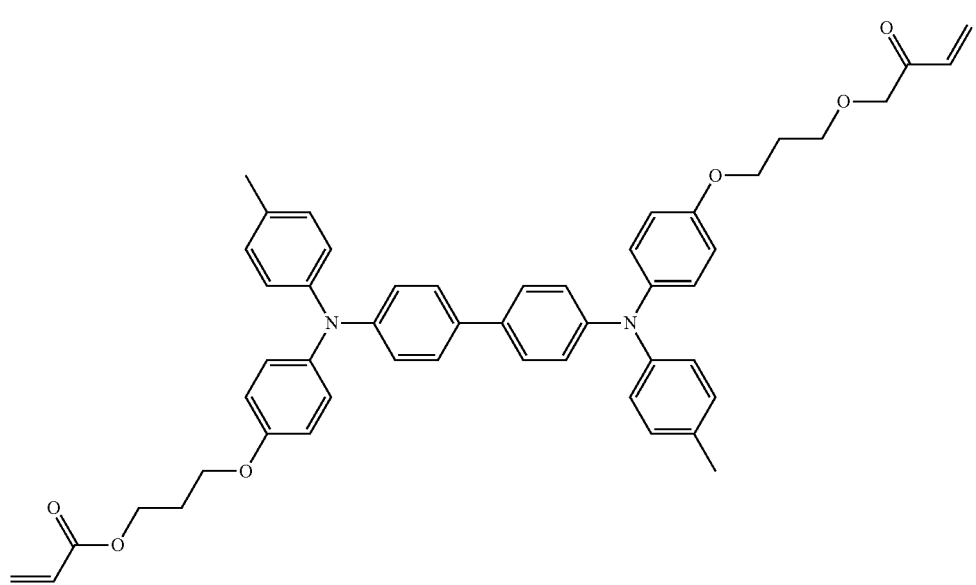
<Comparative Compound 4>
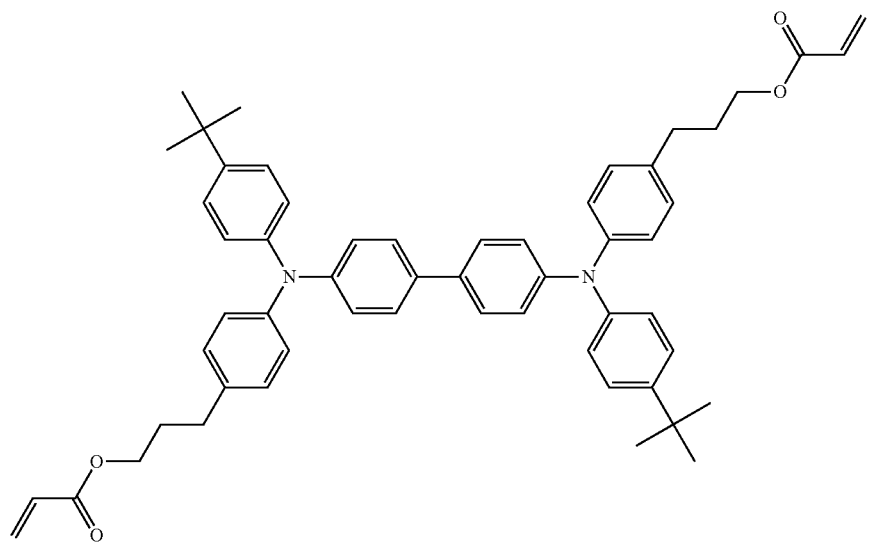

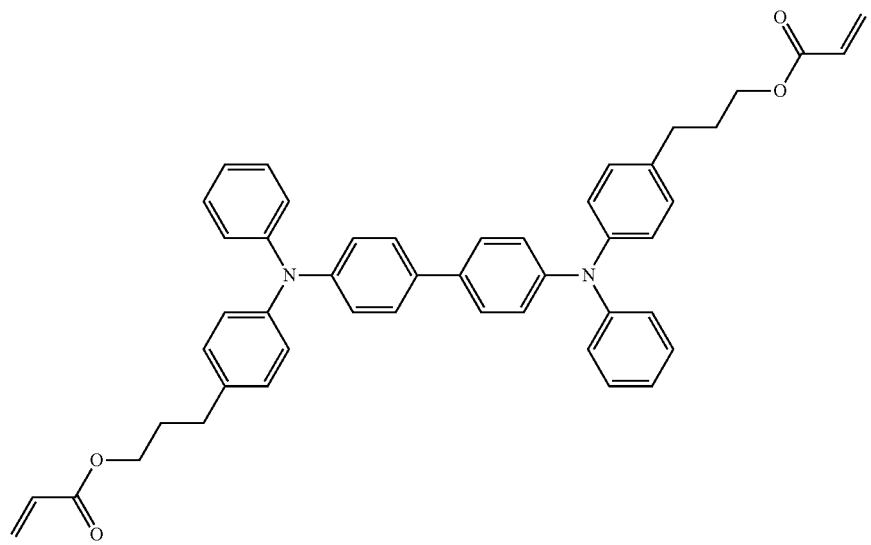

<Comparative Compound 5>

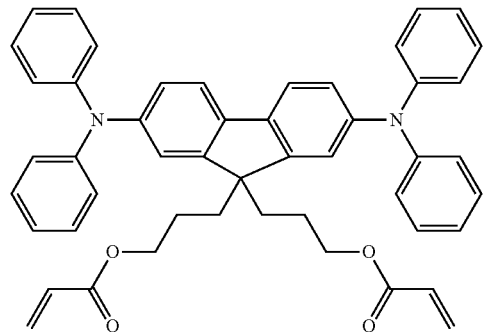

<Comparative Compound 6>

The types and added positions of the electrochromic compounds used in Examples 1-1 to 1-10 and Comparative Examples 1-1 to 1-6 are presented in Tables 1-1 and 1-2.

<Evaluations>

Each of the produced electrochromic elements was subjected to a repeat test, a continuous coloring test, a photodurability test, and a color test. The results are presented in Tables 1-1 and 1-2.

[Test 1-1: Durability Test to Repetitive Use]

Each of the produced electrochromic elements of Examples and Comparative Examples was tested. Voltage of 2 V was applied between the drawing part of the first electrode and the drawing part of second electrode for 5 seconds to color the electrochromic element, followed by applying voltage of −2 V between the drawing part of the first electrode and the drawing part of the second electrode for 5 seconds to decolor the electrochromic element, which was determined as 1 operation of coloring and decoloring. The coloring and decoloring operation was performed 10,000 times. The maximum absorbance in the visible region (380 nm to 780 nm) during the operations was determined as λmax (490 nm in Example 1). A change in the absorbance after the 10,000 operations was measured by means of a spectrometer (USB4000, available from Ocean Optics, Inc.), and was evaluated based on the following criteria.

[Evaluation Criteria]

A: The absorbance of Amax was 95% or greater of the initial absorbance.
B: The absorbance of Amax was 90% or greater or less than 95% of the initial absorbance.
C: The absorbance of Amax was less than 90% of the initial absorbance.

[Test 1-2: Continuous Coloring Test]

Each of the produced electrochromic elements of Examples and Comparative Examples was tested. Voltage of 1.6 V was applied between the first electrode and the second electrode to color the electrochromic element, and the colored state was maintained continuously for 48 hours.

The absorbance in the visible region (380 nm to 780 nm) before and after the application of voltage was measured by a spectrometer (USB4000, available from Ocean Optics, Inc.), and each yellow index (YI) was calculated. A difference in YI before and after the application of voltage was determined as ΔYI, which was evaluated based on the following criteria.

[Evaluation Criteria]

A: ΔYI was less than 0.5.
B: ΔYI was 0.5 or greater but less than 3.
C: ΔYI was 3 or greater.

[Test 1-3: Photodurability Test]

Each of the produced electrochromic elements of Examples and Comparative Examples was tested. Voltage of 1.6 V was applied between the first electrode and the second electrode to color the electrochromic element. While maintaining the colored stated of the electrochromic element, the electrochromic element was continuously irradiated with light through a UV-cut filter (product name: Lumicool 1501UH, available from LINTEC Corporation) by artificial solar lighting (product name: SOLAX XC-100 W, available from available from SERIC Ltd., illuminance: 150,000 lux) for 48 hours. Then, the electrochromic element was irradiated with light by a deuterium tungsten halogen light source (product name: DH-2000, available from Ocean Optics, Inc.). The transmittance of the electrochromic element in the visible region (380 nm to 780 nm) before and after the irradiation was measured by a spectrometer (USB4000, available from Ocean Optics, Inc.), and each yellow index (YI) was calculated. A difference in YI before and after the irradiation was determined as ΔYI, which was evaluated based on the following criteria.

[Evaluation Criteria]

A: ΔYI was less than 5.

B: ΔYI was 5 or greater but less than 10.

C: ΔYI was 10 or greater.

TABLE 1-1

| | First electrochromic composition | | Second electrochromic composition | |
|---|---|---|---|---|
| | First electrochromic compound | Location for use | Second electrochromic compound | Location for use |
| Ex. 1-1 | Exemplary Compound 1 | First electrochromic layer | Exemplary Compound A | Second electrochromic layer |
| Ex. 1-2 | Exemplary Compound 2 | First electrochromic layer | Exemplary Compound A | Second electrochromic layer |
| Ex. 1-3 | Exemplary Compound 3 | First electrochromic layer | Exemplary Compound A | Second electrochromic layer |
| Ex. 1-4 | Exemplary Compound 4 | First electrochromic layer | Exemplary Compound A | Second electrochromic layer |
| Ex. 1-5 | Exemplary Compound 5 | First electrochromic layer | Exemplary Compound A | Second electrochromic layer |
| Ex. 1-6 | Exemplary Compound 6 | First electrochromic layer | Exemplary Compound A | Second electrochromic layer |
| Ex. 1-7 | Exemplary Compound 7 | First electrochromic layer | Exemplary Compound A | Second electrochromic layer |
| Ex. 1-8 | Exemplary Compound 8 | First electrochromic layer | Exemplary Compound A | Second electrochromic layer |
| Ex. 1-9 | Exemplary Compound 9 | First electrochromic layer | Exemplary Compound A | Second electrochromic layor |
| Ex. 1-10 | Exemplary Compound 10 | First electrochromic layer | Exemplary Compound A | Second electrochromic layer |
| Comp. Ex. 1-1 | Comparative Compound 1 | First electrochromic layer | Exemplary Compound A | Second electrochromic layer |
| Comp. Ex. 1-2 | Comparative Compound 2 | First electrochromic layer | Exemplary Compound A | Second electrochromic layer |
| Comp. Ex. 1-3 | Comparative Compound 3 | First electrochromic layer | Exemplary Compound A | Second electrochromic layer |
| Comp. Ex. 1-4 | Comparative Compound 4 | First electrochromic layer | Exemplary Compound A | Second electrochromic layer |
| Comp. Ex. 1-5 | Comparative Compound 5 | First electrochromic layer | Exemplary Compound A | Second electrochromic layer |
| Comp. Ex. 1-6 | Comparative Compound 6 | First electrochromic layer | Exemplary Compound A | Second electrochromic layer |

TABLE 1-2

| | Test 1-1 | Test 1-2 | Test 1-3 |
|---|---|---|---|
| Ex. 1-1 | A | A | A |
| Ex. 1-2 | A | A | A |
| Ex. 1-3 | A | A | A |
| Ex. 1-4 | A | A | A |
| Ex. 1-5 | A | A | A |
| Ex. 1-6 | A | A | A |
| Ex. 1-7 | A | A | A |
| Ex. 1-8 | A | A | A |
| Ex. 1-9 | A | A | A |
| Ex. 1-10 | A | A | A |
| Comp. Ex. 1-1 | B | B | C |
| Comp. Ex. 1-2 | B | B | C |
| Comp. Ex. 1-3 | B | B | C |
| Comp. Ex. 1-4 | B | B | C |
| Comp. Ex. 1-5 | C | C | C |
| Comp. Ex. 1-6 | C | C | C |

It was confirmed from the results presented in Tables 1-1 and 1-2 that the electrochromic elements of Examples 1-1 to 1-10 achieved all of the durability against repetitive use, continuous coloring, and photodurability, and had excellent continuous driving stability and photodurability. On the other hand, it was confirmed that the electrochromic elements of Comparative Examples 1-1 to 1-6 did not achieve all of the durability against repetitive use, continuous coloring, and photodurability Accordingly, the electrochromic composition of the present disclosure contributed more to the improvement of continuous driving stability and photodurability of the electrochromic element, compared to the materials known in the art.

Example 2-1

<Production of Second Electrochromic Element>

A production example of an electrochromic element of Example 2-1 will be described hereinafter.

—Formation of Spacer on First Electrode—

An isopropanol solution of gap-controlling particles (average particle diameter: 80 μm, product name: Micropearl GS, available from SEKISUI CHEMICAL CO., LTD.) was applied onto an ITO glass substrate (40 mm×40 mm, thickness: 0.7 mm, ITO film thickness: about 100 nm) serving as a first electrode, and the coated film was dried at 80° C. for 3 minutes.

—Formation of Antideterioration Layer on Second Electrode—

Next, a titanium oxide nanoparticle dispersion liquid (product name: SP210, available from SHOWA DENLO K.K., average particle diameter: about 20 nm) was applied as an antideterioration layer onto an ITO glass substrate (40 mm×40 mm, thickness: 0.7 mm, ITO film thickness: about 100 nm) serving as a second electrode by spin coating. Then, the coated film was annealed at 120° C. for 15 minutes, to thereby form a nanostructure semiconductor material formed of a titanium oxide particle film having a thickness of 1.0 μm.

—Bonding of Substrates—

The ITO substrate serving as the first electrode and the ITO substrate serving as the second electrode were bonded in a manner that the first electrode and the second electrode were faced to each other, and the ITO substrates were arranged to be displaced by 5 mm from each other to leave drawing parts of the electrodes. Thereafter, the edge surfaces of the bonded element were coated with a sealing material (TB3050B, available from ThreeBond Holdings Co., Ltd.) except two inlets. The resultant bonded element was irradiated with UV (wavelength: 250 nm) by an UV irradiation device (SPOT CURE, available from USHIO INC.) at 10 mW for 60 seconds.

—Filling with Electrolyte Solution—

An electrolyte solution having the following composition was prepared.

[Composition]
Electrochromic Compound 2-1 (Exemplary Compound M1): 50 parts by mass
1-ethyl-3-methylimidazolium bisfluorosulfonylimide (EMIM-FSI) (available from Merck KGaA): 100 parts by mass
N-methylpyrrolidone (NMP): 600 parts by mass The obtained electrolyte solution was collected by 30 mg with a micropipette, and the collected electrolyte solution was injected into the cell from the inlets. The inlets were then sealed with the sealing material, followed by irradiating the cell with UV (wavelength: 250 nm) by an UV irradiation device (SPOT CURE, available from USHIO INC.) at 10 mW for 60 seconds. In the manner as described, an electrochromic element of Example 2-1, as illustrated in FIG. 2, was produced.

<Coloring and Decoloring Operation>

Coloring and decoloring of the produced electrochromic element of Example 2-1 were confirmed in the same manner as the confirmation method used for the electrochromic element of Example 1-1. As a result, coloring (orange) owing to Electrochromic Compound 2 of the electrochromic layer was confirmed in the area where the first electrode and the second electrode were overlapped when voltage of 2 V was applied between the drawing part of the first electrode and the drawing part of the second electrode for 5 seconds. Moreover, it was confirmed that, when voltage of −2 V was applied between the drawing part of the first electrode and the drawing part of the second electrode for 5 seconds, the area where the first electrode and the second electrode were overlapped was decolored and turned transparent.

Examples 2-2 to 2-5

Electrochromic elements of Examples 2-2 to 2-5 were produced in the same manner as in Example 2-1, except that Exemplary Compound M1 used as Electrochromic Compound 2-1 was replaced with Exemplary Compounds M2 to M5, respectively.

Comparative Examples 2-1 to 2-6

Electrochromic elements of Examples 2-2 to 2-5 were produced in the same manner as in Example 2-1, except that Exemplary Compound M1 used as Electrochromic Compound 2-1 was replaced with Comparative Compounds m1 to m6, respectively. It was confirmed that each of the electrochromic elements of Comparative Examples 2-1 to 2-6 colored owing to Electrochromic Compound 2-1, similar to the electrochromic element of Example 2-1.

<Comparative Compound m1>

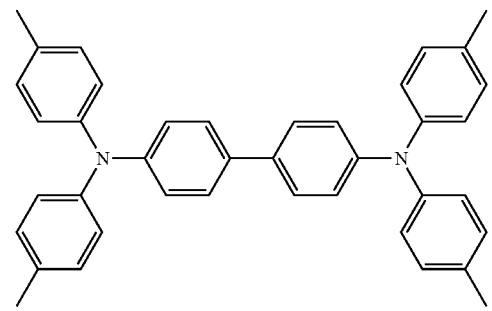

<Comparative Compound m2>

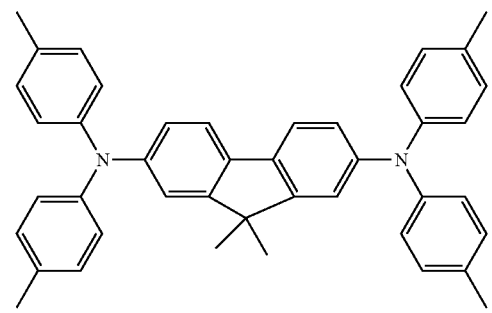

<Comparative Compound m3>

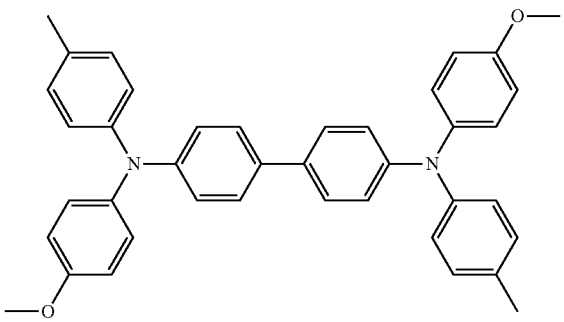

-continued

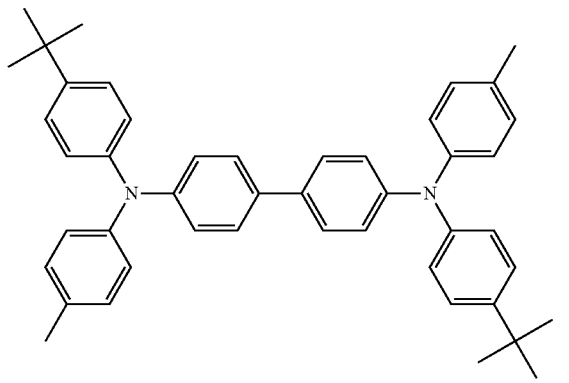

<Comparative Compound m4>

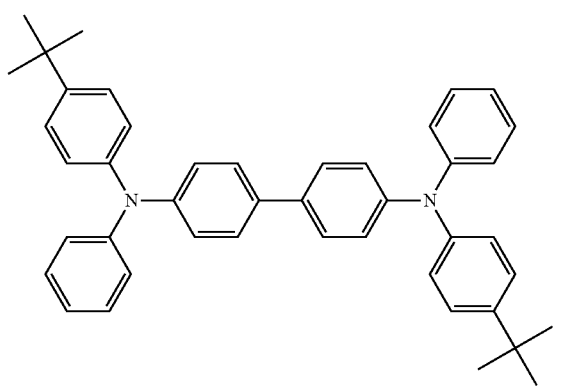

<Comparative Compound m5>

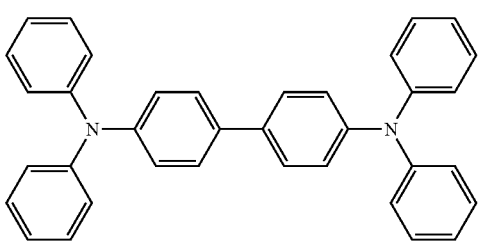

<Comparative Compound m6>

<Evaluations>

Each of the produced electrochromic elements was subjected to a continuous coloring test, a photodurability test, a color test, and deterioration analysis. The results are presented in Table 2.

[Test 2-1: Durability Test to Repetitive Use]

Each of the produced electrochromic elements of Examples and Comparative Examples was tested. Voltage of 2 V was applied between the drawing part of the first electrode and the drawing part of second electrode for 5 seconds to color the electrochromic element, followed by applying voltage of −2 V between the drawing part of the first electrode and the drawing part of the second electrode for 5 seconds to decolor the electrochromic element, which was determined as 1 operation of coloring and decoloring. The coloring and decoloring operation was performed 10,000 times. The maximum absorbance in the visible region (380 nm to 780 nm) during the operations was determined as λmax (490 nm in Example 1). A change in the absorbance after the 10,000 operations was measured by means of a spectrometer (USB4000, available from Ocean Optics, Inc.), and was evaluated based on the following criteria.

[Evaluation Criteria]

A: The absorbance of λmax was 95% or greater of the initial absorbance.
B: The absorbance of λmax was 90% or greater or less than 95% of the initial absorbance.
C: The absorbance of λmax was less than 90% of the initial absorbance.

[Test 2-2: Continuous Coloring Test]

Each of the produced electrochromic elements of Examples and Comparative Examples was tested. Voltage of 1.6 V was applied between the first electrode and the second electrode to color the electrochromic element, and the colored state was maintained continuously for 48 hours. The absorbance in the visible region (380 nm to 780 nm) before and after the application of voltage was measured by a spectrometer (USB4000, available from Ocean Optics, Inc.), and each yellow index (YI) was calculated. A difference in YI before and after the application of voltage was determined as ΔYI, which was evaluated based on the following criteria.

[Evaluation Criteria]

A: ΔYI was less than 0.5.
B: ΔYI was 0.5 or greater but less than 3.
C: ΔYI was 3 or greater.

[Test 2-3: Photodurability Test]

Each of the produced electrochromic elements of Examples and Comparative Examples was tested. Voltage of 1.6 V was applied between the first electrode and the second electrode to color the electrochromic element. While maintaining the colored stated of the electrochromic element, the electrochromic element was continuously irradiated with light through a UV-cut filter (product name: Lumicool 1501UH, available from LINTEC Corporation) by artificial solar lighting (product name: SOLAX XC-100 W, available from available from SERIC Ltd., illuminance: 150,000 lux) for 48 hours. Then, the electrochromic element was irradiated with light by a deuterium tungsten halogen light source (product name: DH-2000, available from Ocean Optics, Inc.). The transmittance of the electrochromic element in the visible region (380 nm to 780 nm) before and after the irradiation was measured by a spectrometer (USB4000, available from Ocean Optics, Inc.), and each yellow index (YI) was calculated. A difference in YI before and after the irradiation was determined as ΔYI, which was evaluated based on the following criteria.

[Evaluation Criteria]

A: ΔYI was less than 5.
B: ΔYI was 5 or greater but less than 10.
C: ΔYI was 10 or greater.

TABLE 2

| | Electrochromic compound 2-1 | | | | |
|---|---|---|---|---|---|
| | Type | Location for use | Test 2-1 | Test 2-2 | Test 2-3 |
| Ex. 2-1 | Exemplary Compound M1 | Electrolyte layer | A | A | A |
| Ex. 2-2 | Exemplary Compound M2 | Electrolyte layer | A | A | A |
| Ex. 2-3 | Exemplary Compound M3 | Electrolyte layer | A | A | A |
| Ex. 2-4 | Exemplary Compound M4 | Electrolyte layer | A | A | A |
| Ex. 2-5 | Exemplary Compound M5 | Electrolyte layer | A | A | A |
| Comp. Ex. 2-1 | Comparative Compound m1 | Electrolyte layer | B | B | C |

TABLE 2-continued

| | Electrochromic compound 2-1 | | | | |
|---|---|---|---|---|---|
| | Type | Location for use | Test 2-1 | Test 2-2 | Test 2-3 |
| Comp. Ex. 2-2 | Comparative Compound m2 | Electrolyte layer | B | B | C |
| Comp. Ex. 2-3 | Comparative Compound m3 | Electrolyte layer | B | B | C |
| Comp. Ex. 2-4 | Comparative Compound m4 | Electrolyte layor | B | B | C |
| Comp. Ex. 2-5 | Comparative Compound m5 | Electrolyte layer | C | C | C |
| Comp. Ex. 2-6 | Comparative Compound m6 | Electrolyte layer | C | C | C |

It was confirmed from the results of Table 2 that the electrochromic elements of Examples 2-1 to 2-5 achieved both continuous coloring and photodurability, and had excellent continuous driving stability and photodurability. It was confirmed that the electrochromic elements of Comparative Examples 2-1 to 2-6 were insufficient in both continuous coloring and photodurability.

Accordingly, Electrochromic Compound 2-1 of the present disclosure contributed to improvement in the continuous driving stability and photodurability of the electrochromic element.

Example 3-1

<Production of Third Electrochromic Element>

An electrochromic element of Example 3-1 was produced in the same manner as in Example 1-1, except that, in the first electrochromic composition, an equal part (50 parts by mass) of Exemplary Compound TPA1 was added to Exemplary Compound 1 and the mixture thereof was used as the first electrochromic compound.

<Coloring and Decoloring Operation>

Coloring and decoloring of the produced electrochromic element of Example 3-1 were confirmed in the same manner as the confirmation method used for the electrochromic elements of Examples 1 and 2. As a result, coloring in black as a mixture of blue and orange owing to the electrochromic compounds of the electrochromic layer was confirmed in the area where the first electrode and the second electrode were overlapped, when voltage of −2 V was applied between the drawing part of the first electrode and the drawing part of the second electrode for 5 seconds. Moreover, it was confirmed that, when voltage of +2 V was applied between the drawing part of the first electrode and the drawing part of the second electrode for 5 seconds, the colored area was decolored and turned transparent.

Comparative Examples 3-1 to 3-3

Electrochromic elements of Comparative Examples 3-1 to 3-3 were produced in the same manner as in Example 3-1, except that Exemplary Compound 1 used in the first electrochromic compound was changed to Comparative Compounds 1, 2, and 3, respectively. Similarly to the electrochromic element of Example 3-1, it was confirmed that the electrochromic elements of Comparative Examples 3-1 to 3-3 colored in black as blue and orange were mixed.

<Evaluations>

Each of the produced electrochromic elements was subjected to a durability test to repetitive use, and a continuous coloring test. The results are presented in Table 3.

<Test 3-1: Durability Test to Repetitive Use>

Each of the produced electrochromic elements of Examples and Comparative Examples was tested. Voltage of 2 V was applied between the drawing part of the first electrode and the drawing part of second electrode for 5 seconds to color the electrochromic element, followed by applying voltage of −2 V between the drawing part of the first electrode and the drawing part of the second electrode for 5 seconds to decolor the electrochromic element, which was determined as 1 operation of coloring and decoloring. The coloring and decoloring operation was performed 10,000 times. The maximum absorbance in the visible region (380 nm to 780 nm) during the operations was determined as λmax (490 nm and 660 nm in Example 3-1, and 490 nm was set as the standard). A change in the absorbance after the 10,000 operations was measured by means of a spectrometer (USB4000, available from Ocean Optics, Inc.), and was evaluated based on the following criteria.

[Evaluation Criteria]

A: The absorbance of λmax was 95% or greater of the initial absorbance.

B: The absorbance of λmax was 90% or greater or less than 95% of the initial absorbance.

C: The absorbance of λmax was less than 90% of the initial absorbance.

[Test 3-2: Continuous Coloring Test]

Each of the produced electrochromic elements of Examples and Comparative Examples was tested. Voltage of 1.6 V was applied between the first electrode and the second electrode to color the electrochromic element, and the colored state was maintained continuously for 48 hours. The absorbance in the visible region (380 nm to 780 nm) before and after the application of voltage was measured by a spectrometer (USB4000, is available from Ocean Optics, Inc.), and each yellow index (YI) was calculated. A difference in YI before and after the application of voltage was determined as ΔYI, which was evaluated based on the following criteria.

[Evaluation Criteria]

A: ΔYI was less than 0.5.

B: ΔYI was 0.5 or greater but less than 3.

C: ΔYI was 3 or greater.

[Test 3-3: Photodurability Test]

Each of the produced electrochromic elements of Examples and Comparative Examples was tested. Voltage of 1.6 V was applied between the first electrode and the second electrode to color the electrochromic element. While maintaining the colored stated of the electrochromic element, the electrochromic element was continuously irradiated with light through a UV-cut filter (product name: Lumicool 1501UH, available from LINTEC Corporation) by artificial solar lighting (product name: SOLAX XC-100 W, available from available from SERIC Ltd., illuminance: 150,000 lux) for 48 hours. Then, the electrochromic element was irradiated with light by a deuterium tungsten halogen light source (product name: DH-2000, available from Ocean Optics, Inc.). The transmittance of the electrochromic element in the visible region (380 nm to 780 nm) before and after the irradiation was measured by a spectrometer (USB4000, available from Ocean Optics, Inc.), and each yellow index (YI) was calculated. A difference in YI before and after the irradiation was determined as ΔYI, which was evaluated based on the following criteria.

[Evaluation Criteria]
A: ΔYI was less than 5.
B: ΔYI was 5 or greater but less than 10.
C: ΔYI was 10 or greater.

TABLE 3-1

| | First electrochromic composition | | | Second electrochromic composition | |
|---|---|---|---|---|---|
| | First type of first electrochromic compound | Second type of first electrochromic compound | Location for use | Species of second electrochromic compound | Location for use |
| Ex. 3-1 | Exemplary Compound 1 | Exemplary Compound TPA1 | First electrochromic layer | Exemplary Compound A | Second electrochromic layer |
| Comp. Ex. 3-1 | Comparative Compound 1 | Exemplary Compound TPA1 | First electrochromic layer | Exemplary Compound A | Second electrochromic layer |
| Comp. Ex. 3-2 | Comparative Compound 2 | Exemplary Compound TPA1 | First electrochromic layer | Exemplary Compound A | Second electrochromic layer |
| Comp. Ex. 3-3 | Comparative Compound 3 | Exemplary Compound TPA1 | First electrochromic layer | Exemplary Compound A | Second electrochromic layer |

TABLE 3-2

| | Test 3-1 | Test 3-2 | Test 3-3 |
|---|---|---|---|
| Ex. 3-1 | A | A | A |
| Comp. Ex. 3-1 | B | B | B |
| Comp. Ex. 3-2 | B | B | B |
| Comp. Ex. 3-3 | B | B | B |

It was confirmed from the results of Tables 3-1 and 3-2 that the electrochromic elements of Example 3-1 and Comparative Examples 3-1 to 3-3 colored in black as the mixture of blue and orange, and coloring of black could be obtained as the first electrochromic composition included the benzidine compound.

Moreover, it was confirmed from the results of Tables 3-1 and 3-2 that the electrochromic element of Example 3-1 achieved both the durability against repetitive use and continuous coloring, and had excellent continuous driving stability and photodurability. It was confirmed that, on the other hand, the electrochromic elements of Comparative Examples 3-1 to 3-3 were insufficient in the durability against repetitive use, continuous coloring, and photodurability, and had not very satisfactory properties.

Accordingly, the first electrochromic composition contributed to improvement in continuous driving stability and photodurability of the electrochromic element.

Example 4-1

<Production of Fourth Electrochromic Element>
An electrochromic element of Example 4-1 was produced in the same manner as in Example 2-1, except that an equal part (50 parts by mass) of Exemplary Compound TPAM1 was added to Exemplary Compound M1 and the mixture thereof was used as Electrochromic Compound 2-1.

<Evaluations>
Each of the produced electrochromic elements was subjected to a durability test to repetitive use, and a continuous coloring test. The results are presented in Table 4.
(Coloring and Decoloring Operation)
Coloring and decoloring of the produced electrochromic element of Example 4 were confirmed in the same manner as the confirmation method used for the electrochromic elements of Examples 1 and 2. As a result, coloring in black as a mixture of blue and orange owing to the electrochromic compounds of the electrochromic layer was confirmed in the area where the first electrode and the second electrode were overlapped, when voltage of 2 V was applied between the drawing part of the first electrode and the drawing part of the second electrode for 5 seconds. Moreover, it was confirmed that, when voltage of −2 V was applied between the drawing part of the first electrode and the drawing part of the second electrode for 5 seconds, the colored area was decolored and turned transparent.

Comparative Examples 4-1 to 4-3

Electrochromic elements of Comparative Examples 4-1 to 4-3 were produced in the same manner as in Example 4-1, except that Exemplary Compound M1 used as Electrochromic Compound 2-1 was changed to Comparative Compounds m1, m2, and m3, respectively. Similarly to the electrochromic element of Example 4-1, it was confirmed that the electrochromic elements of Comparative Examples 4-1 to 4-3 colored in black as blue and orange were mixed.
<Evaluations>
Each of the produced electrochromic elements was subjected to a durability test for repetitive use, a continuous coloring test, and a photodurability test. The results are presented in Table 4.
[Test 4-1: Durability Test to Repetitive Use]
Each of the produced electrochromic elements of Examples and Comparative Examples was tested. Voltage of 2 V was applied between the drawing part of the first electrode and the drawing part of second electrode for 5 seconds to color the electrochromic element, followed by applying voltage of −2 V between the drawing part of the first electrode and the drawing part of the second electrode for 5 seconds to decolor the electrochromic element, which was determined as 1 operation of coloring and decoloring. The coloring and decoloring operation was performed 10,000 times. The maximum absorbance in the visible region (380 nm to 780 nm) during the operations was determined as λmax (490 nm and 660 nm in Example 4-1, and 490 nm was set as the standard). A change in the absorbance after the 10,000 operations was measured by means of a spectrometer (USB4000, available from Ocean Optics, Inc.), and was evaluated based on the following criteria.
[Evaluation criteria]
A: The absorbance of λmax was 95% or greater of the initial absorbance.
B: The absorbance of λmax was 90% or greater or less than 95% of the initial absorbance.
C: The absorbance of λmax was less than 90% of the initial absorbance.
[Test 4-2: Continuous Coloring Test]
Each of the produced electrochromic elements of Examples and Comparative Examples was tested. Voltage of 1.6 V was applied between the first electrode and the second electrode to color the electrochromic element, and the colored state was maintained continuously for 48 hours. The absorbance in the visible region (380 nm to 780 nm) before and after the application of voltage was measured by a spectrometer (USB4000, available from Ocean Optics, Inc.), and each yellow index (YI) was calculated. A difference in YI before and after the application of voltage was determined as ΔYI, which was evaluated based on the following criteria.

[Evaluation Criteria]
A: ΔYI was less than 0.5.
B: ΔYI was 0.5 or greater but less than 3.
C: ΔYI was 3 or greater.

[Test 4-3: Photodurability Test]

Each of the produced electrochromic elements of Examples and Comparative Examples was tested. Voltage of 1.6 V was applied between the first electrode and the second electrode to color the electrochromic element. While maintaining the colored stated of the electrochromic element, the electrochromic element was continuously irradiated with light through a UV-cut filter (product name: Lumicool 1501UH, available from LINTEC Corporation) by artificial solar lighting (product name: SOLAX XC-100 W, available from available from SERIC Ltd., illuminance: 150,000 lux) for 48 hours. Then, the electrochromic element was irradiated with light by a deuterium tungsten halogen light source (product name: DH-2000, available from Ocean Optics, Inc.). The transmittance of the electrochromic element in the visible region (380 nm to 780 nm) before and after the irradiation was measured by a spectrometer (USB4000, available from Ocean Optics, Inc.), and each yellow index (YI) was calculated. A difference in YI before and after the irradiation was determined as ΔYI, which was evaluated based on the following criteria.

[Evaluation Criteria]
A: ΔYI was less than 5.
B: ΔYI was 5 or greater but less than 10.
C: ΔYI was 10 or greater.

TABLE 4

| | Electrochromic Compound 2-1 | | | | |
|---|---|---|---|---|---|
| | First type | Second type | Location for use | Test 4-1 | Test 4-2 | Test 4-3 |
| Ex. 4-1 | Exemplary Compound M1 | Exemplary Compound TPAM1 | Electrolyte layer | A | A | A |
| Comp. Ex. 4-1 | Comparative Compound m1 | Exemplary Compound TPAM2 | Electrolyte layer | B | B | C |
| Comp. Ex. 4-2 | Comparative Compound m2 | Exemplary Compound TPAM3 | Electrolyte layer | B | B | C |
| Comp. Ex. 4-3 | Comparative Compound m3 | Exemplary Compound TPAM4 | Electrolyte layer | B | B | C |

It was confirmed from the results of Table 4 that the electrochromic elements of Example 4-1 and Comparative Examples 4-1 to 4-3 colored in black as the mixture of blue and orange, and coloring of black could be obtained as Electrochromic Compound 2-1 included the benzidine compound.

Moreover, it was confirmed from the results of Table 4 that the electrochromic element of Example 4-1 achieved both the durability against repetitive use and continuous coloring, and had excellent continuous driving stability and photodurability. It was confirmed that, on the other hand, the electrochromic elements of Comparative Examples 4-1 to 4-3 were insufficient in the durability against repetitive use, continuous coloring, and photodurability, and had not very satisfactory properties.

Accordingly, Electrochromic Compound 2-1 contributed to improvement in continuous driving stability and photodurability of the electrochromic element.

For example, embodiments of the present disclosure are as follows.

<1> An electrochromic element including:
a first electrode;
a second electrode to face the first electrode with a gap between the first electrode and the second electrode;
an electrolyte layer disposed between the first electrode and the second electrode; and
a layer including an electrochromic compound represented by General Formula (1), where the layer is disposed on or above the first electrode,

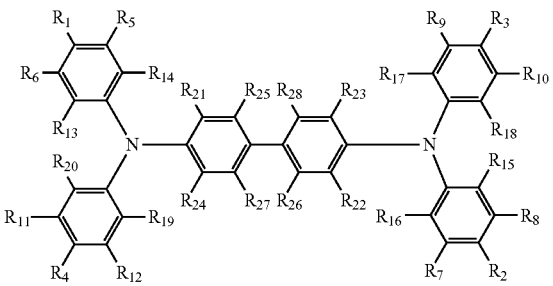

General Formula (1)

where, in General Formula (1), $R_1$ to $R_4$ are each a monovalent organic group in which no hydrogen atom is present at a benzyl site, where the monovalent organic group may include, as a partial structure, a polymerizable functional group; and $R_5$ to $R_{28}$ are each a hydrogen atom, an alkyl group, or an alkoxy group, where $R_{25}$ and $R_{28}$, or $R_{26}$ and $R_{27}$ may be bonded together to form a structure represented by General Formula (2),

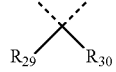

General Formula (2)

where, in General Formula (2), $R_{29}$ and $R_{30}$ are each an alkyl group, an alkoxy group, or an aryl group, where $R_{29}$ and $R_{30}$ may be bonded via a common bond to form a cyclic structure when $R_{29}$ and $R_{30}$ are both aryl groups.

<2> An electrochromic element including:
a first electrode;
a second electrode to face the first electrode with a gap between the first electrode and the second electrode; and
an electrolyte layer disposed between the first electrode and the second electrode,
wherein the electrolyte layer includes an electrochromic compound represented by General Formula (1), General Formula (1)

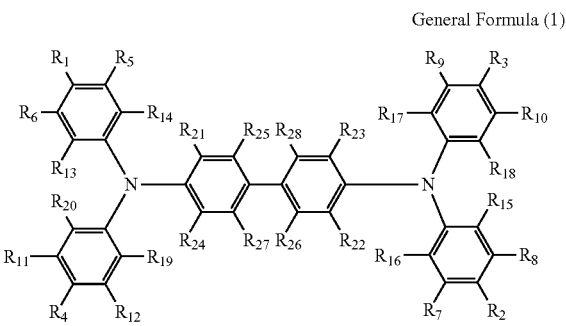

where, in General Formula (1), $R_1$ to $R_4$ are each a monovalent organic group in which no hydrogen atom is present at a benzyl site, where the monovalent organic group may include, as a partial structure, a polymerizable functional group; and $R_5$ to $R_{28}$ are each a hydrogen atom, an alkyl group, or an alkoxy group, where $R_{25}$ and $R_{28}$, or $R_{26}$ and $R_{27}$ may be bonded together to form a structure represented by General Formula (2), General Formula (2)

where, in General Formula (2), $R_{29}$ and $R_{30}$ are each an alkyl group, an alkoxy group, or an aryl group, where $R_{29}$ and $R_{30}$ may be bonded via a common bond to form a cyclic structure when $R_{29}$ and $R_{30}$ are both aryl groups.

<3> The electrochromic element according to <1> or <2>, wherein the monovalent organic group is at least one selected from the group consisting of a tert-butyl group, a trialkylsilyl group, a triarylsilyl group, a diallyl monoalkylsilyl group, an alkoxy group, and a phenoxy group.
<4> The electrochromic element according to any one of <1> to <3>, wherein, in General Formula (1), one of $R_1$ to $R_{28}$ is a group including a polymerizable functional group.
<5> The electrochromic element according to <4>, wherein the polymerizable functional group is a (meth)acryloyl group or a (meth)acryloxy group.
<6> The electrochromic element according to any one of <1> to <5>, wherein $R_{13}$ to $R_{24}$ are each a hydrogen atom.
<7> An electrochromic compound represented by General Formula (1), General Formula (1)

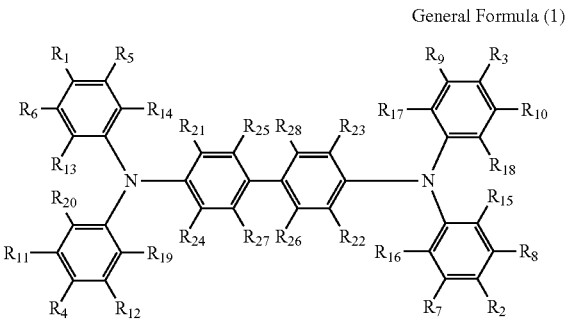

where, in General Formula (1), $R_1$ to $R_4$ are each a monovalent organic group in which no hydrogen atom is present at a benzyl site, where the monovalent organic group may include, as a partial structure, a polymerizable functional group; and $R_5$ to $R_{28}$ are each a hydrogen atom, an alkyl group, or an alkoxy group, where $R_{25}$ and $R_{28}$, or $R_{28}$ and $R_{27}$ may be bonded together to form a structure represented by General Formula (2), General Formula (2)

where, in General Formula (2), $R_{29}$ and $R_{30}$ are each an alkyl group, an alkoxy group, or an aryl group, where $R_{29}$ and $R_{30}$ may be bonded via a common bond to form a cyclic structure when $R_{29}$ and $R_{30}$ are both aryl groups.
<8> The electrochromic compound according to <7>, wherein the monovalent organic group is at least one selected from the group consisting of a tert-butyl group, a trialkylsilyl group, a triarylsilyl group, a diallyl monoalkylsilyl group, an alkoxy group, and a phenoxy group.
<9> The electrochromic compound according to <7> or <8>, wherein, in General Formula (1), one of $R_1$ to $R_{28}$ is a group including a polymerizable functional group.
<10> The electrochromic compound according to <9>, wherein the polymerizable functional group is a (meth)acryloyl group or a (meth)acryloxy group.
<11> The electrochromic compound according to any one of <7> to <10>, wherein $R_{13}$ to $R_{24}$ are each a hydrogen atom.
<12> An electrochromic composition including the electrochromic compound according to any one of <7> to <11>.
<13> The electrochromic composition according to <12>, further including
a radical polymerizable compound that is different from the electrochromic compound.
<14> The electrochromic composition according to <12> or <13>, wherein the polymerizable functional group included in the electrochromic composition is polymerized or cross-linked.
<15> An electrochromic element including:
a first electrode;
a second electrode to face the first electrode with a gap between the first electrode and the second electrode;
an electrolyte layer disposed between the first electrode and the second electrode; and
a layer including the electrochromic composition according to any one of <12> to <14>, where the layer is disposed on or above the first electrode. <16> An electrochromic element including;
a first electrode;
a second electrode to face the first electrode with a gap between the first electrode and the second electrode; and
an electrolyte layer disposed between the first electrode and the second electrode,
wherein the electrolyte layer includes the electrochromic composition according to any one of <12> to <14>.

The electrochromic element according to any one of <1> to <6> and <15> to <16>, the electrochromic compound according to any one of <7> to <11>, and the electrochromic composition according to any one of <12> to <14> can solve the various problems existing in the art, and can achieve the object of the present disclosure.

What is claimed is:

1. An electrochromic element comprising:
a first electrode;
a second electrode to face the first electrode with a gap between the first electrode and the second electrode;
an electrolyte layer disposed between the first electrode and the second electrode; and
a layer including an electrochromic compound represented by General Formula (1), where the layer is disposed on or above the first electrode,

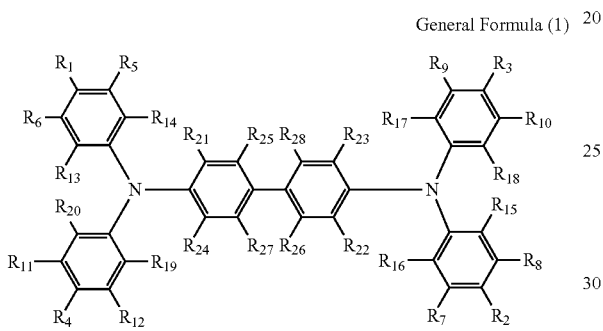

General Formula (1)

where, in General Formula (1), $R_1$ to $R_4$ are each a monovalent organic group in which no hydrogen atom is present at an atom which directly connects to a benzene ring, and at least one of and not all of $R_1$ to $R_4$ each has a polymerizable functional group as a terminal group; and $R_5$ to $R_{28}$ are each a hydrogen atom, an alkyl group, or an alkoxy group, where $R_{25}$ and $R_{28}$, or $R_{26}$ and $R_{27}$ may be bonded together to form a structure represented by General Formula (2),

General Formula (2)

where, in General Formula (2), $R_{29}$ and $R_{30}$ are each an alkyl group, an alkoxy group, or an aryl group, where $R_{29}$ and $R_{30}$ may be bonded via a common bond to form a cyclic structure when $R_{29}$ and $R_{30}$ are both aryl groups.

2. The electrochromic element according to claim 1, wherein the monovalent organic group is at least one selected from the group consisting of a tert-butyl group, a trialkylsilyl group, a triarylsilyl group, a diallyl monoalkylsilyl group, an alkoxy group, and a phenoxy group.

3. The electrochromic element according to claim 1, wherein the polymerizable functional group is a (meth)acryloyl group or a (meth)acryloxy group.

4. The electrochromic element according to claim 1, wherein $R_{13}$ to $R_{24}$ are each a hydrogen atom.

5. An electrochromic element comprising:
a first electrode;
a second electrode to face the first electrode with a gap between the first electrode and the second electrode; and
an electrolyte layer disposed between the first electrode and the second electrode, wherein the electrolyte layer includes an electrochromic compound represented by General Formula (1),

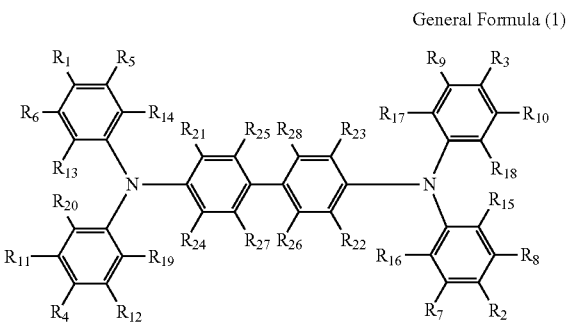

General Formula (1)

where, in General Formula (1), $R_1$ to $R_4$ are each a monovalent organic group in which no hydrogen atom is present at an atom which directly connects to a benzene ring, and at least one of and not all of $R_1$ to $R_4$ each has a polymerizable functional group as a terminal group; and $R_5$ to $R_{28}$ are each a hydrogen atom, an alkyl group, or an alkoxy group, where $R_{25}$ and $R_{28}$, or $R_{26}$ and $R_{27}$ may be bonded together to form a structure represented by General Formula (2),

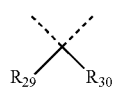

General Formula (2)

where, in General Formula (2), $R_{29}$ and $R_{30}$ are each an alkyl group, an alkoxy group, or an aryl group, where $R_{29}$ and $R_{30}$ may be bonded via a common bond to form a cyclic structure when $R_{29}$ and $R_{30}$ are both aryl groups.

6. The electrochromic element according to claim 5, wherein the monovalent organic group is at least one selected from the group consisting of a tert-butyl group, a trialkylsilyl group, a triarylsilyl group, a diallyl monoalkylsilyl group, an alkoxy group, and a phenoxy group.

7. The electrochromic compound according to claim 5, wherein the polymerizable functional group is a (meth)acryloyl group or a (meth)acryloxy group.

8. The electrochromic element according to claim 5, wherein $R_{13}$ to $R_{24}$ are each a hydrogen atom.

9. An electrochromic compound represented by General Formula (1),

General Formula (1)

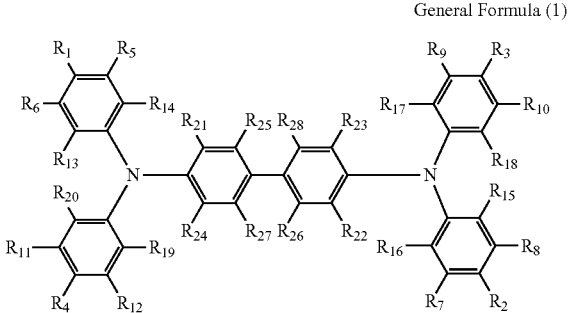

where, in General Formula (1), $R_1$ to $R_4$ are each a monovalent organic group in which no hydrogen atom is present at an atom which directly connects to a benzene ring, and at least one of and not all of $R_1$ to $R_4$ each has a polymerizable functional group as a terminal group; and $R_5$ to $R_{28}$ are each a hydrogen atom, an alkyl group, or an alkoxy group, where $R_{25}$ and $R_{28}$, or $R_{26}$ and $R_{27}$ may be bonded together to form a structure represented by General Formula (2), General Formula (2)

where, in General Formula (2), $R_{29}$ and $R_{30}$ are each an alkyl group, an alkoxy group, or an aryl group, where $R_{29}$ and $R_{30}$ may be bonded via a common bond to form a cyclic structure when $R_{29}$ and $R_{30}$ are both aryl groups.

10. The electrochromic compound according to claim 9, wherein the monovalent organic group is at least one selected from the group consisting of a tert-butyl group, a trialkylsilyl group, a triarylsilyl group, a diallyl monoalkylsilyl group, an alkoxy group, and a phenoxy group.

11. The electrochromic compound according to claim 9, wherein the polymerizable functional group is a (meth)acryloyl group or a (meth)acryloxy group.

12. The electrochromic compound according to claim 9, wherein $R_{13}$ to $R_{24}$ are each a hydrogen atom.

13. An electrochromic composition comprising the electrochromic compound according to claim 9.

14. The electrochromic composition according to claim 13, further comprising a radical polymerizable compound that is different from the electrochromic compound.

15. The electrochromic composition according to claim 13, wherein the polymerizable functional group included in the electrochromic composition is polymerized or cross-linked.

16. An electrochromic element comprising:
a first electrode;
a second electrode to face the first electrode with a gap between the first electrode and the second electrode;
an electrolyte layer disposed between the first electrode and the second electrode; and
a layer including the electrochromic composition according to claim 13, where the layer is disposed on or above the first electrode.

17. An electrochromic element comprising:
a first electrode;
a second electrode to face the first electrode with a gap between the first electrode and the second electrode; and
an electrolyte layer disposed between the first electrode and the second electrode, wherein the electrolyte layer includes the electrochromic composition according to claim 13.

* * * * *